United States Patent [19]
Kindsvogel et al.

[11] Patent Number: 5,770,445
[45] Date of Patent: Jun. 23, 1998

[54] GLUCAGON RECEPTOR PROTEINS, PEPTIDES, AND ANTIBODIES

[75] Inventors: Wayne R. Kindsvogel; Laura J. Jelinek, both of Seattle; Paul O. Sheppard, Redmond; Francis J. Grant, Seattle; Joseph L. Kuijper, Bothell; Donald C. Foster, Seattle; Si Lok, Seattle; Patrick J. O'Hara, Seattle, all of Wash.

[73] Assignee: ZymoGenetics, Inc., Seattle, Wash.

[21] Appl. No.: 453,956

[22] Filed: May 30, 1995

Related U.S. Application Data

[60] Division of Ser. No. 86,631, Jul. 1, 1993, which is a continuation-in-part of Ser. No. 938,331, Aug. 28, 1992, abandoned.

[51] Int. Cl.$^6$ .......................... C07K 14/72; C07K 16/28; C12N 15/12
[52] U.S. Cl. .......................... 435/334; 530/350; 530/324; 530/325; 530/326; 530/327; 530/328; 530/338.22; 530/389.1; 514/2
[58] Field of Search ...................................... 530/350, 324, 530/325, 326, 327, 328, 387.2, 388.22, 389.1; 435/240.27, 24; 514/2

[56] References Cited

U.S. PATENT DOCUMENTS 4,430,326  2/1984  Hruby et al. .

FOREIGN PATENT DOCUMENTS

92/12998  8/1992  WIPO .

OTHER PUBLICATIONS

Reilly, T. M., et al. (1986) *J. Immunol.* 137:597–602.
Wang, C., et al. (1990) *J. Biol. Chem.* 266:12372–78.
Unson, C. G., et al. (1996) *Proc. Natl. Acad. Sci. USA* 93:310–15.

Dighe et al., "Glucagon–Stimulable Adenylyl Cyclase in Rat Liver," *J. Clinic. Invest.*, 73:1013–1023 (1984).
Wright et al., "Photoaffinity Labeling of the Glucagon Receptor with a New Glucagon Analog," *Eur. J. Biochem.*, 141:63–67 (1984).
Iwanij and Hur, "Direct Cross–Linking of $^{125}$I–labeled Glucagon to its Membrane Receptor by UV Irradiation," *Proc. Natl. Acad. Sci.*, 82:325–329 (1985).
Krstenansky et al., "Importance of the 10–13 Region of Glucagon for its Receptor Interactions and Activation of Adenylate Cyclase," *Biochem.*, 25:3833–3839 (1986).
Murphy et al., "The Relation of Predicted Structure to Observed Conformation and Activity of Glucagon Analogs Containing Replacements at Positions 19, 22 and 23," *J. Biol. Chem.*, 262:17304–17312 (Dec. 25, 1987).

(List continued on next page.)

*Primary Examiner*—David L. Fitzgerald
*Attorney, Agent, or Firm*—Townsend and Townsend and Crew LLP

[57] ABSTRACT

The present invention provides isolated DNA molecules comprising a DNA segment encoding a glucagon receptor. Also provided are DNA constructs comprising a first DNA segment encoding a glucagon receptor operably linked to additional DNA segments required for the expression of the first DNA segment, as well as host cells containing such DNA constructs. The present invention also provides a method for detecting the presence of glucagon antagonists, comprising the steps of (a) exposing a compound in the presence of a glucagon against to a recombinant glucagon receptor coupled to a response pathway under conditions and for time sufficient to allow binding of the compound to the receptor and an associated response through the pathway, and (b) detecting a reduction in the stimulation of the response pathway resulting from the binding of the compound to the glucagon receptor, relative to the stimulation of the response pathway by the glucagon agonist alone and therefrom determining the presence of a glucagon antagonist.

18 Claims, 7 Drawing Sheets

OTHER PUBLICATIONS

Andreu et al., "Glucagon Anatagonists, Synthesis and Inhibitory Properties of Asp³–containing Glucagon Analogs," *Eur. J. Biochem.*, 164:585–590 (1987).

Padrell et al., "The Hepatic Glucagon Receptor: A Comparative Study of the Regulatory and Structural Properties," *Endochrin.*, 120:2316–2325 (1987).

Unson et al., "Synthetic Peptide Antagonists of Glucagon," *Proc. Natl. Acad. Sci.*, 84:4083–4087 (1987).

Deutsch et al., "Vasoactive Intestinal Peptide Increases Intracellular cAMP and Gondotropin–α Gene Activity in JEG–3 Syncytial Trophoblasts," *J. Biol. Chem.*, 265:10274–10281 (1990).

Blache et al., "Glucagon–(19–29), a $Ca^{2+}$Pump Inhibitory Peptide is Processed from Glucagon in the Rat Liver Plasma Membrane by a Thiol Endopeptidase," *J. Biol. Chem.* 265:21514–21519 (1990).

El–Maghrabi, et al., The Rat Fructose–1,6–bisphosphatase Gene, *J. Biol. Chem.*, 266:2115–2120 (Feb. 5, 1991).

D.E. Titus, ed., "Promega Protocols and Applications Guide," (Mar. 1991).

Post et al., "Identification of a $Mg^{2-}$ and Guanyl Nucleotide– dependent Glucagon Receptor Cycle by Use of Permeabilized Canine Hepatocytes," *J. Biol. Chem.*, 267:25776–25785 (1992).

Svoboda et al., "A cDNA Construct Allowing the Expression of Rat Hepatic Glucagon Receptors," *Biochem. Biophys. Res. Commun.* 192:135–142 (1993).

Rodbell et al., "The Reaction of Glucagon with its Receptors: Evidence for Discrete Regions of Activity and Binding in the Glucagon Molecule," *Proc. Natl. Acad. Sci. USA*, 68:909–913 (1971).

Sonne et al., "Binding of $^{125}$I–Labeled Glucagon and Glucagon–Stimulated Accumulation of Adenosine 3':5'–Monophosphate in Isolated Intact Rat Hepatocytes," *J. Biol. Chem.* 253:3203–3210 (1978).

Bhathena et al., "Insulin, Glucagon, and Somatostatin Receptors on Cultured Cells and Clones from Rat Islet Cell Tumor," *Diabetes*, 31:521–531 (1982).

Herberg et al., "The Hepatic Glucagon Receptor," *J. Biol. Chem.*, 259:9285–9294 (1984).

Wakelam et al., "Activation of Two Signal–Transduction Systems in Hepatocytes by Glucagon," *Nature*, 323:68–71 (1986).

Gysin et al., "Synthesis of Two Glucagon Antagonists: Receptor Binding, Adenylate Cyclase, and Effects on Blood Plasma Glucose Levels," *J. Med. Chem.*, 30:1409–1415 (1987).

Iyengar et al., "The Glucagon Receptor: Structural Analysis by Covalent Labeling Techniques," *Pharmac. Ther.* 37:151–165 (1988).

Watanabe et al., "Glucagon Receptors in Endothelial and Kupffer Cells of Mouse Liver," *J. Histochemistry and Cytochemistry*, 36:1081–1089 (1988).

Vincent et al., "The Characterization of Monoclonal Antibodies to the Heptatic Glucagon Receptor," *J. Cell. Biol.* 107:65A (1988).

Sambrook, J., et al., eds. *Molecule Cloning*, Cold Spring Harbor, New York, Chapter 16 (1989).

McVittie et al., "Stabilization of Soluable Active Rat Liver Glucagon Receptor," *Arch. Biochem. Biophys.* 273:254–263, (1989).

Unson et al., "Biological Activities of des–His¹ [Glu⁹] Glucagon Amide, A Glucagon Antagonist," *Peptides* 10:1171–1177 (1989).

Amherdt et al., "Binding and Internalization of Somatostatin, Insulin, and Glucagon by Cultured Rat Islet Cells," *J. Clin. Invest.*, 84:412–417 (1989).

Murphy et al., "Glucagon Desensitization of Adenylate Cylase and Stimulation of Inositol Phospholipid Metabolism Does Not Involve the Inhibitory Guanine Nucleotide Regulatory Protein $G_i$, which is Inactivated upon Challenge of Hepatocytes with Glucagon," *Biochem J.*, 259:191–197 (1989).

Libert et al., "Selective Amplification and Cloning of Four New Members of the G Protein–Coupled Receptor Family," *Science*, 244:569–572 (May 5, 1989).

Buharucha et al., "Analysis of Glucagon–Receptor Interactions on Isolated Canine Hepatocytes," *J. Biol. Chem.*, 265:3070–3079 (1990).

Iwanij et al., Characterization of the Glucagon Receptor and its Functional Domains Using Monoclonal Antibodies, *J. Biol. Chem.*, 265:21302–21306 (1990).

Authier et al., "Fate of Injected Glucagon Taken up by Rat Liver in vivo," *Biochem. J.* 272:703–712 (1990).

Pittner et al., "Activation of Membrane Protein Kinase C by Glucagon and $Ca^{2+}$–Mobilizing Hormones in Cultured Rat Hepatocytes," *Biochem. J.*, 277:371–378 (1991).

McMahan et al., "A Novel IL–1 Receptor, Cloned From B Cells by Mammalian Expression, is Expressed in Many Cell Types," *EMBO J.* 10:2821–2832 (1991).

Ishihara et al., "Molecular Cloning and Expression of cDNA Encoding the Secretin Receptor," *EMBO J.* 10:1635–1641, (Jul., 1991).

Lin et al., "Expression Cloning of an Adenylate Cyclase–Coupled Calcitonin Receptor," *Science*, 254:1022–1024, (Nov. 15, 1991).

Marie et al., "Characterization of Glucagon Receptors in Pancreatic β and Liver Cells with a Biotinyl–ε–Aminocaproylated Glucagon Probe," *Biomed. Res.* 13:181–187 (1992).

Thorens, "Expression Cloning of the Pancreatic β cell Receptor for the Gluco–Incretin Hormone Glucagon–like Peptide 1," *Proc. Natl. Acad. Sci. USA*, 89:8641–8646 (Sep., 1992).

Jelinek et al., "Expression Cloning and Signaling Properties of the Rat Glucagon Receptor," *Science*, 259:1614–1616 (Mar. 12, 1993).

FIG. 5A

| | | | | | | | | | | | | | | |
|---|---|---|---|---|---|---|---|---|---|---|---|---|---|---|
| Met | Leu | Leu | Thr | Gln | Leu | His | Cys | Pro | Tyr | Leu | Leu | Leu | Leu | Val |
| 1 | | | | 5 | | | | | 10 | | | | | 15 |

| | | | | | | | | | | | | | | |
|---|---|---|---|---|---|---|---|---|---|---|---|---|---|---|
| Val | Leu | Ser | Cys | Leu | Pro | Lys | Ala | Pro | Ser | Ala | Gln | Val | Met | Asp | Phe |
| | | | 20 | | | | | 25 | | | | | 30 | |

Leu Phe Glu Lys Trp Lys Leu Tyr Ser Asp Gln Cys His His Asn Leu
　　　　35　　　　　　　　　40　　　　　　　　　45

Ser Leu Leu Pro Pro Pro Thr Glu Leu Val Cys Asn Arg Thr Phe Asp
　50　　　　　　　　　55　　　　　　　　　60

Lys Tyr Ser Cys Trp Pro Asp Thr Pro Pro Asn Thr Thr Ala Asn Ile
　65　　　　　　　　　70　　　　　　　75　　　　　　　　　　80

Ser Cys Pro Trp Tyr Leu Pro Trp Tyr His Lys Val Gln His Arg Leu
　　　　　　　85　　　　　　　　　90　　　　　　　　　95

Val Phe Lys Arg Cys Gly Pro Asp Gly Gln Trp Val Arg Gly Pro Arg
　　　　　100　　　　　　　　105　　　　　　　110

Gly Gln Ser Trp Arg Asp Ala Ser Gln Cys Gln Met Asp Asp Asp Glu
　　　115　　　　　　　　　120　　　　　　　　125

Ile Glu Val Gln Lys Gly Val Ala Lys Met Tyr Ser Ser Tyr Gln Val
　　130　　　　　　　　　135　　　　　　　　　140

Met Tyr Thr Val Gly Tyr Ser Leu Ser Leu Gly Ala Leu Leu Leu Ala
145　　　　　　　　150　　　　　　　　155　　　　　　　　160

Leu Val Ile Leu Leu Gly Leu Arg Lys Leu His Cys Thr Arg Asn Tyr
　　　　　　　165　　　　　　　　170　　　　　　　　175

Ile His Gly Asn Leu Phe Ala Ser Phe Val Leu Lys Ala Gly Ser Val
　　　　　180　　　　　　　　　185　　　　　　　　190

```
Leu Val Ile Asp Trp Leu Leu Lys Thr Arg Tyr Ser Gln Lys Ile Gly
            195                 200                 205

Asp Asp Leu Ser Val Ser Val Trp Leu Ser Asp Gly Ala Val Ala Gly
            210                 215                 220

Cys Arg Val Ala Thr Val Ile Met Gln Tyr Gly Ile Ile Ala Asn Tyr
225                 230                 235                 240

Cys Trp Leu Leu Val Glu Gly Val Tyr Leu Tyr Ser Leu Leu Ser Ile
                245                 250                 255

Thr Thr Phe Ser Glu Lys Ser Phe Phe Ser Leu Tyr Leu Cys Ile Gly
            260                 265                 270

Trp Gly Ser Pro Leu Leu Phe Val Ile Pro Trp Val Val Val Lys Cys
            275                 280                 285

Leu Phe Glu Asn Val Gln Cys Trp Thr Ser Asn Asp Asn Met Gly Phe
            290                 295                 300

Trp Trp Ile Leu Arg Ile Pro Val Leu Leu Ala Ile Leu Ile Asn Phe
305                 310                 315                 320

Phe Ile Phe Val Arg Ile Ile His Leu Leu Val Ala Lys Leu Arg Ala
                325                 330                 335

His Gln Met His Tyr Ala Asp Tyr Lys Phe Arg Leu Ala Arg Ser Thr
            340                 345                 350

Leu Thr Leu Ile Pro Leu Leu Gly Val His Glu Val Val Phe Ala Phe
            355                 360                 365

Val Thr Asp Glu His Ala Gln Gly Thr Leu Arg Ser Thr Lys Leu Phe
            370                 375                 380

Phe Asp Leu Phe Phe Ser Ser Phe Gln Gly Leu Leu Val Ala Val Leu
385                 390                 395                 400
```

*FIG. 5B*

Tyr Cys Phe Leu Asn Lys Glu Val Gln Ala Glu Leu Leu Arg Arg Trp
                405                 410                 415

Arg Arg Trp Gln Glu Gly Lys Ala Leu Gln Glu Glu Arg Met Ala Ser
                420                 425                 430

Ser His Gly Ser His Met Ala Pro Ala Gly Thr Cys His Gly Asp Pro
                435                 440                 445

Cys Glu Lys Leu Gln Leu Met Ser Ala Gly Ser Ser Ser Gly Thr Gly
        450                 455                 460

Cys Glu Pro Ser Ala Lys Thr Ser Leu Ala Ser Ser Leu Pro Arg Leu
465                 470                 475                 480

Ala Asp Ser Pro Thr
                485

FIG. 5C

GLUCAGON RECEPTOR PROTEINS, PEPTIDES, AND ANTIBODIES

This application is a divisional of Ser. No. 08/086,631, filed Jul.1, 1993 (pending), which is a continuation-in-part of Ser. No. 07/938,331, filed Aug. 28, 1992, (abandoned), which are incorporated herein by reference.

TECHNICAL FIELD

The present invention relates generally to cell surface receptors, and more specifically, to glucagon receptors.

BACKGROUND OF THE INVENTION

Glucagon is a 29 amino acid hormone produced by the alpha cells of pancreatic islets. Glucagon is responsible for the maintenance of normal levels of glucose in many animals, including humans, by acting as an insulin-counteracting hormone. In particular, while insulin is known to rapidly decrease blood glucose levels, glucagon counterbalances these effects by contributing to the elevation of blood glucose levels.

The interactions of glucagon and insulin are very important to the maintenance of glucose levels within the body. An imbalance of glucagon or insulin is believed to play a role in several diseases, such as diabetes mellitus and diabetic ketoacidosis. According to one theory, the hyperglycemic state of diabetes mellitus may be brought on not only by glucose under-utilization (due to decreased insulin), but also by the overproduction of glucose due to elevated concentrations of glucagon (see, Unger, "Diabetes and the alpha cell," *Diabetes* 25:136–151, 1976; Unger and Orci, "The essential role of glucagon in the pathogenesis of diabetes mellitus," *Lancet* 1:14–16, 1975).

An important factor in the study of glucagon, and glucagon's role in diseases such as diabetes mellitus, is the glucagon receptor, which, upon binding with glucagon, transduces a signal to the cell, thereby triggering glycogenolysis (glycogen hydrolysis), and gluconeogenesis (glucose synthesis).

It is presently believed that glucagon's effects are mediated in part by the elevation of the intracellular levels of cyclic adenosine monophosphate (cAMP). In particular, the binding of glucagon to its cellular receptor activates adenylate cyclase to produce cAMP, thus raising the levels of intracellular cAMP. This elevation of intracellular levels of cAMP is believed to result in glycogenolysis and gluconeogenesis, with the resultant rise in glucose production by the liver (see, Unson et al., "Biological Activities of des-His$^1$[Glu$^9$] Glucagon Amide, a Glucagon Antagonist," *Peptides* 10:1171–1177, 1989).

Additional pathways, however, have also been suggested for the stimulation of glycogenolysis and gluconeogenesis. In particular, it has been reported that glucagon binds to receptors in the hepatocyte membrane that are coupled via a G-protein to phospholipase C. Upon stimulation, this protein causes the breakdown of phosphatidylinositol 4,5 biphosphate to produce the second messengers inositol triphospate and 1,2 diacylglycerol (see, Wakelam et al., "Activation of two signal-transduction systems in hepatocytes by glucagon," *Nature* 323:68–71, 1986; Unson et al., *Peptides* 10:1171–1177, 1989; and Pittner and Fain, *Biochem. J.* 277:371–378, 1991). The stimulation by glucagon of inositol phospholipid metabolism may be an additional pathway whereby glucagon can stimulate glycogenolysis and gluconeogenesis.

The present invention discloses glucagon receptor(s), and further provides other related advantages.

SUMMARY OF THE INVENTION

Within one aspect of the present invention, isolated DNA molecules are provided encoding a glucagon receptor. The term "isolated DNA molecule" as used herein refers to DNA molecules or sequences which are separate, are placed apart and alone, or are separated from other components. For example, a DNA molecule is isolated when it is separated from other DNA molecules including other chromosomal sequences with which it is naturally associated in the genome and, in particular, free of other structural genes. An isolated DNA molecule may include 5' and 3' untranslated sequences with which it is naturally associated. Within one embodiment of the invention, the glucagon receptor is selected from the group consisting of rat and human glucagon receptors. Within another embodiment, the DNA molecule comprises the sequence of nucleotides of SEQ ID NO: 14, from nucleotide 145 to nucleotide 1599. Within another embodiment, the DNA molecule encodes a glucagon receptor comprising the sequence of amino acids of SEQ ID NO: 15, from methionine, amino acid number 1, to threonine, amino acid number 485. Within another embodiment, the DNA molecule comprises the sequence of nucleotides of SEQ ID NO: 24, from nucleotide 53 to nucleotide 1486. Within yet another embodiment, the DNA molecule encodes a glucagon receptor comprising the sequence of amino acids of SEQ ID NO: 25, from methionine, amino acid number 1, to phenylalanine, amino acid number 477. Also provided are DNA constructs comprising a first DNA segment encoding a glucagon receptor operably linked to additional DNA segments necessary for the expression of the first DNA segment, host cells containing such DNA constructs, as well as methods for producing a glucagon receptor comprising the step of culturing a host cell under conditions promoting expression of a DNA segment encoding a glucagon receptor.

Within another aspect of the invention, isolated glucagon receptor peptides are provided. Within one embodiment, an isolated glucagon receptor peptide is provided comprising the sequence of nucleotides of SEQ ID NO: 15, from glutamine, amino acid number 28, to tyrosine, amino acid number 142.

Within another aspect of the invention, isolated antibodies are provided which specifically bind to glucagon receptors. Within one embodiment, the antibody is a monoclonal antibody. Within an additional embodiment, a monoclonal antibody is provided which is capable of blocking the binding of glucagon to a glucagon receptor. Also provided are hybridomas which produce the above-described monoclonal antibodies.

Within yet another aspect of the present invention, a method for detecting the presence of glucagon antagonists is provided, comprising the steps of (a) exposing a compound in the presence of a glucagon agonist to a recombinant glucagon receptor coupled to a response pathway under conditions and for a time sufficient to allow binding of the compound to the receptor and an associated response through the pathway, and (b) detecting a reduction in the stimulation of the response pathway resulting from the binding of the compound to the glucagon receptor, relative to the stimulation of the response pathway by the glucagon agonist alone and therefrom determining the presence of a glucagon antagonist.

Within various embodiments of the invention, the response pathway is a membrane-bound adenylate cyclase response pathway and the step of detecting comprises measuring a reduction in cyclic AMP production by the membrane-bound adenylate cyclase response pathway.

Within another embodiment of the invention, the response pathway includes a luciferase reporter system.

Within yet another aspect of the present invention, probes are provided of at least 12 nucleotides, the probe being capable of hybridizing with nucleic acids which encode a glucagon receptor.

These and other aspects of the present invention will become evident upon reference to the following detailed description and attached drawings. In addition, various references are set forth below which describe in more detail certain procedures or compositions (e. g., plasmids, etc.), and are therefore incorporated by reference in their entirety.

BRIEF DESCRIPTION OF THE DRAWINGS

FIGS. 5A–C collectively show the amino acid sequence of a rat glucagon receptor with the transmembrane domains overlined.

DETAILED DESCRIPTION OF THE INVENTION

Figure 1:
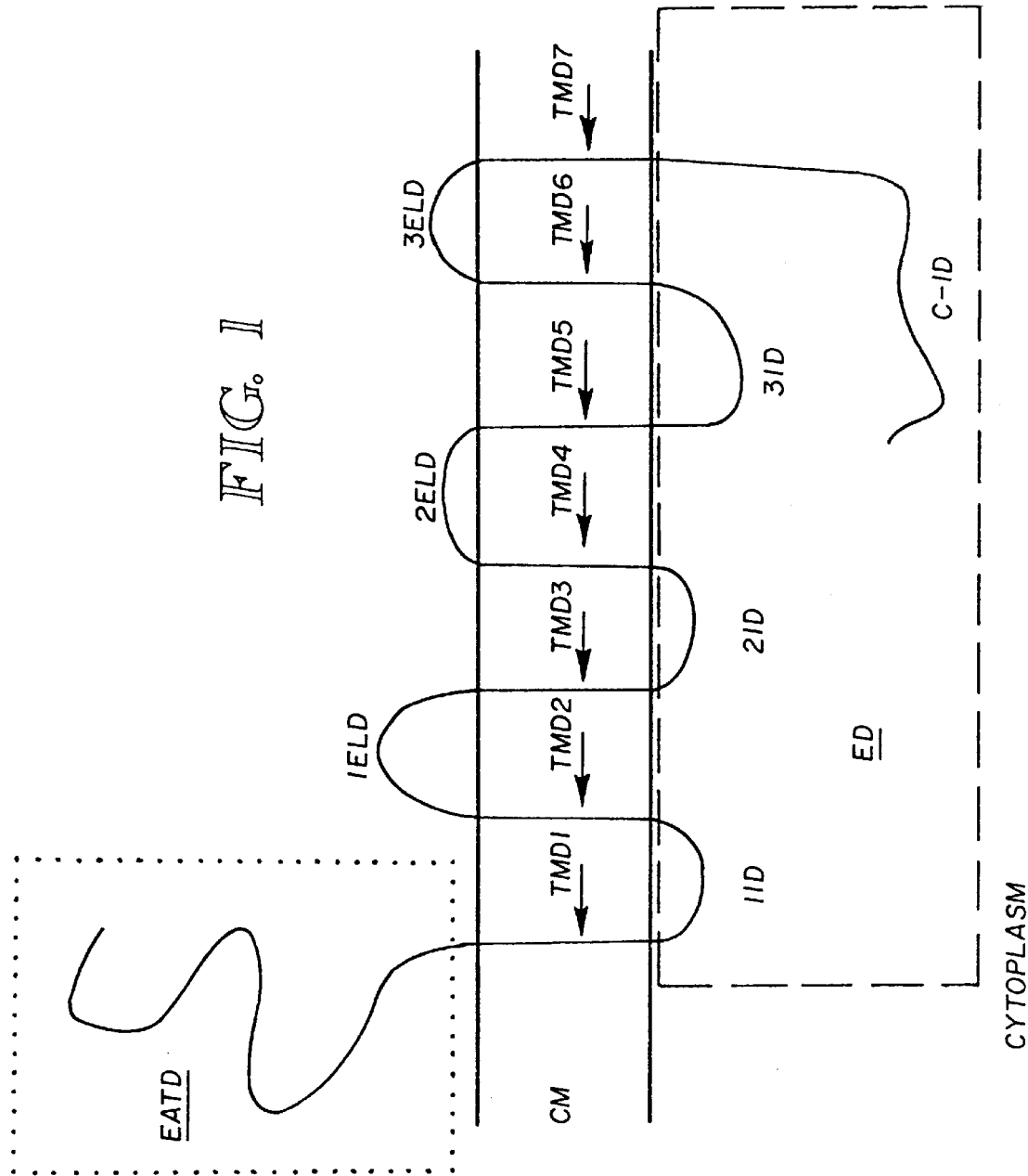
FIG. 1 illustrates the structure of a representative glucagon receptor. Symbols used are EATD (extracellular amino-terminal domain), which is encircled by the dotted line; CM (cellular membrane); ED (effector domain), which is encircled by the dashed line; 1ID, the first intracellular loop domain; 2ID, the second intracellular loop domain; 3ID, the third intracellular loop domain; C-ID, the carboxy-terminal intracellular domain; 1ELD, the first extracellular loop domain; 2ELD, the second extracellular loop domain; 3ELD, the third extracellular loop domain; TMD1, the first transmembrane domain; TMD2, the second transmembrane domain; TMD3, the third transmembrane domain; TMD4, the fourth transmembrane domain; TMD5, the fifth transmembrane domain; TMD6, the sixth transmembrane domain; and TMD7, the seventh transmembrane domain.

As noted above, the present invention provides isolated DNA molecules which encode glucagon receptors. In their native configuration, glucagon receptors are believed to exist as membrane bound proteins, consisting of an extracellular amino terminal domain as well as several smaller external and internal domains (see FIG. 1). Within the context of the present invention, "glucagon receptor" refers to such proteins and substantially similar derivatives. Derivatives include allelic variants and genetically engineered variants that contain conservative amino acid substitutions and/or minor additions, substitutions or deletions of amino acids. Glucagon receptors of the present invention are capable of binding glucagon and transducing the signal provided by glucagon to a cell. Preferably, glucagon receptors of the present invention are capable of binding glucagon with a Kd of 100 nm or less, more preferably, 50 nM or less, and most preferably, 33 nM or less. Representative assays which may be utilized to determine glucagon binding by a glucagon receptor are described in more detail below in Examples 3 and 6.

Signal transduction typically occurs when a response pathway is activated by an external stimulus that is generally, but not always, directly coupled to a membrane-bound receptor. Response pathways generally induce cellular responses such as extracellular matrix secretion from responsive cell lines, hormone secretion, chemotaxis, differentiation, or the initiation or inhibition of cell division of responsive cells. As used herein the coupling of receptors to response pathways refers to the direct activation of a response pathway or the transduction of a signal via a second messenger, such as a G-protein, to activate a cellular response pathway.

A variety of cellular response pathways may be utilized by glucagon receptors to transduce a glucagon binding signal to the cell, including for example, the adenylate cyclase response pathway, and an intracellular calcium response pathway. Assays to determine adenylate cyclase activity are well known in the art, and include, for example, those described by Lin et al. (*Biochemistry* 14:1559–1563, 1975). The present invention also provides for the measurement of biological activity of a glucagon receptor based on intracellular calcium concentrations (see Grynkiewicz et al., *J. Biol. Chem.* 260:3440–3450, 1985), as well as through the use of a luciferase reporter system which is described in greater detail below. In addition, biological responses which occur via the inositol triphosphate pathway may be assessed by measuring inositol phosphate metabolism as generally described in Subers and Nathanson (*J. Mol. Cell. Cardiol.* 20:131–140, 1988) or Pittner and Fain (*Biochem. J.* 277:371–378, 1991). It should be noted that, within the context of the present invention, not all response pathways need necessarily be present in order for the glucagon receptor to transduce a signal to a cell. For example, certain cellular responses, such as an increase in intracellular calcium levels, may also be triggered by the binding of glucagon to its receptor in the absence of cAMP or inositol phosphate signals.

ISOLATION OF GLUCAGONRECEPTOR cDNA CLONES

As noted above, the present invention provides isolated DNA molecules which encode glucagon receptors. Briefly, genomic or CDNA molecules encoding glucagon receptors may be obtained from libraries which have been prepared from cells and tissues according to procedures such as those described below and in the Examples. Cells and tissues which may be utilized within the present invention can be obtained from a variety of mammals including, for example, humans, macaques, cattle, pigs, horses, dogs, rats, and mice. Preferred cells and tissues which may be utilized include adipose, kidney, pancreas, heart, and liver.

Within one aspect of the invention, a rat glucagon receptor may be isolated and cloned utilizing procedures described herein. Briefly, poly(A)⁺RNA was isolated from Sprague Dawley rats, and used as a template for cDNA synthesis essentially as described by Houamed et al. (*Science* 252:1318–1321, 1991) in order to generate full length cDNAs. A library containing approximately 1×10⁶ clones was then constructed in a mammalian cell expression plasmid by the directional cloning of cDNAs greater than 800 bp. Plasmid DNAs prepared from pools containing 5,000 clones each were then transfected into COS-7 cells, selected, and grown on microscope slides. The transfected cells were analyzed after 72 hours by binding with $^{125}$I-glucagon, followed by emulsion radiography (McMahan et al., *EMBO J.* 10:2821–2832, 1991). Positive pools were successively broken down until a single clone was isolated. The plasmid obtained from this clone, designated pLJ4, contains an approximately 2.0 kilobase insert which encodes a 485 amino acid protein with a predicted molecular weight of 54,962 daltons (see SEQ ID NO: 15).

Within other aspects of the present invention, methods are provided for isolating and cloning a human glucagon receptor. A variety of techniques may be utilized given the disclosure provided herein, including, for example, the use of Polymerase Chain Reaction ("PCR") to amplify sequences which encode a glucagon receptor (Example 4), which may then be used in the identification of libraries that contain sequences which encode a human glucagon receptor, followed by the cloning of the receptor (Example 5). Particularly preferred strategies for cloning of the human glucagon receptor are set forth below in Examples 4 and 5. Alternatively, an expression library containing human cDNAs may be prepared from suitable RNA sources essentially as described in Example 1 and screened as described in Example 3 for clones that express functional human glucagon receptors.

PRODUCTION OF RECOMBINANT GLUCAGON RECEPTORS

The present invention provides for the production of recombinant glucagon receptors by culturing host cells containing a DNA construct comprising a first DNA segment encoding a glucagon receptor operably linked to additional DNA segments necessary for the expression of the first DNA segment. As noted previously, within the context of the present invention "glucagon receptors" are understood to include derivatives thereof that are substantially similar. Moreover, glucagon receptors may be encoded by DNA sequences which are substantially similar to the DNA sequences disclosed herein. As used herein, a DNA sequence is deemed to be "substantially similar" if: (a) the DNA sequence is derived from the coding region of a native glucagon receptor gene (including, for example, allelic variations of the sequences disclosed below); (b) the DNA sequence is capable of hybridization to DNA sequences of the present invention under high or low stringency (see Sambrook et al., *Molecular Cloning: A Laboratory Manual*, 2d Ed., Cold Spring Harbor Laboratory Press, NY, 1989); or (c) DNA sequences are degenerate as a result of the genetic code to the DNA sequences defined in (a) or (b).

Mutations in nucleotide sequences constructed for expression of variant glucagon receptors will preserve the reading frame of the coding sequences. Furthermore, the mutations will preferably not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed glucagon receptor mutants screened for biological activity.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*Bio Techniques*, January 1985, 12–19); Smith et al. (*Genetic Engineering: Principles and Methods*, Plenum Press, 1981); and Sambrook et al. (supra).

The primary amino acid structure of a glucagon receptor may also be modified by forming covalent or aggregative conjugates with other chemical moieties, such as glycosyl groups, lipids, phosphate, acetyl groups, or with other proteins or polypeptides. Within a further embodiment, glucagon receptors may be fused with other peptides which facilitate purification or identification of glucagon receptors. For example, a glucagon receptor may be prepared as a fusion protein with the FLAG™ polypeptide sequence (see U. S. Pat. No. 4,851,341; see also Hopp et al., *Bio/Technology* 6:1204, 1988). The FLAG™ polypeptide sequence is highly antigenic and provides an epitope for binding by a specific monoclonal antibody, enabling rapid purification of the expressed recombinant protein. This sequence is also specifically cleaved by bovine mucosal enterokinase at the residue immediately following the Asp-Lys pairing.

Numerous DNA constructs, including all or part of the nucleotide sequences of a native or variant glucagon receptor as discussed above, may be prepared as a matter of convenience. Within the context of the present invention, a DNA construct is understood to refer to a DNA molecule, or a clone of such a molecule (either single- or double-stranded), that has been modified through human intervention to contain segments of DNA combined and juxtaposed in a manner that as a whole would not otherwise exist in nature.

DNA constructs of the present invention comprise a first DNA segment encoding a glucagon receptor operably linked to additional DNA segments required for the expression of the first DNA segment. Within the context of the present invention, additional DNA segments will generally include promoters and transcription terminators, and may further include enhancers and other elements.

DNA constructs, also known as expression vectors, may also contain DNA segments necessary to direct the secretion of a polypeptide of interest. Such DNA segments may include at least one secretory signal sequence. Preferred secretory signals include the glucagon secretory signal (pre-pro sequence), the alpha factor signal sequence (pre-pro sequence; Kurjan and Herskowitz, *Cell* 30:933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3:439–447, 1983), the α-1-antitrypsin signal sequence (Kurachi et al., *Proc. Natl Acad. Sci. USA* 78:6826–6830, 1981), the α-2 plasmin inhibitor signal sequence (Tone et al., *J. Biochem.* (Tokyo) 102:1033–1042, 1987), the tissue plasminogen activator signal sequence (Pennica et al., *Nature* 301:214–221, 1983), the *E. coli* PhoA signal sequence (Yuan et al., *J. Biol. Chem.* 265:13528–13552, 1990) or any of the bacterial signal sequences reviewed, for example, by Oliver (*Ann. Rev. Microbiol.* 39:615–649, 1985). Alternatively, a secretory signal sequence may be synthesized according to the rules established, for example, by von Heinje (*Eur. J. Biochem.* 133:17–21, 1983; *J. Mol BioL* 184:99–105, 1985; *Nuc. Acids Res.* 14:4683–4690, 1986).

Secretory signal sequences may be used singly or may be combined. For example, a first secretory signal sequence may be used in combination with a sequence encoding the third domain of Barrier (described in U.S. Pat. No. 5,037,243, which is incorporated by reference herein in its entirety). A sequence encoding the third domain of Barrier may be positioned in proper reading frame 3' of the DNA sequence of interest or 5' to the DNA segment and in proper reading frame with both the secretory signal sequence and the DNA segment of interest.

For expression, a DNA molecule encoding a glucagon receptor is inserted into a suitable DNA construct, which in turn is used to transform or transfect appropriate host cells for expression. Host cells for use in practicing the present invention include mammalian, avian, plant, insect, bacterial and fungal cells. Preferred eukaryotic cells include cultured mammalian cell lines (e. g., rodent or human cell lines) and fungal cells, including species of yeast (e. g., *Saccharomyces spp.*, particularly *S. cerevisiae, Schizosaccharomyces spp.*, or *Kluyveromyces spp.*) or filamentous fungi (e. g., *Aspergillus spp., Neurospora spp.*). Strains of the yeast *Saccharomyces cerevisiae* are particularly preferred. Methods for producing recombinant proteins in a variety of prokaryotic and eukaryotic host cells are generally known in the art (see, "Gene Expression Technology," *Methods in Enzymology*, Vol. 185, Goeddel (ed.), Academic Press, San Diego, Calif., 1990; see also, "Guide to Yeast Genetics and Molecular Biology," *Methods in Enzymology*, Guthrie and Fink (eds.) Academic Press, San Diego, Calif., 1991). In general, a host cell will be selected on the basis of its ability to produce the protein of interest at a high level or its ability to carry out at least some of the processing steps necessary for the biological activity of the protein. In this way, the number of cloned DNA sequences which must be transfected into the host cell may be minimized and overall yield of biologically active protein may be maximized.

Suitable yeast vectors for use in the present invention include YRp7 (Struhl et al., Proc. *Natl. Acad. Sci. USA* 76:1035–1039, 1978), YEp13 (Broach et al., *Gene* 8:121–133, 1979), POT vectors (Kawasaki et al., U.S. Pat. No. 4,931,373, which is incorporated by reference herein), pJDB249 and pJDB219 (Beggs, *Nature* 275:104–108, 1978) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8:17, 1979), HIS3 (Struhl et al., ibid.) orPOTI (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., *J. Biol. Chem.* 255:12073–12080, 1980; Alber and Kawasaki, *J Mol. AppL Genet.* 1:419–434, 1982; Kawasaki, U.S. Pat. No. 4,599, 311) or alcohol dehydrogenase genes (Young et al., in *Genetic Engineering of Microorganisms for Chemicals*, Hollaender et al. (eds.), p.355, Plenum, N.Y., 1982; Ammerer, *Meth. Enzymol.* 101:192–201, 1983). In this regard, particularly preferred promoters are the TPI1 promoter (Kawasaki, U.S. Pat. No. 4,599,311, 1986) and the ADH2–4$^c$ promoter (Russell et al., *Nature* 304:652–654, 1983; Irani and Kilgore, U.S. patent application Ser. No. 07/784,653, now abandoned, which is incorporated herein by reference). The expression units may also include a transcriptional terminator. A preferred transcriptional terminator is the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4:2093–2099, 1985) and the tpiA promoter. An example of a suitable terminator is the ADH3 terminator (McKnight et al., ibid., 1985). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell will generally contain a genetic defect that is complemented by the selectable marker present on the expression vector. Choice of a particular host and selectable marker is well within the level of ordinary skill in the art. To optimize production of the heterologous proteins in yeast, for example, it is preferred that the host strain carries a mutation, such as the yeast pep4 mutation (Jones, *Genetics* 85:23–33, 1977), which results in reduced proteolytic activity.

In addition to fungal cells, cultured mammalian cells may be used as host cells within the present invention. Preferred cultured mammalian cells for use in the present invention include the COS-1 (ATCC No. CRL 1650), COS-7 (ATCC No. CRL 1651), BHK (ATCC No. CRL 1632), and 293 (ATCC No. CRL 1573; Graham et al., *J. Gen. Virol.* 36:59–72, 1977) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT$_2$B (Orskov and Nielson, *FEBS* 229(1):175–178, 1988).

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-1 promoter (Palmiter et al., U.S. Pat. No. 4,579,821), a mouse V$_K$ promoter (Bergman et al., *Proc. Natl. Acad. Sci. USA* 81:7041–7045, 1983; Grant et al., *Nuc. Acids Res.* 15:5496, 1987) and a mouse V$_H$ promoter (Loh et al., *Cell* 33:85–93, 1983). A particularly preferred promoter is the major late promoter from Adenovirus 2 (Kaufman and Sharp, *Mol. Cell. Biol.* 2:1304–13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse $\mu$ enhancer (Gillies, *Cell* 33:717–728, 1983). Expression vectors may also include sequences encoding the adenovirus VA RNAs. Suitable vectors can be obtained from commercial sources (e. g., Stratagene, La Jolla, Calif).

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., NY, 1987), which are incorporated herein by reference. To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate vector at the same time as the glucagon receptor sequence, or they may be introduced on the same vector. If on the same vector, the selectable marker and the glucagon receptor sequence may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells which satisfy these criteria may then be cloned and scaled up for production.

Preferred prokaryotic host cells for use in carrying out the present invention are strains of the bacteria *Escherichia coli*, although Bacillus and other genera are also useful. Techniques for transforming these hosts and expressing foreign DNA sequences cloned therein are well known in the art (see, e. g., Maniatis et al., *Molecular Cloning: A Laboratory Manual*, Cold Spring Harbor Laboratory, 1982, which is incorporated herein by reference; or Sambrook et al., supra). Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage λ (Queen, *J. Mol. Appl Genet.* 2:1–10, 1983) promoter systems. Plasmids useful for transforming bacteria include pBR322 (Bolivar et al., *Gene* 2:95–113, 1977), the pUC plasmids (Messing, *Meth. Enzymol.* 101:20–78, 1983; Vieira and Messing, *Gene* 19:259–268, 1982), pCQV2 (Queen, ibid.), and derivatives thereof. Plasmids may contain both viral and bacterial elements.

Given the teachings provided herein, promoters, terminators and methods for introducing expression vectors encoding glucagon receptors of the present invention into plant, avian and insect cells would be evident to those of skill in the art. The use of baculoviruses, for example, as vectors for expressing heterologous DNA sequences in insect cells has been reviewed by Atkinson et al. (*Pestic. Sci.* 28:215–224, 1990). In addition, the use of *Agrobacterium rhizogenes* as vectors for expressing genes in plant cells has been reviewed by Sinkar et al. (*J. Biosci.* (*Bangalore*) 11:47–58, 1987).

Host cells containing DNA constructs of the present invention are then cultured to express a DNA segment encoding a glucagon receptor. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Suitable growth conditions for yeast cells, for example, include culturing in a chemically defined medium, comprising a nitrogen source, which may be a non-amino acid nitrogen source or a yeast extract, inorganic salts, vitamins and essential amino acid supplements at a temperature between 4° C. and 37° C., with 30° C. being particularly preferred. The pH of the medium is preferably maintained at a pH greater than 2 and less than 8, more preferably pH 5–6. Methods for maintaining a stable pH include buffering and constant pH control. Preferred agents for pH control include sodium hydroxide. Preferred buffering agents include succinic acid and Bis-Tris (Sigma Chemical Co., St. Louis, Mo.). Due to the tendency of yeast host cells to hyperglycosylate heterologous proteins, it may be preferable to express the glucagon receptors of the present invention in yeast cells having a defect in a gene required for asparagine-linked glycosylation. Such cells are preferably grown in a medium containing an osmotic stabilizer. A preferred osmotic stabilizer is sorbitol supplemented into the medium at a concentration between 0.1M and 1.5M, preferably at 0.5M or 1.0M. Cultured mammalian cells are generally cultured in commercially available serum-containing or serum-free media. Selection of a medium and growth conditions appropriate for the particular cell line used is within the level of ordinary skill in the art.

Glucagon receptors may also be expressed in non-human transgenic animals, particularly transgenic warm-blooded animals. Methods for producing transgenic animals, including mice, rats, rabbits, sheep and pigs, are known in the art and are disclosed, for example, by Hammer et al. (*Nature* 315:680–683, 1985), Palmiter et al. (*Science* 222:809–814, 1983), Brinster et al. (*Proc. Natl Acad. Sci. USA* 82:4438–4442, 1985), Palmiter and Brinster (*Cell* 41:343–345, 1985) and U.S. Pat. No. 4,736,866, which are incorporated herein by reference. Briefly, an expression unit, including a DNA sequence to be expressed together with appropriately positioned expression control sequences, is introduced into pronuclei of fertilized eggs. Introduction of DNA is commonly done by microinjection. Integration of the injected DNA is detected by blot analysis of DNA from tissue samples, typically samples of tail tissue. It is generally preferred that the introduced DNA be incorporated into the germ line of the animal so that it is passed on to the animal's progeny.

Within a preferred embodiment of the invention, a transgenic animal, such as a mouse, is developed by targeting a mutation to disrupt a glucagon receptor sequence (see, Mansour et al., "Disruption of the proto-oncogene int-2 in mouse embyro-derived stem cells: a general strategy for targeting mutations to non-selectable genes," *Nature* 336:348–352, 1988). Such animals may readily be utilized as a model to study the role of the glucagon receptor in metabolism.

GLUCAGON RECEPTOR PEPTIDES

As noted above, the present invention also provides glucagon receptor peptides. Within the context of the present invention, glucagon receptor peptides are understood to include portions of a glucagon receptor or derivatives thereof discussed above, which do not contain transmembrane domains, and are at least 10 amino acids in length. Briefly, the structure of the glucagon receptor as well as putative transmembrane domains may be predicted from the primary translation products using the hydrophopicity plot function of, for example, P/C Gene or Intelligenetics Suite (Intelligenetics, Mt. View, Calif.), or according to the methods described by Kyte and Doolittle (*J. Mol. Biol.* 157:105–132, 1982). The hydrophopicity plot of a rat glucagon receptor is graphically depicted in FIG. 2. While not wishing to be bound by a graphical representation, based upon this hydrophopicity analysis, glucagon receptors are believed to have the general structure shown in FIG. 1. In particular, these receptors are believed to comprise an extracellular amino-terminal domain, three extracellular loop domains and four intracellular loop domains each separated by a transmembrane domain.

Within one aspect of the invention, an isolated glucagon receptor peptide is provided comprising the extracellular amino-terminal domain of a glucagon receptor. Within a preferred embodiment, an isolated glucagon receptor peptide is provided comprising the sequence of amino acids of SEQ ID NO: 15, from glutamine, amino acid number 28, to tyrosine, amino acid number 142. Also provided are other isolated glucagon receptor peptides which may be selected from the extracellular and intracellular loop domains of the glucagon receptor. (see FIGS. 1 and 5) Within one embodiment, glucagon receptor peptides are selected from the group consisting of 1ID (SEQ ID NO: 15, from lysine, amino acid number 169, to histidine, amino acid number 178), 1ELD (SEQ ID NO: 15, from tyrosine, amino acid number 203, to isoleucine, amino acid number 231), 2ID (SEQ ID NO: 15, from phenylalanine, amino acid number 259, to serine, amino acid number 266), 2ELD (SEQ ID NO: 15, from valine, amino acid number 293, to isoleucine, amino acid number 307), 3ID (SEQ ID NO: 15, from leucine, amino acid number 334, to lysine, amino acid number 345), and 3ELD (SEQ ID NO: 15, from aspartic acid, amino acid number 371, to serine, amino acid number 380).

Glucagon receptor peptides of the present invention may be produced utilizing recombinant techniques as discussed above, or by synthetic methods, and may be additionally purified as described below.

PURIFICATION OF GLUCAGON RECEPTOR PEPIDES

Isolated glucagon receptor peptides may be prepared by, among other methods, culturing suitable host/vector systems to produce the recombinant translation products of the present invention. Supernatants from such cell lines may then be treated by a variety of purification procedures in order to isolate the glucagon receptor peptide. For example, the supernatant may be first concentrated using commercially available protein concentration filters, such as an Amicon or Millipore Pellicon ultrafiltration unit. Following concentration, the concentrate may be applied to a suitable purification matrix such as, for example, glucagon or an anti-glucagon receptor antibody bound to a suitable support. Alternatively, anion or cation exchange resins may be employed in order to purify the receptor or peptide. Finally, one or more reversed-phase high performance liquid chromatography (RP-HPLC) steps may be employed to further purify the glucagon receptor peptide.

A glucagon receptor peptide is deemed to be "isolated" or purified within the context of the present invention if only a single band is detected subsequent to SDS-polyacrylamide gel analysis followed by staining with Coomassie Brilliant Blue.

ANTIBODIES TO GLUCAGON RECEPTORS

Within one aspect of the present invention, glucagon receptors, including derivatives thereof, as well as portions or fragments of these proteins such as the glucagon receptor peptides discussed above, may be utilized to prepare antibodies which specifically bind to glucagon receptors. Within the context of the present invention the term "antibodies" includes polyclonal antibodies, monoclonal antibodies, fragments thereof such as F(ab')$_2$ and Fab fragments, as well as recombinantly produced binding partners. These binding partners incorporate the variable regions from a gene which encodes a specifically binding monoclonal antibody. Antibodies are defined to be specifically binding if they bind to the glucagon receptor with a $K_a$ of greater than or equal to $10^7$ $M^{-1}$. The affinity of a monoclonal antibody or binding partner may be readily determined by one of ordinary skill in the art (see, Scatchard, *Ann. N.Y. Acad. Sci.* 51:660–672, 1949).

Polyclonal antibodies may be readily generated by one of ordinary skill in the art from a variety of warm-blooded animals such as horses, cows, goats, sheep, dogs, chickens, rabbits, mice, or rats. Briefly, the glucagon receptor is utilized to immunize the animal through intraperitoneal, intramuscular, intraocular, or subcutaneous injections. The immunogenicity of a glucagon receptor or glucagon receptor peptide may be increased through the use of an adjuvant such as Freund's complete or incomplete adjuvant. Following several booster immunizations, small samples of serum are collected and tested for reactivity to the glucagon receptor. A variety of assays may be utilized in order to detect antibodies which specifically bind to a glucagon receptor. Exemplary assays are described in detail in *Antibodies: A Laboratory Manual*, Harlow and Lane (eds.), Cold Spring Harbor Laboratory Press, 1988. Representative examples of such assays include: Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos.

4,376,110 and 4,486,530; see also *Antibodies: A Laboratory Manual*, supra). Particularly preferred polyclonal antisera will give a signal that is at least three times greater than background. Once the titer of the animal has reached a plateau in terms of its reactivity to the glucagon receptor, larger quantities of polyclonal antisera may be readily obtained either by weekly bleedings, or by exsanguinating the animal.

Monoclonal antibodies may also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, within one embodiment a subject animal such as a rat or mouse is injected with a form of glucagon receptor suitable for generating an immune response against the glucagon receptor. Representative examples of suitable forms include, among others, cells which express the glucagon receptor, or peptides which are based upon the glucagon receptor sequence. Additionally, many techniques are known in the art for increasing the resultant immune response, for example by coupling the receptor or receptor peptides to another protein such as ovalbumin or keyhole limpet hemocyanin (KLH), or through the use of adjuvants such as Freund's complete or incomplete adjuvant. The initial immunization may be through intraperitoneal, intramuscular, intraocular, or subcutaneous routes.

Between one and three weeks after the initial immunization the animal may be reimmunized with another booster immunization. The animal may then be test bled and the serum tested for binding to the glucagon receptor using assays as described above. Additional immunizations may also be accomplished until the animal has plateaued in its reactivity to the glucagon receptor. The animal may then be given a final boost of glucagon receptor or glucagon receptor peptide, and three to four days later sacrificed. At this time, the spleen and lymph nodes may be harvested and disrupted into a single cell suspension by passing the organs through a mesh screen or by rupturing the spleen or lymph node membranes which encapsidate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the glucagon receptor that is suitable for generating an immune response as described above. Subsequently, the lymphocytes are harvested and fused as described below.

Cells which are obtained through the use of in vitro immunization or from an immunized animal as described above may be immortalized by transfection with a virus such as the Epstein-Barr virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas*, 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63-Ag 8.653 (ATCC No. CRL 1580), which may be utilized for fusions with either mouse, rat, or human cell lines. Fusion between the myeloma cell line and the cells from the immunized animal may be accomplished by a variety of methods, including the use of polyethylene glycol (PEG) (see *Antibodies: A Laboratory Manual*, Harlow and Lane (eds.), Cold Spring Harbor Laboratory Press, 1988) or electrofusion (see Zimmerman and Vienken, *J. Membrane Biol* 67:165–182, 1982).

Following the fusion, the cells are placed into culture plates containing a suitable medium, such as RPMI 1640 or DMEM (Dulbecco's Modified Eagles Medium) (JRH Biosciences, Lenexa, Kans.). The medium may also contain additional ingredients, such as Fetal Bovine Serum (FBS, i. e., from Hyclone, Logan, Utah, or JRH Biosciences), thymocytes which were harvested from a baby animal of the same species as was used for immunization, or agar to solidify the medium. Additionally, the medium should contain a reagent which selectively allows for the growth of fused spleen and myeloma cells. Particularly preferred is the use of HAT (hypoxanthine, aminopterin, and thymidine) (Sigma Chemical Co., St. Louis, Mo.). After about seven days, the resulting fused cells or hybridomas may be screened in order to determine the presence of antibodies which recognize the glucagon receptor. Following several clonal dilutions and reassays, a hybridoma producing antibodies which bind to glucagon receptor may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escizerichia coli* for Generation of Monoclonal Catalytic Antibodies: Construction of a Heavy Chain Variable Region-Specific cDNA Library," *Proc. Natl. Acad Sci. USA* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990; these references describe a commercial system available from Stratacyte, La Jolla, Calif., which enables the production of antibodies through recombinant techniques). Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, binding partners may also be constructed utilizing recombinant DNA techniques to incorporate the variable regions of a gene which encodes a specifically binding antibody. The construction of these proteins may be readily accomplished by one of ordinary skill in the art (see, James W. Larrick et al., "Polymerase Chain Reaction Using Mixed Primers: Cloning of Human Monoclonal Antibody Variable Region Genes From Single Hybridoma Cells," *Biotechnology* 7:934–938, September 1989; Riechmrann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989; see also, U.S. Pat. No. 5,132,405 entitled "Biosynthetic Antibody Binding Sites"), given the disclosure provided herein. Briefly, within one embodiment, DNA segments encoding glucagon receptor-specific antigen binding domains are amplified from hybridomas which produce a specifically binding monoclonal antibody, and inserted directly into the genome of a cell which produces human antibodies (see Verhoeyen et al., supra; see also Reichmann et al., supra). This technique allows the antigen-binding site of a specifically binding mouse or rat monoclonal antibody to be transferred into a human antibody. Such antibodies are preferable for therapeutic use in humans because they are not as antigenic as rat or mouse antibodies.

Alternatively, the antigen-binding sites (variable region) may be either linked to, or inserted into, another completely different protein (see Chaudhary et al., supra), resulting in a new protein with antigen-binding sites of the antibody as well as the functional activity of the completely different protein. As one of ordinary skill in the art will recognize, the antigen-binding sites or glucagon receptor binding domain of the antibody may be found in the variable region of the antibody. Furthermore, DNA sequences which encode smaller portions of the antibody or variable regions which specifically bind to mammalian glucagon receptor may also be utilized within the context of the present invention. These portions may be readily tested for binding specificity to the glucagon receptor utilizing assays described below.

Within a preferred embodiment, genes which encode the variable region from a hybridoma producing a monoclonal antibody of interest are amplified using oligonucleotide primers for the variable region. These primers may be synthesized by one of ordinary skill in the art, or may be purchased from commercially available sources. Stratacyte (La Jolla, Calif.) sells primers for mouse and human variable regions including, among others, primers for $V_{H_a}$, $V_{H_b}$, $V_{H_c}$, $V_{H_d}$, $C_{H_1}$, $V_L$ and $C_L$ regions. These primers may be utilized to amplify heavy or light chain variable regions, which may then be inserted into vectors such as IMMUNOZAP*(H) or IMMUNOZAP*(L) (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426, 1988).

Within other embodiments, the binding partner is fused within the expression vector to another protein, such as a toxin. Cells which are bound by the binding partner may thus be killed by incorporation of the toxin (see Chaudhary et al., supra).

Once suitable antibodies or binding partners have been obtained, they may be isolated or purified by many techniques well known to those of ordinary skill in the art (see *Antibodies: A Laboratory Manual*, supra). Suitable techniques include peptide or protein affinity columns, HPLC or RP-HPLC, purification on protein A or protein G columns, or any combination of these techniques. Within the context of the present invention, the term "isolated" as used to define antibodies or binding partners means "substantially free of other blood components."

Antibodies and binding partners of the present invention have many uses. For example, antibodies may be utilized in flow cytometry to sort glucagon receptor-bearing cells, or to histochemically stain glucagon receptor-bearing tissues. Briefly, in order to detect glucagon receptors on cells, the cells are incubated with a labeled monoclonal antibody which specifically binds to glucagon receptors, followed by detection of the presence of bound antibody. These steps may also be accomplished with additional steps such as washings to remove unbound antibody. Labels suitable for use within the present invention are well known in the art including, among others, Flourescein Isothiocyanate (FITC), Phycoerythrin (PE), Horse Radish Peroxidase (HRP), and colloidal gold. Particularly preferred for use in flow cytometry is FITC which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; and Goding, "Conjugation of Antibodies with Fluorochromes: Modification to the Standard Methods," *J. Immunol. Methods* 13:215–226, 1970.) For histochemical staining, HRP, which is preferred, may be conjugated to the purified antibody according to the method of Nakane and Kawaoi ("Peroxidase-Labeled Antibody: A New Method of Conjugation," *J. Histochem. Cytochem.* 22:1084–1091, 1974; see also, Tijssen and Kurstak, "Highly Efficient and Simple Methods for Preparation of Peroxidase and Active Peroxidase Antibody Conjugates for Enzyme Immunoassays," *Anal. Biochem.* 136:451–457,1984).

In addition, purified antibodies or binding partners may also be utilized therapeutically to block the binding of glucagon to the glucagon receptor in vitro or in vivo. Briefly, blocking antibodies are those antibodies that bind to glucagon receptor epitopes in such a way as to prevent glucagon from binding to the receptor, or to prevent glucagon from effecting signal transduction. As noted above, a variety of assays may be utilized to detect antibodies which block or inhibit the binding of glucagon to the glucagon receptor, including inter alia, inhibition and competition assays noted above. Within one embodiment, monoclonal antibodies (prepared as described above) are assayed for binding to the glucagon receptor in the absence of glucagon, as well as in the presence of varying concentrations of glucagon. Blocking antibodies or binding partners are identified as those which, for example, bind to glucagon receptors and, in the presence of glucagon, block or inhibit the binding of glucagon to the glucagon receptor.

Antibodies or binding partners which are to be utilized therapeutically are preferably provided in a therapeutic composition comprising the antibody or binding partner and a physiologically acceptable carrier or diluent. Suitable carriers or diluents include, among others, neutral buffered saline or saline, and may also include additional excipients or stabilizers such as buffers, sugars such as glucose, sucrose, or dextrose, chelating agents such as EDTA, and various preservatives.

GLUCAGON ANTAGONISTS

As noted above, the present invention provides methods for detecting glucagon antagonists. Within the context of the present invention, an antagonist is understood to refer to a molecule that is capable of binding to a receptor, but which does not stimulate, or reduces the stimulation of, a response pathway within a cell. In particular, glucagon antagonists are generally identified by their ability to bind to the glucagon receptor, and thereby reduce the stimulation of a response pathway within a cell.

Within one aspect of the present invention, methods are provided for detecting the presence of glucagon antagonists comprising the steps of (a) exposing a compound in the presence of a glucagon agonist to a recombinant glucagon receptor coupled to a response pathway under conditions and for a time sufficient to allow binding of the compound to the receptor and an associated response through the pathway, and (b) detecting a reduction in the stimulation of the response pathway resulting from the binding of the compound to the glucagon receptor, relative to the stimulation of the response pathway by the glucagon agonist alone and therefrom determining the presence of a glucagon antagonist. Within the context of the present invention, glucagon agonists include molecules (including glucagon itself) capable of binding to a glucagon receptor, and which stimulate a response pathway within a cell.

A variety of compounds may be screened utilizing such methods. Representative examples include blocking antibodies discussed above, glucagon receptor peptides, and glucagon analogs (including both peptide and non-peptide ligands). U.S. patent application Ser. No. 07/741,931 (pending), for example, provides methods for producing large numbers of glucagon analogs using pools of DNA sequences encoding such analogs. Such pools of DNA sequences encoding glucagon analogs may be generated by saturation mutagenesis of DNA sequences encoding glucagon (e. g., Little, *Gene* 88:113–115, 1990; Hembers et al., *Gene* 88:143–151, 1989), by segment-directed mutagenesis (e. g., Shortle et al., *Proc. Natl. Acad. Sci. USA* 77:5375–5379, 1980), by forced nucleotide misincorporation (e. g., Liao and Wise *Gene* 88:107–111, 1990), or by use of randomly mutagenized oligonucleotides (Hutchison et al., *Proc. Natl. Acad. Sci. USA* 83:710–714, 1986). Individual transformants expressing a glucagon analog may then be cloned as discussed above, or pooled.

The compounds are exposed to a recombinant glucagon receptor in the presence of a glucagon agonist under conditions and for a time sufficient to allow binding of the compound to the receptor, and an associated response through the pathway. As utilized in the present invention, conditions and times sufficient for the binding of the glucagon antagonist to the receptor will vary with the source of the receptor, however, conditions suitable for the binding generally occur between 4° C. and 55° C. in a buffer solution between 0 and 2M NaCl, preferably between 0 and 0.9M NaCl, with 0.1M NaCl being particularly preferred, and within a pH range of between 5 and 9, preferably between 6.8 and 8. Sufficient time for the binding and response will generally be between 5 and 15 minutes after exposure.

Once the compound has been exposed to a recombinant glucagon receptor in the presence of a glucagon agonist, under conditions and for a time sufficient to allow binding of the compound to the receptor, a reduction in the stimulation of the response pathway may be detected if the compound competes with the glucagon agonist for the recombinant glucagon receptor. Within one embodiment of the invention, the response pathway is a membrane-bound adenylate cyclase response pathway, and the step of detecting comprises measuring a reduction in cAMP production by the membrane-bound adenylate cyclase response pathway, relative to the cyclic AMP production in the presence of the glucagon agonist alone. For purposes of the present invention, it is preferred that the reduction in the stimulation of the response pathway be equivalent to or greater than the reduction associated with des-His$^1$-glucagon. Adenylate cyclase activity assays may be carried out, for example, utilizing method(s) described by Lin et al. (*Biochem.* 14:1559–1563, 1975), and in the Examples. These methods measure the level of stimulation of cAMP relative to native glucagon, and generally involve exposing a preparation of cells which express a biologically active recombinant glucagon receptor to a mixture of glucagon and the test compound in the presence of radiolabelled ATP.

Alternatively, cAMP production may also be readily measured using methods which are well known in the art, including, for example, methods described by Salomon et al. (*Anal Biochem.* 58:541–548, 1976) or Krishna et al. (*J. Pharmacol. Exp. Ther.* 163:379, 1968), or, preferably, using commercially available kits such as the Scintillation Proximity Assay Kit from Amersham Corporation. The Scintillation Proximity Assay Kit measures the production of cAMP by competition of iodinated-cAMP with anti-cAMP antibodies. Particularly preferred glucagon receptors have a biological activity in such assays of $ED_{50}$ (Effective Dose for a 50% response) less than 1 nM, more preferably with an $ED_{50}$ of less than 0.7 nM, and most preferably with an $ED_{50}$ of less than 0.25 nM.

Within a further embodiment of the invention, the response pathway includes a luciferase reporter system. Briefly, luciferase is an enzyme which catalyzes the release of photons by luciferin, and thus may be readily detected upon expression in the presence of luciferin (Alam and Cook, *Anal. Biochem.* 188:245–254, 1990). As is described in more detail below, within a particularly preferred embodiment of the invention a DNA construct is provided comprising a cyclic AMP response element such as a proenkephalin cyclic AMP response element, which is operably linked to a luciferase cDNA. The DNA construct comprising the luciferase cDNA is stably transfected into a host cell. The host cell is then transfected with a second DNA construct containing a first DNA segment encoding the glucagon receptor operably linked to additional DNA segments necessary for the expression of the receptor. Upon binding of a glucagon receptor agonist, the elevated cAMP levels induce the expression of luciferase. The luciferase is exposed to luciferin, and the photons released during the oxidation of luciferin by the luciferase is measured.

Within other embodiments of the invention, activation of a esponse pathway results in an increase of the intracellular concentration of free alcium. A variety of assays may be performed in order to determine the concentration of free intracellular calcium, including, for example, the calcium fluor QuinZ method described by Charest et al. (*J. Biol. Chem.* 259:8769–8773, 1983), or the aequorin photoprotein method described by Nakajima-Shimada (*Proc. Natl. Acad. Sci. USA* 88:6878–6882, 1991). A particularly preferred method is the intracellular calcium photoimaging method, which is described in more detail below in Example 6. Briefly, within one embodiment cells are transformed with a glucagon receptor expressing plasmid, and grown for three days under normal culture conditions. The growth medium is then removed, and replaced with a solution containing 10 $\mu$M fura-2AM (see Grynkiewicz et al., *J. Biol. Chem.* 260:3440–3450, 1985). The cells are then incubated for 30 minutes in the dark, followed by rinsing, and another incubation for 30 to 120 minutes. Photoimaging may be performed with a Nikon Diaphot inverted fluorescence microscope equipped with a mercury arc lamp. Cells may first be monitored for at least 60 seconds to establish a baseline, followed by stimulation with a buffer containing glucagon. Images are typically recorded for at least three minutes after stimulation. Software such as Inovision (Research Triangle Park, N.C.) may be utilized to process and quantify the images.

Glucagon antagonists which have been detected as discussed above may be purified by ion-exchange and partition chromatography as described by, for example, Coy et al. (Peptides Structure and Function, Pierce Chemical Company, Rockford Ill., pp. 369–372, 1983), by reverse-phase chromatography (Andreu and Merrifield, *Eur. J. Biochem.* 164:585–590, 1987) or by HPLC (e. g., Kofod et al., Int. *J. Peptide Protein Res.* 32:436–440, 1988). Additional purification may be achieved by conventional chemical purification means, such as liquid chromatography, gradient centrifugation, and gel electrophoresis, among others. Methods of protein purification are known in the art (see generally, Scopes, R., *Protein Purification,* Springer-Verlag, N.Y., 1982), and may be applied to the purification of the recombinant glucagon antagonists described herein. Alternatively, glucagon antagonists may be synthesized by the solid-phase method of Barany and Merrifield (in *The Peptides*, vol. 2A, Gross and Meienhofer, eds., Academic Press, N.Y., pp. 1–284, 1979) or by use of an automated peptide synthesizer.

Substantially pure recombinant glucagon antagonists of at least about 50% homogeneity are preferred, at least about 70%–80% homogeneity more preferred, and 95%–99% or more homogeneity most preferred, particularly for pharmaceutical uses. Once purified, or to homogeneity, as desired, the glucagon antagonists may be used therapeutically. In general, the antagonists may be administered parenterally or by infusion. Typically, the antagonists are present as free bases or as acid salts. Suitable salts should be pharmaceutically acceptable. Representative examples include metal salts, alkali and alkaline earth metal salts such as potassium or sodium salts. Other pharmaceutically acceptable salts include citric, succinic, lactic, hydrochloric and hydrobromic acids. Parenteral compositions may be formulated in aqueous isotonic solutions of between pH 5.6 and 7.4. Suitable isotonic solutions may include sodium chloride, dextrose, boric acid sodium tartrate, and propylene glycol solutions. Therapeutic doses of antagonists may be administered simultaneously with insulin either in the same composition or in separate compositions.

DIAGNOSTIC USE OF GLUCAGON RECEPTOR PROBES

Within another aspect of the present invention, probes and primers are provided for detecting glucagon receptors. Within one embodiment of the invention, probes are provided which are capable of hybridizing to glucagon receptor DNA or RNA. For purposes of the present invention, probes are "capable of hybridizing" to glucagon receptor DNA if they hybridize under conditions of either high or low stringency (see, Sambrook et al., supra). Preferably, the probe may be utilized to hybridize to suitable nucleotide sequences in the presence of 6× SSC, 1× Denhardt's (Sambrook et al., supra), 0.1% SDS at 65° C. and at least one wash to remove excess probe in the presence of 2× SSC, 1× Denhardt's, 0.1% SDS at 65° C. Probe sequences are preferably designed to allow hybridization to glucagon receptor sequences, but not to secretin, calcitonin or parathyroid hormone receptor sequences.

Probes of the present invention may be composed of either deoxyribonucleic acids (DNA) or ribonucleic acids (RNA), and may be as few as about 12 nucleotides in length, usually about 14 to 18 nucleotides in length, and possibly as large as the entire sequence of the glucagon receptor. Selection of probe size is somewhat dependent upon the use of the probe. For example, in order to determine the presence of various polymorphic forms of the glucagon receptor within an individual, a probe comprising virtually the entire length of the glucagon receptor coding sequence is preferred. Glucagon receptor probes may be utilized to identify polymorphisms linked to the glucagon receptor gene (see, for example, *Weber, Genomics* 7:524–530, 1990; and Weber and May, *Amer. J Hum. Gen.* 44:388–396, 1989). Such polymorphisms may be associated with inherited diseases such as diabetes.

Probes may be constructed and labeled using techniques which are well known in the art. Shorter probes of, for example, 12 bases may be generated synthetically. Longer probes of about 75 bases to less than 1.5 kb are preferably generated by, for example, PCR amplification in the presence of labeled precursors such as $^{32}$P-dCTP, digoxigenin-dUIT, or biotin-dATP. Probes of more than 1.5 kb are generally most easily amplified by transfecting a cell with a plasmid containing the relevant probe, growing the transfected cell into large quantities, and purifying the relevant sequence from the transfected cells (see, Sambrook et al., supra).

Probes may be labeled by a variety of markers, including for example, radioactive markers, fluorescent markers, enzymatic markers, and chromogenic markers. The use of $^{32}$P is particularly preferred for marking or labelling a particular probe.

Probes of the present invention may also be utilized to detect the presence of a glucagon receptor mRNA or DNA within a sample. However, if glucagon receptors are present in only a limited number, or if it desired to detect a selected mutant sequence which is present in only a limited number, or if it is desired to clone a glucagon receptor from a selected warm-blooded animal, then it may be beneficial to amplify the relevant sequence such that it may be more readily detected or obtained.

A variety of methods may be utilized in order to amplify a selected sequence, including for example RNA amplification (see Lizardi et al., *Bio/Technolog* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing Polymerase Chain Reaction ("PCR") (see, U.S. Pat. Nos. 4,683,195, 4,683,202, and 4,800,159) (see also, U.S. Pat. Nos. 4,876,187, and 5,011,769, which describe an alternative detection/amplification system comprising the use of scissile linkages).

Within a particularly preferred embodiment, PCR amplification is utilized to detect or obtain a glucagon receptor DNA. Briefly, as described in greater detail below, a DNA sample is denatured at 95° C. in order to generate single stranded DNA. Specific primers, as discussed below, are then annealed at 37° C. to 70° C., depending on the proportion of AT/GC in the primers. The primers are extended at 72° C. with Taq polymerase in order to generate the opposite strand to the template. These steps constitute one cycle, which may be repeated in order to amplify the selected sequence.

Primers for the amplification of a selected sequence should be selected from sequences which are highly specific and form stable duplexes with the target sequence. The primers should also be non-complementary, especially at the 3' end, should not form dimers with themselves or other primers, and should not form secondary structures or duplexes with other regions of DNA In general, primers of about 18 to 20 nucleotides are preferred, and may be easily synthesized using techniques well known in the art. Particularly preferred primers are set forth below in Table 1, and include the degenerate oligonucleotides ZC4715 and ZC4701 (SEQ ID NOS: 9 and 8, respectively), as well as oligonucleotides ZC4758 and ZC4778 (SEQ ID NOS: 10 and 11, respectively).

ADDITIONAL USES OF GLUCAGON RECEPTOR NUCLEOTIDE SEQUENCES

Within yet another aspect of the present invention, viral vectors are provided which may be utilized to treat diseases wherein either the glucagon receptor (or a mutant glucagon receptor) is over-expressed, or where no glucagon receptor is expressed. Briefly, within one embodiment of the invention, viral vectors are provided which direct the production of antisense glucagon receptor RNA, in order to prohibit the over-expression of glucagon receptors, or the expression of mutant glucagon receptors. Within another embodiment, viral vectors are provided which direct the expression of glucagon receptor cDNA. Viral vectors suitable for use in the present invention include, among others, recombinant vaccinia vectors (U.S. Pat. Nos. 4,603,112 and 4,769,330), recombinant pox virus vectors (PCT Publication No. WO 89/01973), and preferably, recombinant retroviral vectors ("Recombinant Retroviruses with Amphotropic and Ecoptropic Host Ranges," PCT Publication No. WO 90/02806; "Retroviral Packaging Cell Lines and Processes of Using Same," PCT Publication No. WO 89/07150; and "Antisense RNA for Treatment of Retroviral Disease States," PCT Publication No. WO/03451).

As noted above, viral vectors of the present invention may be utilized in the treatment of disease states wherein either the glucagon receptor is over-expressed, a mutant glucagon receptor is expressed, or where no glucagon receptor is expressed.

The following examples are offered by way of illustration, and not by way of limitation.

EXAMPLES

Example 1

SYNTHESIS OF cDNA AND PREPARATION OF cDNA LIBRRIES

A. Rat Liver cDNA Synthesis

Livers from 30-gm female Sprague-Dawley rats (Simonsen Labs, Gilroy, Calif.) were removed and immediately placed in liquid nitrogen. Total RNA was prepared from the liver tissue using guanidine isothiocyanate (Chirgwin et al., *Biochemistry* 18:52–94, 1979) and CsCl centrifugation. Poly(A)$^+$RNA was isolated using oligo d(T) cellulose chromatography (Aviv and Leder, *Proc. Natl. Acad. Sci. USA* 69:1408–1412, 1972).

First strand cDNA was synthesized from two-time poly d(T)-selected liver poly(A)$^+$RNA. Ten microliters of a solution containing 10 μg of liver poly(A)$^+$RNA was mixed with 2 μl of 20 pmole/μl first strand primer ZC3747 (SEQ ID NO: 7) and 4 μl of diethylpyrocarbonate-treated water. The mixture was heated at 65° C. for 4 minutes and cooled by chilling on ice.

The first strand cDNA synthesis was initiated by the addition of 8 μl of 5× SUPERSCRIPT buffer (GIBCO BRL, Gaithersburg, Md.), 4 μl of 100 mM dithiothreitol and 2.0 μl of a deoxynucleotide triphosphate solution containing 10 mM each of DATP, dGTP, dTTP and 5-methyl-dCTP (Pharmacia LKB Biotechnology Inc., Piscataway, N.J.) to the RNA-primer mixture. The reaction mixture was incubated at 42° C. for 3 minutes. After incubation, 6.0 μl of 200 U/μl SUPERSCRIPT reverse transcriptase (GIBCO BRL) was added. The efficiency of the first strand synthesis was analyzed in a parallel reaction by the addition of 10 μCi of $^{32}$P-αdCTP to a 10 μl aliquot of the reaction mixture to label the reaction products. The first strand synthesis reaction mixtures were incubated at 45° C. for 45 minutes followed by a 15 minute incubation at 50° C. The reactions were terminated by addition of water to a final volume of 100 μl followed by two phenol/chloroform (1:1) extractions and one chloroform/isoamylalcohol (24:1) extraction. Unincorporated nucleotides were removed from each reaction by twice precipitating the cDNA in the presence of 6 μg of glycogen carrier, 2.5M ammonium acetate and 2.5 volume ethanol. The unlabeled cDNA was resuspended in 50 μl water and used for the second strand synthesis. The length of first strand cDNA was assessed by resuspending the labeled cDNA in 20 μl water and determining the cDNA size by agarose gel electrophoresis.

Second strand synthesis was performed on the RNA-DNA hybrid from the first strand synthesis reaction under conditions that promoted first strand priming of second strand synthesis resulting in DNA hairpin formation. A reaction mixture was prepared containing 20.0 μl of 5× polymerase I buffer (100 mM Tris, pH 7.4, 500 mM KCl, 25 mM MgCl$_2$, 50 mM (NH$_4$)$_2$SO$_4$), 4.0 μl of 100 mM dithiothreitol, 1.0 μl of a solution containing 10 mM of each deoxynucleotide triphosphate, 3.0 μl of β-NAD, 15.0 μl of 3 U/μl *E. coli* DNA ligase (NBL Enzymes Ltd., Cramlington, Northumbria, England), 5.0 μl of 10 U/μl *E. coli* DNA polymerase I (GIBCO BRL) and 50.0 μl of the unlabeled first strand DNA. A parallel reaction in which a 10 μl aliquot of the second strand synthesis was labeled by the addition 10 μCi of $^{32}$P-αdCTP was used to monitor the efficiency of second strand synthesis. The reaction mixtures were incubated at room temperature for 4 minutes followed by the addition of 1.5 μl of 2 U/μl RNase H (GIBCO BRL) to each reaction mixture. The reactions were incubated at 15° C. for 2 hours followed by a 15 minute incubation at room temperature. The reactions were each terminated by the addition of 4 μl of 500 mM EDTA followed sequentially by a phenol/chloroform and a chloroform/isoamylalcohol extraction as described above. The DNA from each reaction was precipitated in the presence of ethanol and 2.5M ammonium acetate. The DNA from the unlabeled reaction was resuspended in 50 μl water. The labeled DNA was resuspended and electrophoresed as described above.

The single-stranded DNA in the hairpin structure was cleaved using mung bean nuclease. The reaction mixture contained 10 μl of 10×Mung Bean Nuclease Buffer (Stratagene Cloning Systems, La Jolla, Calif.), 4 μl of 200 mM dithiothreitol, 34 μl water, 50 μl of the second strand cDNA and 2 μl of a 1:10 dilution of Mung Bean nuclease (Promega Corp., Madison, Wis.) in Stratagene MB dilution Buffer (Stratagene Cloning Systems). The reaction was incubated at 37° C. for 15 minutes, and the reaction was terminated by the addition of 20 μl of Tris-HCl, pH 8.0 followed by sequential phenol/chloroform and chloroform/isoamylalcohol extractions as described above. Following the extractions, the DNA was precipitated in ethanol and resuspended in water.

The resuspended cDNA was blunt-ended with T4 DNA polymerase. The cDNA, which was resuspended in a volume of 192 μl of water, was mixed with 50 μl of 5×T4 DNA polymerase buffer (250 mM Tris-HCl, pH 8.0, 250 mM KCl, 25 mM MgCl$_2$), 3 μl of 100 mM dithiothreitol, 3 μl of a solution containing 10 mM of each deoxynucleotide triphosphate and 2 μl of 6.7 U/μl T4 DNA polymerase (Pharmacia LKB Biotechnology Inc.). After an incubation at 15° C. for 30 minutes, the reaction was terminated by the addition of 2 μl of 500 mM EDTA followed by serial phenol/chloroform and chloroform/isoamylalcohol extractions as described above. The DNA was ethanol precipitated and resuspended in 30 μl of water. Based on the incorporation of $^{32}$P-dCIP, the yield of cDNA was estimated to be 4 μg from a starting mRNA template of 10 μg.

B. Preparation of a Rat Liver cDNA library

Eco RI adapters (Invitrogen, San Diego, Calif.) were added to the cDNA prepared above to facilitate the cloning of the cDNA into a mammalian expression vector. A 10 μl aliquot of the cDNA and 800 pmole of the adaptor (12 μl) were mixed with 4.0 μl 10×ligase buffer (Stratagene Cloning Systems), 4.0 μl 10 mM ATP, 6.0 μl water and 16 Units of T$_4$ DNA ligase (4.0 μl; Stratagene Cloning Systems). The reaction was incubated for sixteen hours at a temperature gradient of 4° C. to 15° C. The reaction was terminated by the addition of 185 μl of water, 25 μl of REACT 2 buffer (GIBCO BRL) followed by an incubation at 65° C. for between 30 and 60 minutes. After incubation, the reaction was phenol/chloroform extracted followed by a chloroform/isoamylalcohol extraction and ethanol precipitation as described above. Following centrifugation, the DNA pellet was washed with 70% ethanol and was air dried. The pellet was resuspended in 180 μl of water.

To facilitate the directional insertion of the cDNA into a mammalian expression vector, the cDNA was digested with Xho I, resulting in a cDNA having a 5' Eco RI adhesive end and a 3' Xho I adhesive end. The Xho I restriction site at the 3' end of the cDNA was introduced through the ZC3747 primer (SEQ ID NO: 7). The restriction digestion was terminated by serial phenol/chloroform and chloroform/isoamylalcohol extractions. The cDNA was ethanol precipitated, and the resulting pellet was washed with 70% ethanol and air-dried. The pellet was resuspended in 1×loading buffer (10 mM phosphate buffer, pH 8.8, 5% glycerol, 0.125% bromphenol blue).

The resuspended cDNA was heated to 65° C. for 10 minutes, cooled on ice and electrophoresed on a 0.9% low melt agarose gel (Seaplaque GTG Low Melt Agarose, FMC Corp., Rockland, Me.) using the BRL 1 kb ladder (GIBCO BRL) and the Pharmacia 100 bp ladder (Pharmacia LKB Biotechnology Inc.) as size markers. The contaminating adaptors and by-product fragments below 800 bp in size were excised from the gel. The electrodes were reversed and the cDNA was electrophoresed until concentrated near the lane origin. The area of the gel containing the concentrated DNA was excised, placed in a microfuge tube, and the approximate volume of the gel slice was determined. An aliquot of TE equivalent to half the volume of the gel slice was added to the tube, and the agarose was melted by heating to 65° C. for fifteen minutes. Following equilibration of the sample to 42° C., approximately 5 units of β-Agarase I (New England Biolabs, Beverly, Mass.) was added. The sample was incubated for 90 minutes to digest the agarose. After incubation, a 0.1× volume of 3M sodium acetate was added to the sample, and the mixture was incubated on ice for fifteen minutes. After incubation, the sample was centrifuged at 14,000×g for fifteen minutes at 4° C. to remove the undigested agarose. The CDNA in the supernatant was ethanol precipitated. The cDNA pellet was washed with 70% ethanol, air dried and resuspended in 10 μl of water.

The resulting cDNA was cloned into the E. coli vector pZCEP, a derivative of pCDNA1 (Invitrogen) in which the M13 origin of replication and the SupF selectable marker was replaced with the beta lactamase cassette from pUC18. Plasmid pZCEP, which was linearized by digestion with Eco RI and Xho 1, was ligated with the Eco RI-Xho I CDNA. The resulting plasmids were electroporated into E. coli strain DH1OB ELECIROMAX cells (GIBCO BRL).

C. Synthesis of Human Islet Cell cDNA

Islet cells were isolated from human pancreata obtained from organ transplant donors for whom a matched recipient was not available. After in situ perfusion with cold UW solution (Du Pont, Boston, Mass.), each pancreas was carefully excised, the pancreatic duct cannulated, and 4 mg/ml collagenase solution (Type V, Sigma, St. Louis, Mo.) infused at a constant rate, first at 4° C. and then 39° C. The gland was teased apart, and liberated fragments were washed by centrifugation, triturated through needles of decreasing caliber, and purified by discontinuous Ficoll density centrifugation (Warnock, *Diabetes* 35(Suppl. 1):136–139, 1989). Material harvested from the upper interfaces was pooled and counted after a determination of islet purity by dithiazone staining. Islets used in library construction were greater than 65% pure, while islets used in Northern blots were greater than 40% pure. The average islet diameter was 175 μm. Additionally, the isolated islets showed both first and second phase insulin secretory function after perfusion with either high glucose or with isobutylmethylxanthine (IBMX).

Poly(A)$^+$RNA was isolated using the FASTTRACK mRNA isolation kit (Invitrogen) according to the manufacturer's instructions. Briefly, 30,000 purified islets were quickly lysed in lysis buffer, homogenized using needles of decreasing caliber, and digested in the presence of proteinase K and RNasin, then poly(A)$^+$RNA was selected by oligo-d(T) cellulose chromatography. The concentration and purity of the eluted fractions were determined at OD$_{260/280}$.

Approximately 2.5 μg poly(A)$^+$RNA from the human islets was used for cDNA library construction using a LIBRARIAN R II cDNA library construction system (Invitrogen) and DHIOB ELECTROMAX E. coli cells (GIBCO BRL) according to the manufacturer's instructions. In short, approximately 2.5 μg of poly(A)$^+$RNA, isolated from human islets, was converted into double-stranded cDNA, followed by the addition of BstX I nonpalindromic linkers (Invitrogen). The cDNA was size fractionated, and the unreacted linkers were removed by agarose gel electrophoresis and electroelution. Complementary DNA strands larger than 600 bp were selected.

EXAMPLE 2

ISOLATION OF A RAT GLUCAGON RECEPTOR cDNA BY POLYMERASE CHAIN REACTION AMPLIFICATION

Rat liver cDNA was used as a template for the amplification of glucagon receptor sequences using degenerate oligonucleotides (ZC4715 and ZC4701; SEQ ID NOS: 9 and 8, respectively) corresponding to regions of high conservation among the members of the secretin gene family. A 50 μl reaction was set up containing 5 ng of the template cDNA (Example 1A); 100 pmoles each of oligonucleotides ZC4715 (SEQ ID NO: 9) and ZC4701 (SEQ ID NO: 8); 0.25 mM of each deoxynucleotide triphosphate (Cetus, Emeryville, Calif.); 1×of Promega 10×buffer (Promega Corp.); and 1.25 Units Taq polymerase (Promega). The PCR reaction was run for 40 cycles (one minute at 95° C., one minute at 42° C. and two minutes at 72° C.) followed by a 7 minute incubation at 72° C.

The 650 bp PCR product was isolated by gel electrophoresis and ligated with pCR1000 (Stratagene Cloning Systems). The resulting plasmid was used to transform *E. coli* XL-1 cells. Plasmid DNA was prepared from a selected transformant, designated G13/pCR1000, and sequenced (SEQ ID NO: 14). Sequence analysis of the clone showed that the insert encoded a polypeptide related to the secretin receptor.

EXAMPLE 3

CLONING OF A FULL LENGTH RAT GLUCAGON RECEPTOR cDNA

A full length rat glucagon receptor cDNA was obtained by screening the library described in Example 1B in a glucagon binding assay. The library was plated to obtain one million independent clones. The transformant colonies from each plate were scraped into 10 ml of LB-Amp (Sambrook et al., supra). The cells were spun down and the media was discarded. The cell pellets were resuspended in 4 ml of LB-Amp, 15% glycerol, and four one-milliliter aliquots were stored at –80° C. The first glycerol stock was titred, and 100 pools of 5000 colonies per plate were plated. After colonies had grown, each plate was scraped into 10 ml of LB-amp. An aliquot of the cells from each pool was removed for use in preparing plasmid DNA. The remaining cell mixtures were brought to a final concentration of 15% glycerol, aliquoted and frozen at –80° C. Plasmid DNA was prepared from each pool of cells, and the DNA was digested with RNAse (Boehringer Mannheim, Indianapolis, Ind.) according to the manufacturer's instructions. The RNAse reaction was terminated by a phenol/chloroform/isoamylalcohol (24:24:1) extraction, and the DNA was ethanol precipitated.

The plasmid DNA from each pool was transfected into COS-7 cells (ATCC CRL 1651), and the transfectants were screened for the presence of glucagon receptors by a $^{125}$I-glucagon binding assay. Briefly, one day prior to transfection approximately $2 \times 10^5$ COS-7 cells were plated on sterile single chamber slides (Nunc AS, Roskilde, Denmark) that had been coated with 10 μg/ml of human fibronectin (Table 1) for 30 minutes at room temperature and washed with phosphate buffered saline (PBS, Sigma Chemical Co., St. Louis, Mo.). Two micrograms of plasmid DNA from each pool was used to transfect the cells grown on individual chamber slides using the method essentially described by McMahan et al. (*EMBO J.* 10:2821–2832, 1991; which is incorporated by reference herein in its entirety). After transfection, the cells were grown for 72 hours at 37° C. in 5% $CO_2$.

TABLE 1

| | Human Fibronectin |
|---|---|
| 4 gm | human plasma fibronectin lyophilized powder (Alpha Therapeutic Corp., Los Angeles, Calif.) |
| 50 ml | 1 mM $NaPO_4$, pH 7.4 (mixture of mono- and di-Na), 300 mM NaCl |

The lyophilized powder is dissolved in the buffer solution. The ammonium sulfate is then added to a concentration of 25%, and the solution is allowed to precipitate for two hours at 4° C. The fibronectin is pelleted by centrifugation at 1,000 rpm in a Bench Top centrifuge (Beckman Instruments, Inc., Irvine, Calif.) for fifteen minutes. The supernatant is discarded, and the pellet is dissolved in 10 ml of the $NaPO_4$ buffer solution (above).

The fibronectin, in a final volume of 16.9 ml, is dialyzed overnight against 1 liter of a $NaPO_4$ buffer solution (described above). The dialyzed material is diluted threefold with 1 mM $NaPO_4$, pH 7.4, to produce a solution of 1 mM $NaPO_4$, pH 7.4, 100 mM NaCl. The fibronectin is then diluted two-fold with distilled water. The stringy, insoluble precipitate is removed with a glass rod.

The fibronectin is subjected to FPLC across a 50 ml DEAE FF Sepharose column (Pharmacia LKB Biotechnology Inc., Piscataway, N.J.) that has been equilibrated with three volumes of 10 mM Tris, pH 8.1, 50 mM NaCl. After the column has been washed with 10 mM Tris, pH 8.1, 50 mM NaCl until a baseline sample is generated, the fibronectin is eluted with a salt gradient to 10 mM Tris, pH 8.1, 300 mM NaCl. The fractions are collected, aliquots of the fractions are electrophoresed on acrylamide gels, and the gels are analyzed by Coomasie Blue staining and Western analysis. Peak fractions are pooled and dialyzed against 10 mM CAPS (3-(cyclohexylamine)-1 propane-sulfonic acid, Sigma), pH 11.0, 10 mM $CaCl_2$, 150 mM NaCl. The solution is stored at –80° C.

To prepare the transfectants for the $^{125}$I-glucagon binding assay, the spent media were aspirated from the cells, and the cells were washed three times with cold (4° C) PBS. After the final wash, the cells were covered with Binding Media (Table 2) and incubated for ten minutes at room temperature. The media were replaced with 0.5 ml of Binding Media containing 0.5 nM $^{125}$I-glucagon (Amersham receptor grade, specific activity 2000 Ci/mmole; Amersham). The cells were then rocked at 30° C. for one hour. The media were aspirated from the cells, cold (4° C.) Binding Medium without glucagon was added, and the cells were incubated for 5 minutes at room temperature. The media were aspirated from the cells, and the cells were washed three times with cold (4° C.) PBS. After the final wash, the cells were fixed with 1 ml of 2.5% glutaraldehyde in PBS at room temperature for 20 minutes. The glutaraldehyde was removed, and the cells were rinsed three time with PBS. The slides were air dried for one hour at room temperature, dipped in liquid photographic emulsion (Eastman Kodak Co., Rochester, N.Y.) according the manufacturer's directions, and dried at room temperature in the dark for at least 30 minutes. The slides were then plated in a light-proof box for 72 hours at 4° C. Cells capable of binding glucagon were detected by 2.5×magnification under bright field illumination. One pool, #57, was identified as containing cells capable of binding glucagon.

TABLE 2

Binding media
RPMI 1640 (Sigma) containing:
20 μg/ml bacitracin (Sigma)
25 mM HEPES Buffer, pH 7.4
1% Penicillin/Streptomycin (Sigma)
2 mM glutamine
50 U/ml aprotinin (Sigma)
1% bovine serum albumin, fraction V (Sigma)
1M Sodium Bicarbonate
8.4 gm solid $NaCO_3$ The sodium bicarbonate is poured into a 100 ml stoppered graduate, and 80 ml of distilled water is added. The solution is mixed until the solid is dissolved. Distilled water is added to 100 ml. The solution is mixed again and stored at 4° C. in a stoppered bottle.
Medium One milliliter of 1M sodium bicarbonate is added per liter of distilled water. Four liters are prepared either in advance and with the solution chilled overnight or prepared with cold distilled water.

69% Sucrose Solution
69 gm sucrose
Sucrose is dissolved in 31 ml of distilled water with heat. The concentration of the solution is measured with a refractometer. Solid sucrose or water is added as needed to adjust the concentration to 69+/−0.5%.
42.3% Sucrose
42 gm sucrose
Sucrose is dissolved in 57 ml of distilled water with heat. The concentration of the solution is measured with a refractometer. 69% Sucrose Solution or water is added as needed to adjust the concentration to 42.3+/−1%.
2×Binding Buffer
100 mM HEPES, pH 7.3
300 mM NaCl
2 mM EDTA
2% bovine serum albumin
1.6 mg/ml bacitracin
Imaging Buffer
140 mM NaCl
10 mM HEPES
5.6 mM Glucose
5 mM KCl
1 mM $MgSO_4$
1 mM $CaCl_2$
Fura-2 AM Solution
50 mg fura-2 AM (Molecular Probes)
50 ml DMSO
5 ml Imaging Buffer
Fifty milligrams of fura-2 AM is dissolved in 50 ml DMSO.
After the solid has dissolved, the solution is mixed with 5 ml Imaging Buffer.

An aliquot of the plasmid DNA from the #57 pool was subjected to PCR amplification using oligonucleotides ZC4701 and ZC4715 (SEQ ID NOS: 8 and 9, respectively). A 50 μl reaction mixture was prepared containing between 200 ng and 400 ng of plasmid DNA from the #57 pool; 100 pMoles each of oligonucleotides ZC4701 and ZC4715 (SEQ ID NOS: 8 and 9, respectively); 50 mM KCl; 10 mM Tris-HCl, pH 9.0 (at 20° C.); 1.5 mM $MgCl_2$; 0.01% gelatin; 0.1% Triton X-100; 0.2 mM of each deoxynucleotide triphosphate (Pharmacia LKB Biotechnology Inc) and 1 Unit of Taq polymerase (Promega). The PCR reaction was run for 30 cycles (two minutes at 95° C., two minutes at 45° C. and two minutes at 72° C.) followed by a 7 minute incubation at 72° C. The reaction mixture was stored at 4° C. Analysis of the PCR product by gel electrophoresis showed the presence of a 700 bp band, which was approximately the same size as the product described in Example 2.

The glycerol stock from pool #57 was titred, and 20 plates of 500 colonies were plated. The colonies were pooled, and glycerol stock and plasmid DNA were prepared as described above. The plasmid DNA was transfected into COS-7 cells, and transfectants were screened using the glucagon binding assay described above. One pool, #57-18, was identified as containing cells capable of binding glucagon.

An aliquot of plasmid DNA from pool #57-18 was subjected to PCR amplification using oligonucleotides ZC4701 and ZC4715 (SEQ ID NOS:
8 and 9, respectively) as described above. Analysis of the PCR product by gel electrophoresis showed the presence of a 700 bp band, confirming the presence of glucagon receptor DNA sequences.

The glycerol stock from pool #57-18 was titred, and 6 plates of 50 colonies and 47 plates of 20 colonies were plated. The colonies were pooled, and glycerol stocks and plasmid DNA were prepared as described above. An aliquot from each pool of plasmid DNA was transfected into COS-7 cells, and transfectants were screened using the glucagon binding assay described above. In addition, an aliquot from each pool of plasmid DNA was subjected to PCR amplification using oligonucleotides ZC4701 and ZC4715 (SEQ ID NOS: 8 and 9, respectively) as described previously. Four positive pools (#57-18-16, #57-18-18, #57-18-36 and #57-18-48) were identified as containing cells capable of binding glucagon and were shown by PCR amplification to contain the confirmatory 700 bp band.

Figure 2:
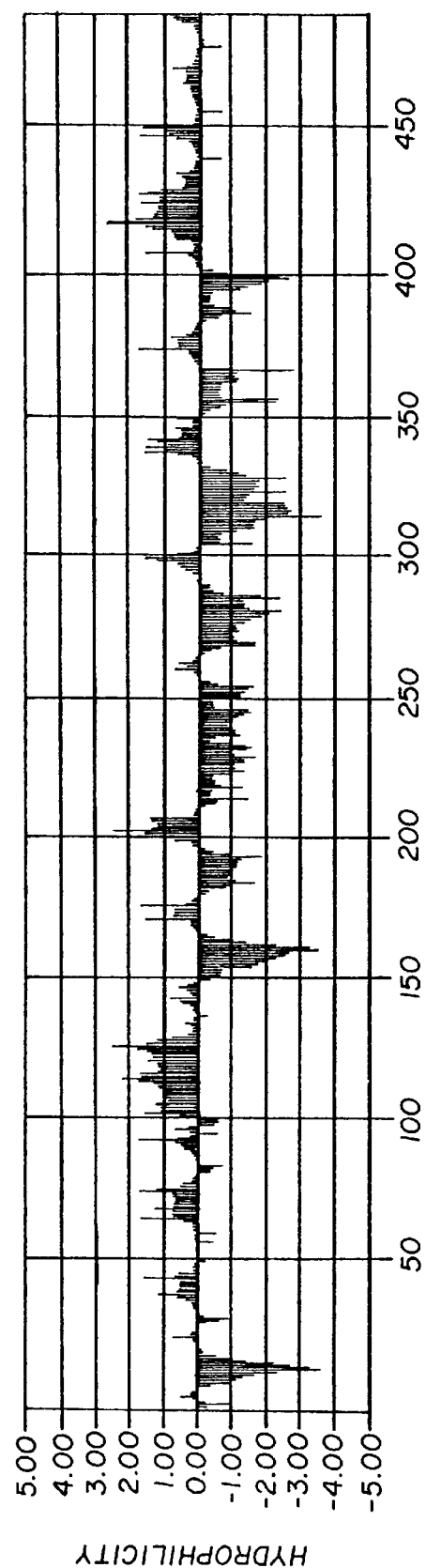
FIG. 2 graphically depicts the hydrophobicity of a rat glucagon receptor.

To isolate the cDNA, two 150-mm plates were each plated with 2,500 colonies of the #57-18 pool. Filter lifts were prepared using the method essentially described by Hanahan and Meselson (*Gene* 10:63, 1980) and Sambrook et al. (ibid.), which are incorporated herein by reference in their entirety. The hybridization probe was obtained by PCR amplification of plasmid DNA from the #57 pool using the oligonucleotides and methods described above. The PCR product was gel-purified from a low-melt agarose gel and was random-primed using the MEGAPRIME kit (Amersham, Arlington Heights, Ill.) according to the manufacturer's instructions. The filters were hybridized in a solution containing 6× SSC, 5× Denhardt's, 5% SDS, 200 μg/ml sonicated salmon sperm DNA and $2\times10^5$ cpm/ml of $^{32}$P-labeled PCR fragment. The filters were hybridized overnight at 65° C. The excess label was removed by three washes with 2× SSC, 1% SDS at 65° C. The filters were exposed to film for four hours at −80° C. with two screens. A positive clone containing the plasmid, pLJ4, was identified and sequenced. Plasmid pLJ4 has been deposited with the American Type Culture Collection (12301 Parklawn Dr., Rockville, Md. 20852) as an *E. coli* transformant under accession number 69056 on Aug. 21, 1992. Restriction endonuclease analysis and sequence analysis showed that pLJ4 contained an approximately 2 kb insert encoding a 485 amino acid protein with a predicted molecular weight of 54,962 daltons. The nucleic acid sequence and deduced amino acid sequence are shown in SEQ ID NOS: 14 and 15. Hydropathy analysis using the method of Kyte and Doolittle (*J. MoL Biol.* 157:105–132, 1982; which is incorporated by reference herein) revealed eight clusters of hydrophobic amino acids corresponding to an amino-terminal signal sequence and seven transmembrane domains (FIG. 2). In addition, analysis of the deduced amino acid sequence showed the presence of four potential N-linked glycosylation sites located in an extended hydrophilic sequence and the presence of six cysteines in the same region.

EXAMPLE 4

ISOLATION OF A HUMAN GLUCAGON RECEPTOR cDNA BY POLYMERASE CHAIN REACTION AMPLIFICATION

Human islet cell cDNA (Example 1C) was used as a template for the amplification of human glucagon receptor sequences using the degenerate oligonucleotides ZC4715 and ZC4701 (SEQ ID NOS: 9 and 8, respectively). A 50 μl reaction was set up containing 5 ng of the template cDNA (Example 1C); 100 pmoles each of oligonucleotides ZC4715 (SEQ ID NO: 9) and ZC4701 (SEQ ID NO: 8); 0. 25 mM of each deoxynucleotide triphosphate (Cetus, Emeryville, Calif.); 1×of Promega 10× buffer (Promega) and 1.25 Units Taq polymerase (Promega). The PCR reaction was run for 40 cycles (one minute at 95° C., one minute at 45° C. and two minutes at 72° C.) followed by a 7 minute incubation at 72° C.

An approximately 750 bp PCR product was isolated by gel electrophoresis. One tenth of the isolated PCR product was used as a template 25 for another PCR reaction using oligonucleotides ZC4758 and ZC4778 (SEQ ID NOS: 10 and 11), which were designed to insert a Bam HI restriction site at the 3' end and an Eco RI restriction site at the 5' end of the PCR product for subcloning. A 50 μl reaction mixture was set up as described above. The PCR reaction was run for 40 cycles (one minute at 95° C., one minute at 50° C. and one and a half minutes at 72° C.) followed by a 7 minute incubation at 72° C.

To screen transformants for a human glucagon receptor sequence, the insert DNA present in each transformant was amplified using oligonucleotides ZC447 and ZC976 (SEQ ID NOS: 1 and 2, respectively), which were designed as universal pUC sequencing primers and primed to pUC sequences flanking the PCR product insert. Forty-eight of the transformants were each picked into a 25 μl reaction mixture containing 20 pmol of each oligonucleotide; 0.125 mM of each deoxynucleotide triphosphate (Cetus, Emeryville, Calif.); 1× of Promega 10× buffer (Promega); and 1.25 Units Taq polymerase (Promega). The PCR reaction was run for 30 cycles (one minute at 95° C., one minute at 45° C. and one and a half minutes at 72° C.) followed by a 7 minute incubation at 72° C.

The PCR products were subsequently analyzed by Southern hybridization (Southern, *J. Mol. Biol.* 98:503, 1975; and Sambrook et al., ibid. ; which are incorporated herein by reference in their entirety) using the 1.9 kb Eco RI-Xho I fragment of pLJ4 that had been labeled by random priming using the Amersham MEGAPRIME kit (Arnersham) as a probe. One clone, G30, was shown to hybridize with the full length rat cDNA probe. The nucleotide sequence of G30 is shown in SEQ ID NO: 16.

EXAMPLE 5

CLONING OF A FULL LENGTH HUMAN GLUCAGON RECEPTOR cDNA

To identify a library that contained sequences encoding a human glucagon receptor, a series of libraries were screened by PCR using oligonucleotide primers ZC5433 and ZC5432 (SEQ ID NOS: 13 and 12, respectively) which were designed to contain sequences from clone G30 discussed above. Purchased and prepared human genomic and cDNA libraries from human liver, islet cell, HepG2 cell, brain and placenta were screened (Table 3). Individual 50 μl PCR reactions were set up using the DNA from each library at the volumes listed in Table 4, 20 pmole/μl each of ZC5433 and ZC5432 (SEQ ID NOS: 13 and 12, respectively), 0.25 mM of each deoxyribonucleic acid triphosphate, 5 μl of 10× Taq I buffer (Promega), 15 mM MgCl₂, 19.5 μl of distilled water and 0.5 μl of 5U/μl Taq I polymerase (Promega). In addition, reactions were set up containing pLJ4 as a positive control and no DNA as a negative control.

TABLE 3

Library and DNA Sources

| Library/DNA | Source |
| --- | --- |
| NIH hum liver cDNA | R. Bertolloti (NIH, Bethesda, Md.) |
| hum genomic #946203 | Stratagene |
| hum genomic #944201 | Stratagene |
| Hum. islet cell cDNA | Example 1C |
| λgt11 HBPG2 | prepared as described by Hagen et al. (U.S. |

TABLE 3-continued

Library and DNA Sources

| Library/DNA | Source |
| --- | --- |
| | Pat. No. 4,784,950, which is incorporated herein by reference in its entirety) |
| hum brain 1st strand cDNA | Clontech |
| hum placenta 1st strand cDNA | Clontech |
| hum liver 1st strand cDNA | Clontech |

TABLE 4

Volumes

| Library/DNA | Volume (diluted to 15 μl with water) |
| --- | --- |
| NIH hum liver cDNA | 1 μl of a 400 ng/μl stock solution |
| hum genomic #946203 | 15 μl of phage stock |
| hum genomic #944201 | 15 μl of phage stock |
| Hum. islet cell cDNA | 1 μl of a 1.2 μg/μl stock solution diluted 1:3 |
| λgt11 HEPG2 | 15 μl of phage stock |
| hum brain 1st strand cDNA | 1 μl of a 10 ng/μl stock |
| hum placenta 1st strand cDNA | 1 μl of a 10 ng/μl stock |
| hum liver 1st strand cDNA | 1 μl of a 10 ng/μl stock |

The PCR reactions were run for 30 cycles (one minute at 94° C., one minute at 50° C. and one and a half minute at 72° C.) followed by a 10 minute incubation at 72° C. The PCR products were subsequently analyzed by agarose gel electrophoresis. Only the NIH liver library generated a 320–410 bp band of equal size to that seen with the pLJ4 positive control.

The human liver library cloned into plasmid pcD2 (Chen and Okayama, *Mol. Cell. Biol.* 7:2745–2752, 1987) obtained from Dr. Roger Bertolloti (National Institutes of Health, Bethesda, Md.) was used to obtain a full length cDNA clone encoding the human glucagon receptor. The library was plated to obtain one million independent clones. The transformant colonies from each plate were scraped into 10 ml of LB-Amp (Sambrook et al., ibid.). The cells were spun down and the media were discarded. The cell pellets were resuspended in 4 ml of LB-Amp, 15% glycerol, and four one-milliliter aliquots were stored at –80° C. The first glycerol stock was titred, and 100 pools of 5000 colonies per plate were plated. After colonies had grown, each plate was scraped into 10 ml of LB-amp. An aliquot of the cells from each pool was removed for use in preparing plasmid DNA. The remaining cell mixtures were brought to a final concentration of 15% glycerol, aliquotted and frozen at –80° C. Plasmid DNA was prepared from each pool of cells, and the DNA was digested with RNAse (Boehringer Mannheim, Indianapolis, Ind.) according to the manufacturer's instructions. The RNAse reaction was terminated by a phenol/chloroform/isoamylalcohol (24:24:1) extraction, and the DNA was ethanol precipitated.

Aliquots of the resuspended plasmid DNA from each pool were combined into groups of 10 (ie., 1–10, 11–20, 21–30, 31–40, etc.). The plasmid DNA was diluted 1:20, and 1 μl of the DNA from each pool was used in a PCR reaction mixture identical to the reaction mixture described above. The reaction mixture was subjected to amplification under the conditions set forth above. Analysis of the PCR products by agarose gel electrophoresis showed that the pool 31–40 contained a 320–410 bp band of the same size as the positive control.

Plasmid DNA prepared from the original pools 31 through 40 were diluted 1:20 and 1 µl of each pool was used in a reaction mixture identical to the one described above. PCR amplification of the reaction mixtures using the conditions described above was carried out. Analysis of the PCR products by agarose gel electrophoresis showed that pool #40 gave a band size of pproximately 310–420 bp.

The concentration of plasmid DNA was roughly quantitated to be approximately 70 ng/µl by agarose gel electrophoresis of 1 µl of pool #40, which had been diluted 1:10. Seventy nanograms of pool #40 plasmid DNA was electroporated into *E. coli* strain DH10B cells at 2.3 kV, 400 Ω, 25 µF and resuspended in 1 ml SOC (Sambrook et al., ibid.). Three dilutions of the cells were prepared at $10^{-2}$, $10^{-3}$, and $10^{-4}$. One hundred microliters of each dilution was plated onto four plates. Colony numbers were estimated to be approximately 10,000 colonies per plate for the four plates containing cells from the $10^{-2}$ dilution and approximately 1000 colonies per plate for the four plates containing cells from the $10^{-3}$ dilution. Duplicate filter lifts were prepared from each of the four $10^{-3}$ plates and one of the $10^{-2}$ plates, designated pool #1 through pool #5. One filter from each duplicate set was laid on solid medium and allowed to grow until colonies formed. The colonies were then scraped and used to prepare plasmid DNA for PCR amplification. In addition, the three remaining plates of the $10^{-2}$ plates were scraped, and plasmid DNA was prepared from the cells.

The remaining filters were prewashed with 3× SSC+0.5% SDS at 65° C.with agitation for 12 hours to remove bacterial debris. The filters were then prehybridized in Ullrich's Buffer (Ullrich, *EMBO J.* 3:361–364, 1984)+50% formamide, 1% SDS overnight at 37° C. Clone G30 DNA that had been labeled using the Amersham MEGAPRIME kit (Amersham) according to the manufacturer's suggested conditions was boiled and added to hybridization solution (Ullrich's Buffer+50% formamide) to a final concentration of 6×10$^5$ cpm/ml. The filters were incubated overnight at 37° C.with agitation. After the overnight incubation, the probe solution was removed, and the filters were washed for five minutes at 65° C. in 2× SSC+0.1% SDS. Following the first wash, the filters were washed in the same solution for fifteen minutes at 65° C. followed by five minutes with shaking at room temperature. The last wash protocol was repeated two additional times. The filters were exposed to film overnight at room temperature. A single colony on plate #2, which corresponds to pool #2, was positive by hybridization to G30. This colony was picked and was streaked to obtain independent colonies. Plasmid DNAs prepared from several independent colonies were subjected to DNA sequence analysis. One clone, 40-2-2, was subjected to further sequence analysis and has been deposited 35 with the American Type Culture Collection (12301 Parklawn Dr., Rockville, Md. 20852) as an *E. coli* transformant under accession number 69055 on Aug. 21, 1992. A partial DNA sequence of clone 40-2-2 and its deduced amino acid sequence are shown as SEQ ID NOS: 17 and 18.

To confirm the presence of glucagon receptor sequences in the filter hybridization, PCR amplification reactions were carried out on each plasmid DNA preparation (plasmid DNA prepared from each duplicate filter and plasmid DNA prepared from each of the three $10^{-2}$ plates). The pooled plasmid DNAs were each diluted 1:20 in water, and 1 µl of each DNA was used as a template in a PCR reaction set up and run as described above. Agarose gel electrophoresis of the resulting PCR products showed that Pool #2 and three for the four pools of 10,000 contained PCR-generated bands for between 310 and 420 bp. The presence of the PCR-generated band in pool #2, which corresponds to plate #2, confirmed the presence of glucagon receptor DNA sequences.

F. Strategy for cloning the 5' sequence of a human glucagon receptor

Analysis of the partial CDNA sequence of clone 40-2-2 and the full length rat glucagon receptor cDNA sequence showed that the 40-2-2 clone was missing the amino-terminal sequence corresponding to approximately 25 amino acids. The 5' human glucagon receptor cDNA sequence was obtained using an adaptation of the method described by Frohman et al. (*Proc. Natl. Acad. Sci. USA* 85:8998–9002, 1988). Briefly, an oligonucleotide primer was designed such that the sequence hybridized to a sequence near the 5' end of the 40-2-2 coding sequence. The primer was hybridized to a G-tailed human liver first strand cDNA template, and the primer was extended toward the 5' terminus using Taq I DNA polymerase. A second poly d(C) primer was annealed to the G-tailed cDNA template to allow polymerase chain reaction amplification, subsequent clonings, sequencing and splicing to the coding sequence present in clone 40-2-2.

Three cDNA templates were prepared. A first template was a commercially available human liver first strand cDNA. A second and a third cDNA templates were prepared by synthesizing first strand cDNA from commecially available human liver mRNA (Clontech) using either an oligonucleotide containing sequences specific for the human glucagon receptor or using traditional oligo d(T) priming, respectively.

The second cDNA template was prepared by synthesis from human liver mRNA using oligonucleotide ZC5433 (SEQ ID NO: 13), which is specific for the human glucagon receptor coding sequence. A reaction mixture containing 2 µl of 1 µg/µl human liver mRNA, 8 µl of 20 pmole/jul ZC5433 (SEQ ID NO: 13) and 0.5 µl of 10 mM Tris, pH 7.4, 0.1 mM EDTA is incubated for 7 minutes at 68° C. followed by two minutes on ice. After the incubation, the reaction rnixture received 4 µl of 5× SUPERSCRIPT buffer (GIBCO-BRL), 1 µl of 200 mM dithiothreitol, 1 µl of a solution containing 10 mM of each dNTP, 1 µl of 0.25 µCi/µl α$^{32}$P-dCTP and 5 µl SUPERSCRIPT reverse transcriptase. The reaction was incubated for one hour at 45° C. Following the incubation, the reaction was incubated at 50° C.for 10 minutes. The reaction was terminated by the addition of 80 µl of TE. The RNA was hydrolyzed by the addition of 1 µl of 0.5M EDTA and 1 µl of KOH. The hydrolyzation reaction was incubated at 65° C.for five minutes. After incubation, the sample was diluted to 1 ml with 50 mM KOH, 0.1 mM EDTA, and the sample was passed over a CENTRICON 100 concentrator (Amicon, Danvers, Mass.). The column was washed with 1 ml 50 mM KOH, 0.1 mM EDTA. The concentrated cDNA was collected and neutralized with one-half volume of 100 mM HCI. The neutralized cDNA sample was ethanol precipitated, and the precipitate was resuspended in 26 µl of distilled water.

The third cDNA template was prepared by synthesis from human liver mRNA using a purchased oligo d(T) primer. A reaction mixture was prepared containing 2 µl of 1 µg/µl of human liver mRNA, 1 µl of 1 µg/µl oligo d(T)18 (New England Biolabs, Beverly, Mass.) and 5 µl of 10 mM Tris, pH 7.4, 0.1 mM EDTA. The cDNA synthesis was conducted using the conditions set forth for the synthesis described above.

The first strand cDNAs were then G-tailed. Reaction tubes were set up containing 4 µl of human liver first strand cDNA (QUICK CLONE; Clontech, Palo Alto, Calif.), 4 µl of human liver first strand cDNA from the ZC5433 (SEQ ID NO: 13) primer or 4 µl of human liver first strand cDNA from the oligo d(T) primer. Each reaction mixture received 22 µl of water, 8 µl of 5× Buffer (Promega), 4 µl of 10 mM dGTP and 2 µl of 15 U/µl terminal transferase, and the reactions were incubated for 30 minutes at 37° C. followed by a 10 minute incubation at 65° C. The reactions were then diluted to 90 µl with 10 mM Tris, pH 7.4, 1 mM EDTA and ethanol precipitated.

Second strand synthesis of all the G-tailed cDNAs was carried out identically. Each cDNA was first suspended in 50 µl of distilled water. Each cDNA then received 100 pmol of ZC4814 (SEQ ID NO: 20) in 5 µl. The cDNAs were annealed to the primer by heating each mixture to 68° C. for five minutes followed by a two minute incubation on ice. After the primer was annealed to the cDNA, each mixture received 20 µl of 5× Polymerase I buffer (Example 1), 1 µl of 100 mM dithiothreitol, 2 µl of a solution containing 10 mM of each dNTP, 2 µl of 0. 5 µCi/µl α$^{32}$P-dCTP, 1 µl of 3 U/µl E. coli DNA ligase (New England Biolabs), 5 µl of 7 U/µl E. coli DNA Polymerase I (Amersham). The reaction was incubated for five minutes at 22° C. followed by the addition of 1.5 µl of 2U/µl of RNase H (GIBCO-BRL) after which the incubation was resumed at 16° C. for two hours. The reaction was terminated by the addition of 200 µl of 10 mM Tris (pH 8. 0), 1 mM EDTA followed by 150 µl of water-saturated phenol and 150 µl of chloroform. The mixture was vortexed and then centrifuged for three minutes at 22° C. to separate the phases. The aqueous phase was removed and re-extracted with the phenol and chloroform as described above. After the second phenol-chloroform extraction, the aqueous layer was extracted with chloroform. The cDNA in the aqueous layer was precipitated by the addition of 5 µg mussel glycogen, 100 µl of 8M ammonium acetate and 300 µl isopropanol to selectively precipitate larger nucleic acids leaving the unincorporated oligonucleotide primers in the supernatant. The cDNA was pelleted by centrifugation and the pellet was washed with 70% ethanol followed by air drying. The cDNA pellet was resuspended in 15 µl of double-distilled water.

The double-stranded cDNAs were amplified in five parallel reactions using an oligonucleotide primer homologous to the 5' end of ZC4814 (SEQ ID NO: 20) and containing restriction endonuclease sites to facilitate subcloning, and an oligonucleotide primer specific for the very 5' end of the coding sequence present in the 40-2-2 clone. Each reaction mixture contained 5 µl 10× Taq I buffer, 3 µl of 25 mM MgCl$_2$, 5 µl of a solution containing 2.5 mM of each dNTP, 1 µl of double stranded cDNA, and 0.5 µl of Taq I polymerase (Promega). Distilled water was added to a final volume of 50 µl. The reaction was denatured for five minutes at 98° C. before the addition of 1 µl each of 10 pmole/µl of ZC5624 (SEQ ID NO: 21) and 20 pmole/µl of ZC4812 (SEQ ID NO: 19). Each sample was overlaid with 70 µl of mineral oil that had been held at 90° C. The reactions were amplified for 30 cycles (95° C. for 60 seconds, 57° C for 40 seconds, 72° C. for 60 seconds) followed by a 7 minute extension at 72° C.

Each PCR product was subjected to agarose gel electrophoresis, and the amplified fragments were each excised and subcloned into pCR1000 using the TA cloning kit (Invitrogen). Three clones from each ligation were selected and analyzed for the presence of insert by using the oligonucleotide primers ZC5624 (SEQ ID NO: 21) and ZC4812 (SEQ ID NO: 19) in independent PCR reaction mixtures each of which included an inoculum from a clone as the source of template DNA. The PCR reaction was carried out as described above with the exception that only 30 cycles of amplification were carried out. A single insert-positive clone from each original PCR reaction was subjected to DNA sequence analysis. Of the two clones shown to be containing the 5' human glucagon receptor coding sequence free of errors, one clone was selected to provide the 5' human glucagon receptor coding sequence. Clone 9A was digested with Eco RI and Kpn I to obtain a 551 bp fragment containing the 5' coding sequence of the glucagon receptor. The 3' glucagon receptor coding sequence was obtained as a 561 bp Kpn I-Bam HI fragment from 40-2-2. The Eco RI-Kpn I fragment and the 561 bp Kpn I-Bam HI fragment were ligated in the presence of Eco RI and Bam HI to prevent concatomerization. The product of the ligation, a 1112 bp fragment, was gel purified and designated 9A1. For convenience, fragment 9A1 was ligated into Eco RI-Bam HI digested pUC18. The ligation mixture was transformed into E. coli strain DH10b cells, and selected clones were analyzed for the presence of insert. One clone, 9A11, contained the insert.

The glucagon receptor coding sequence was constructed into a mammalian expression vector using plasmid p9All and clone 40-2-2 to obtain the complete glucagon receptor coding sequence. Plasmid p9A11 was digested with Pvu II and Bam HI to isolate the 967 bp fragment. Clone 40-2-2 was digested with Bam HI and Sac I to isolate the 828 bp fragment containing the 3' human glucagon receptor coding sequence. The mammalian expression vector pHZ1 was linearized by digestion with Eco RI, and the ends were blunted using T4 DNA polymerase. The blunt-ended linearized vector was then digested with Sac I. The 967 bp Pvu II-Bam HI fragment and the 828 bp Bam HI-Sac I fragment were ligated with the blunt-Sac I digested pHZ1 vector.

Plasmid pHZ1 is an expression vector that may be used to express protein in mammalian cells or in a frog oocyte translation system from mRNAs that have been transcribed in vitro. The pHZ1 expression unit comprises the mouse metallothionein-1 promoter, the bacteriophage T17 promoter flanked by multiple cloning banks containing unique restriction sites for insertion of coding sequences, the human growth hormone terminator and the bacteriophage T7 terminator. In addition, pHZ1 contains an E. coli origin of replication; a bacterial beta lactamase gene; a mammalian selectable marker expression unit comprising the SV40 promoter and origin, a neomycin resistance gene and the SV40 transcription terminator.

The pHZ1 plasmid containing the glucagon receptor cDNA sequence in the correct orientation relative to the promoter was designated pLJ6'. The insert and vector junctions were sequenced to confirm the presence of correct sequence. Plasmid pLJ6' has been deposited with the American Type Culture Collection (12301 ParkLawn Drive, Rockville, Md. 20852) under Accession Number 69183 on Jan. 15, 1993. The DNA sequence and deduced amino acid sequence of the glucagon receptor cDNA present in pLJ6' is shown in SEQ ID NO: 24 and SEQ ID NO: 25.

EXAMPLE 6

CLONING OF A GLUCAGON RECEPTOR cDNA FROM HUMAN ISLET CELLS

In addition to cloning a glucagon receptor from human liver cells, a glucagon receptor cDNA was obtained from a human islet cell library. An aliquot of the human islet cell cDNA library (Example 1.C.) was subjected to PCR amplification using oligonucleotide ZC5763 (SEQ ID NO: 22), which is a sense oligonucleotide containing an Eco RI site flanked by sequences from the 5' untranslated sequence of the human glucagon receptor cDNA and oligonucleotide ZC5849 (SEQ ID NO: 23) which is an antisense oligonucleotide containing an Xho I site flanked by sequences from the 3' untranslated sequence of the human glucagon receptor cDNA. The inclusion of the restriction sites in the oligonucleotide primers facilitated the directional cloning of the resulting PCR products into a suitable plasmid vector. A PCR reaction mixture was set up containing 4 µl of the islet cell cDNA library (Example 1.C.), 8 µl of 10× Promega PCR Buffer (Promega), 20 pmols of ZC5763 (SEQ ID NO: 22), 20 pmols of ZC5849 (SEQ ID NO: 23), 1 µl of a solution containing 20 mM of each deoxyribonucleotide and 46. 5 µl of water. The mixture was heated to 95° C. for three minutes, the heat was then reduced to 80° C. for three minutes. The mixture was held at 80° C. until ready for use. To start the reaction, the 20 µl of an enzyme mix comprising 2 µl of 10× Promega PCR Buffer (Promega), 2 µl of 5 U/µl Taq I polymerase (Cetus) and 16 µl of water was added to the reaction mixture. The reaction was overlaid with 50 µl of mineral oil (Sigma), and the reaction was subjected to thirty cycles (95° C. for one minute, 55° C. for one minute, 72° C. for two minutes and fifteen seconds in which the 72° C. incubation was increased three seconds every cycle) followed by a ten minute incubation at 72° C. After the final 72° C. incubation, the reaction was held at 4° C. Agarose gel electrophoresis of a 10 µl aliquot of the PCR product demonstrated the presence of an approximately 1.8 to 1.9 kb fragment. Based on the human glucagon receptor cDNA present in pLJ6', a fragment of approximately 1846 bp was expected.

The PCR reation was extracted with chloroform, followed by two phenol:chloroform extractions and a final chloroform extraction. After the final extraction, 5 µl of 4 µg/µl glycogen carrier (Boerhinger Mannheim Corporation) was added, and the mixture was precipitated in the presence of ammonium acetate and ethanol. The DNA was pelleted by centrifugation, and the pellet was washed with 70% ethanol. The DNA pellet was reconstituted in water and digested with Xho I and Eco RI. The DNA was gel purified and subcloned into plasmid pBLUESCRIPT SK+ (Stratagene Cloning Systems) that had been linearized with Xho I and Eco RI. The ligation mixture was transformed into E. coli strain DH10B cells (GIBCO-BRL). Plasmid DNA was prepared from selected transformants, and the DNA was subjected to restriction enzyme and Southern blot analysis. The clones were compared to the human glucagon receptor cDNA insert present in pLJ6'. On the basis of diagnostic restriction enzyme digestion, selected clones were subjected to sequence analysis. Sequence analysis of showed that one clone, pSLIGR-1, contained glucagon receptor coding sequences. The coding region of pSLIGR-1 contained three nucleotide changes in the glucagon receptor coding region as compared to the liver cDNA present in pLJ6'. One of the nucleotide changes was a silent mutation, the remaining two resulted in conservative amino acid changes as shown in Table 5. Analysis of the changes suggests that they could be the result of polymorphic differences representing allelic variations.

TABLE 5

| Amino Acid Number | Amino Acid based on Liver cDNA sequence | Amino Acid based on Islet cell cDNA sequence |
| --- | --- | --- |
| 184 | Phe | Leu |
| 265 | Ser | Gly |

EXAMPLE 7

CLONING OF A HUMAN GLUCAGON RECEPTOR GENE

To obtain a human glucagon receptor genomic clone, two libraries of genomic DNA were screened using the human glucagon receptor cDNA as a probe. An amplified human λFIX II caucasian male placenta genomic library and an amplified human lung λFIX genomic library (both libraries were obtained from Stratagene Cloning Systems, Catalog numbers 946203 and 944201, respectively) were screened for the human glucagon receptor gene.

The amplified human lung genomic library was titred and approximately 4×10$^4$ plaque forming units (pfu) were plated with E. coli strain LE392 cells (Stratagene Cloning Systems) on each of thirty 150 mm diameter plates. An additional ten plates were plated with E. coli strain LE392 cells and approximately 6×10$^4$ pfu per plate. The plates were allowed to incubate overnight at 37° C., and thirty plates were selected for screening.

Duplicate filters were prepared for each of the thirty plates. Each filter was prepared by overlaying a plate with a HYBOND nylon membrane (Amersham) according to the procedure recommended by the manufacturer.

The filters were lifted from the plates, and the cells were lysed in 1.5M NaCl, 0.5M NaOH for five minutes at room temperature. The filters were neutralized for five minutes in 1M Tris-HCl (pH 7.5), 1.5M NaCl, and the filters were fixed with 1200 µjoules of UV energy in a STRATALINKER (Stratagene Cloning Systems). After the filters were fixed, the filters were prewashed three time in 0.25× SSC, 0.25% SDS, 1 mM EDTA at 65° C. After prewashing, the filters were split into 6 batches of 10 filters that were prehybridized in a prehybridization solution (5× SSC, 5× Denhardt's solution, 0.2% SDS, 1 mM EDTA) that was filtered through a 0.45 µm filter and to which had been added a final concentration of 100 µg/ml of heat-denatured salmon sperm DNA immediately before use. The filters were prehybridized at 65° C. overnight.

The human glucagon receptor cDNA from p40-2-2 was random-primed using the Amersham MEGAPRIME kit (Amersham) using the method recommended by the manufacturer. The prehybridization solution from each batch of filters was replaced with fresh prehybridization solution containing 28.5×10$^6$ cpm of probe. The filters were hybridized at 65° C. for twenty hours. After hybridization, the hybridization solution was removed, and the filters were rinsed four or five times each in a wash solution containing 0.25× SSC, 0.2% SDS,1 mM EDTA at room temperature. After rinsing, the filters were washed in eight consecutive washes at 65° C. in the wash solution, followed by a final wash at 70° C. After the 70° C. wash, the filters were exposed to autoradiograph film (XAR-5; Eastman Kodak Co. ; Rochester, N.Y.) for four days at −70° C. with an intensifying screen.

Examination of the autoradiographs revealed the presence of four regions of hybridization with the radiolabeled probe.

A plug of agar from each of the four regions was picked for purification. Each agar plug was soaked overnight in 1 ml of SM (Maniatis et al., eds., *Molecular Cloning: A Laboratory Manual*, Cold Spring Harbor, N.Y., 1982; which is incorporated herein in its entirety), 1% chloroform. After the overnight incubation, the phage from each plug were diluted 1:1,000 SM. Aliquots of 5, 25 and 50 µl were plated with *E. coli* strain LE392 cells. The plates were incubated and single lifts were prepared from the plates from the 5 and 25 µl platings. The filters were prepared, prehybridized and hybridized and washed as described above. The filters were exposed to autoradiograph film.

Examination of the autoradiographs revealed positively labeled regions from each of the four clones. A total of ten agar plugs were picked from positive areas representing at least two positive areas for each of the original clones. The agar plugs were treated as described above. The phage from each agar plug were diluted 1:10,000 in SM. Aliquots of 2.5 and 10 µl were plated with *E. coli* strain LE392 cells. The plates were incubated and single lifts were prepared from the plates from the plates having suitably separated plaques.

Filters were prepared and hybridized as described above. Autoradiographs of the filters revealed areas of exposure corresponding to distinct plaques. Twelve positive plaques were picked, representing at least one clone from each of the four original positives. One plaque from each plate was selected for further analysis.

Agar plugs from phage clones 2-2-1, 3-1-1, 14-2-1 and 11-2-1 were treated as described above. The phage were diluted 1:1000 in SM and inoculated into a culture of *E. coli* strain LE392 cells. Double-stranded DNA was prepared essentially as described by Grossberger (*Nuc. Acids Res.* 15: 6737, 1987; which is incorporated by reference herein in its entirety). The double-stranded DNA was digested with Xba I to liberate the genomic insert. Agarose gel electrophoresis demonstrated that clones 2- 2-1 and 11-2-1 contained and 9 kb Xba I insert, clone 14-2-1 contained a 15 kb insert and 3-3-1 contained a 13 kb insert. Southern blot analysis of Xba I digested and Xba I-Bam HI digested clones showed that the human glucagon receptor cDNA hybridized to the fragments shown in Table 6.

TABLE 6

| New Clone Number | Original Clone Number | Hybridizing Xba I fragments | Hybridizing Xba I-Bam HI fragments |
| --- | --- | --- | --- |
| Clone 1 | 2-2-1 | ~9 kb | 4.2 kb, 1.9 kb |
| Clone 6 | 11-2-1 | ~9 kb | 4.2 kb, 1.9 kb |
| Clone 2 | 14-2-1 | ~15 kb | 4.2 kb, 1.9 kb |
| Clone 5 | 3-3-1 | ~13 kb | 1.6 |

Clones 11-2-1 and 14-2-1 were selected for further analysis. Clone 2-2-1 appeared to be identical to clone 11-2-1 and was not subjected to further analysis. For convenience, the clone names were changed as reflected in Table 6. Double-stranded DNA was prepared from each phage clone for subcloning into a plasmid vector using the method essentially described by Maniatis. The DNA was digested with Xba I, gel-purified and subcloned into plasrnid pBLUE-SCRIPT SK+ (Stratagene Cloning Systems) that had been linearized by digestion with Xba I and treated with calf alkaline phosphatase to prevent recircularization. The ligation mixtures were electroporated into ELECTROMAX DH10B cells (GIBCO-BRL) in a BioRad GENEPULSER (Bio-Rad Laboratories; Richmond, Calif.) at 400 ohms, 25 µfarads and 2.3 kVolts. Plasmid DNA was prepared from selected transformants. Clones containing genomic inserts from clones 6 and 2 were named pSLHGR6 and pSLHGR2, respectively. Clones pSLHGR6 and pSLHGR2 were sequenced. Sequence analysis and comparison with the coding region of the human glucagon receptor cDNA revealed the presence of 12 exons containing the coding region. Chromosomal location analysis was carried out on metaphase chromosome spreads prepared essentially as described by Durnam et al. (*Mol. Cell. Biol.* 8:1863–1867, 1988, which is incorporated by reference herein in its entirety) using a biotinylated human glucagon receptor gene probe and a chromosome 17-specific centromere probe. Denaturation of chromosomes, hybridization and single color detection were performed essentially as described by Pinkel et al. (*Proc. Natl. Acad. Sci USA* 83:2934–2938, 1986, which is incorporated by reference herein in its entirety) and modified by Kievits et al. (*Cytogenet. Cell Genet.* 53:134–136, 1990, which is incorporated by reference herein in its entirety) except that the hybridization was performed in 65% (vol/vol) formamide/10% dextran sulfate/ 2× SSC and the post hybridization washes were with 65% formamide/2× SSC at 42° C. and then 0.1×SSC at 55° C. as described by Palrniter et al. (*Proc. Natl. Acad. Sci. USA* 89:6333–6337, 1992, which is incorporated by reference herein in its entirety). The $q^{25}$ location was confirmed by DAPI staining some hybridized metaphase spreads as described by Testa et al. (*Cytogenet. Cell Genet.* 60:247–249, 1992; which is incorporated by reference herein in its entirety). The DAPI staining produced a Q-band-like pattern.

The amplified human placenta genomic library (Stratagene) was screened unsuccessfully for a glucagon receptor gene using the method essentially described above. Briefly, the library was titred, and *E. coli* strain LE392 cells and approximately $5 \times 10^4$ pfu were plated on each of 30 150-mm plates. In addition, 11 150-mm plates were each plated with approximately 105 pfu and *E. coli* strain LE392 cells. The plates were allowed to incubate overnight at 37° C., and thirty-eight plates were selected for screening.

Nylon filter lifts were prepared, washed and prehybridized as described above. The human islet glucagon receptor cDNA fragment, G30 (Example 4) was random-primed using the Amersham MEGAPRIME kit (Amersham) using the method recommended by the manufacturer. The prehybridization solution from each batch of filters was replaced with fresh prehybridization solution containing $1.1 \times 10^6$ cpm of probe. The filters were hybridized at 65° C. for overnight. After hybridization, the hybridization solution was removed, and the filters were rinsed four or five times each in a wash solution containing 0.25× SSC, 0. 25% SDS, 1 mM EDTA at room temperature. After rinsing, the filters were washed in eight consecutive washes at 65° C. in the wash solution. After the 70° C. wash, the filters were exposed to autoradiograph film (XAR-5; Eastman Kodak Co.) for four days at –70° C. with an intensifing creen.

Examination of the autoradiographs revealed no convincing positive signals; however, seven areas corresponding to weakly labeled regions were picked for further analysis. The clones were subjected to a secondary screen as described above, but autoradiographs of the secondary screen showed no labeled areas. These clones were not pursued.

EXAMPLE 8

EXPRESSION OF A GLUCAGON RECEPTOR cDNAs IN MAMMALIAN CELLS

A. Expression of a Rat Glucagon Receptor in BHK570 cells

Plasmid pLJ4 was co-transfected with plasmid pLJ1 into BHK570 cells (deposited with the American Type Culture Collection under Accession No. 10314) using the calcium phosphate method essentially as described by Graham and Van der Eb (*Virology* 52:456, 1973, which is incorporated by reference herein in its entirety). Plasmid pLJ1 was derived from plasmid p416, which comprises the Adenovirus 5 ori, SV40 enhancer, Adenovirus 2 major late promoter, Adenovirus 2 tripartite leader, 5' and 3' splice sites, the DHFR$^r$ cDNA, the SV40 polyadenylation signal and pML-1 vector sequences (Lusky and Botchan, *Nature* 293:79–81, 1981). The Eco RI-Xba I DHFR expression unit from p416 was ligated into pUC18 that had been linearized by digestion with Eco RI and Xba I to construct plasmid pLJ1. The transfected cells were grown in growth medium (Dulbecco's modified Eagle's medium (DMEM) containing 10% fetal calf serum, 1× PSN antibiotic mix (GIBCO BRL 600–5640), and 2.0 mM L-glutamine). After a few days in non-selective growth medium, the growth medium was replaced with selection medium (growth medium containing 250 mM methotrexate (MTX)). The cells were split and diluted 1:20 and 1:50 in the selection media into 10-cm plates. After 7–10 days of selection in 250 mM MTX, the colonies were picked using cloning cylinders into wells of 24-well plates. The resulting clones were tested for the ability to bind glucagon as described above (Example 3). Glucagon binding was also carried out on whole cells by plating 2×10$^5$ cells of each clone into the wells of a 24-well plate. The plates were incubated for 72 hours at 37° C. in 5% CO$_2$. Glucagon binding was carried out as described in Example 3, with the exception that after the final PBS wash, the cells were removed from the wells by trypsinization into tubes. The tubes were counted in a gamma counter. Those cells having the highest number of counts and therefore capable of binding the most glucagon were selected for further characterization. The selected transformants were also assayed for glucagon-mediated cAMP response as described in Example 8D and glucagon-mediated intracellular calcium response as described in Example 8E. Glucagon binding assays were also carried out on membrane preparations from the transfectants as described below.

B. Glucagon binding using Membrane Preparations

Membranes from the pLJ4 BHK transfectants were compared with rat liver membrane preparations for the ability to bind $^{125}$I-glucagon. Membranes were prepared essentially described by Rodbell et al. (*J. Biol. Chem.* 246:1861–1871, 1971, which is incorporated by reference herein in its entirety). Two batches of liver membranes were each prepared from approximately 80 gm of liver from 12 to 16 decapitated young female rats. The livers were removed quickly and placed into an iced beaker. The livers were separated into ten-gram portions. The portions were minced with scissors, and connective tissue was removed during the mincing procedure. The portions were separately homogenized in a Dounce homogenizer. To each portion, 25 ml of Medium (Table 2) was added to the minced tissue in the homogenizer, and the tissue was homogenized in an ice bucket with eight vigorous strokes of the loose pestle. After homogenization, the homogenates were pooled into 450 ml of cold Medium (Table 2). The pooled homogenates were stirred for 3 minutes and filtered through two layers of cheesecloth followed by filtering through four layers of cheesecloth. The homogenates were then centrifuged for 30 minutes at 1500 ×g at 4° C. The supernatants were discarded, and the pellets were pooled into a clean Dounce homogenizer. The pellets were resuspended with three gentle strokes of the loose pestle. The resuspended pellets were decanted into a 250 ml graduate containing 62 ml of 69% Sucrose Solution (Table 2). Distilled water was added to a final volume of 110 ml, and the mixture was thoroughly mixed and kept cold. The concentration of the solution was adjusted to 44.0%+/−0.1% using 69% sucrose or water as measured by a refractometer (Bausch & Lomb, Rochester, N.Y.). The sucrose suspension was distributed equally into 25×89 mm ultracentrifuge tubes. Each suspension was carefully overlaid with 20 ml of 42.3% Sucrose Solution (Table 2), and the suspensions were centrifuged for 150 minutes at 24,000 rpm in an SW28 rotor (Sorvall, Dupont Company, Wilmington, Del.) at 4° C.

After centrifugation, the floating material from each tube was removed by aspiration into a 10 ml syringe through an 18-gauge needle. The material from each tube was pooled and resuspended in about 10 ml of Medium (Table 2) by drawing and expelling the mixture through the needle into a centrifuge tube. The tube was filled with Medium (Table 2) and centrifuged for 15 minutes at 15,000 RPM in an SS-34 rotor (Sorvall).

The supernatant was carefully decanted and discarded. The pellet was resuspended in Medium (Table 2) and was diluted 1:1000 with distilled water. The absorbance was read in 1 cm cuvettes to determine protein concentration. Protein concentration was determined using the formula:

$$\frac{A_{224} \text{ nm} - A_{236} \text{ nm}}{6.45} \times \text{dilution factor} = \text{mg protein/ml}$$

The membrane preparation was aliquoted, quick frozen in a dry ice/ethanol bath and stored at −80° C.

Membranes were prepared from BHK transfectants that had been grown to confluency in 150-mnm plates in selection medium. Two plates of confluent transfectants were rinsed two times with cold phosphate buffered saline (PBS; Sigma Chemical Co., St. Louis, Mo.), and 10 ml PBS containing 1 mM PMSF was added to each plate. The cells from each plate were scraped into the PBS solution, and the cells from each plate were each transferred into fresh tubes. Each plate was rinsed with 5 ml PBS containing 1 mM PMSF, and the rinses were pooled with their respective cells. The cells were centrifuged at 2,000 rpm in a table top centrifuge at 4° C. The supernatants were discarded, and the cells were resuspended in 30 ml 5 mM Hepes, 1 mM PMSF, pH 7.5. The cells were incubated on ice for 15 minutes followed by centrifugation at 47,800 ×g at 4° C. Each pellet was resuspended in a solution of PBS containing 1M PMSF, aliquotted and frozen at −80° C.

Figure 3:
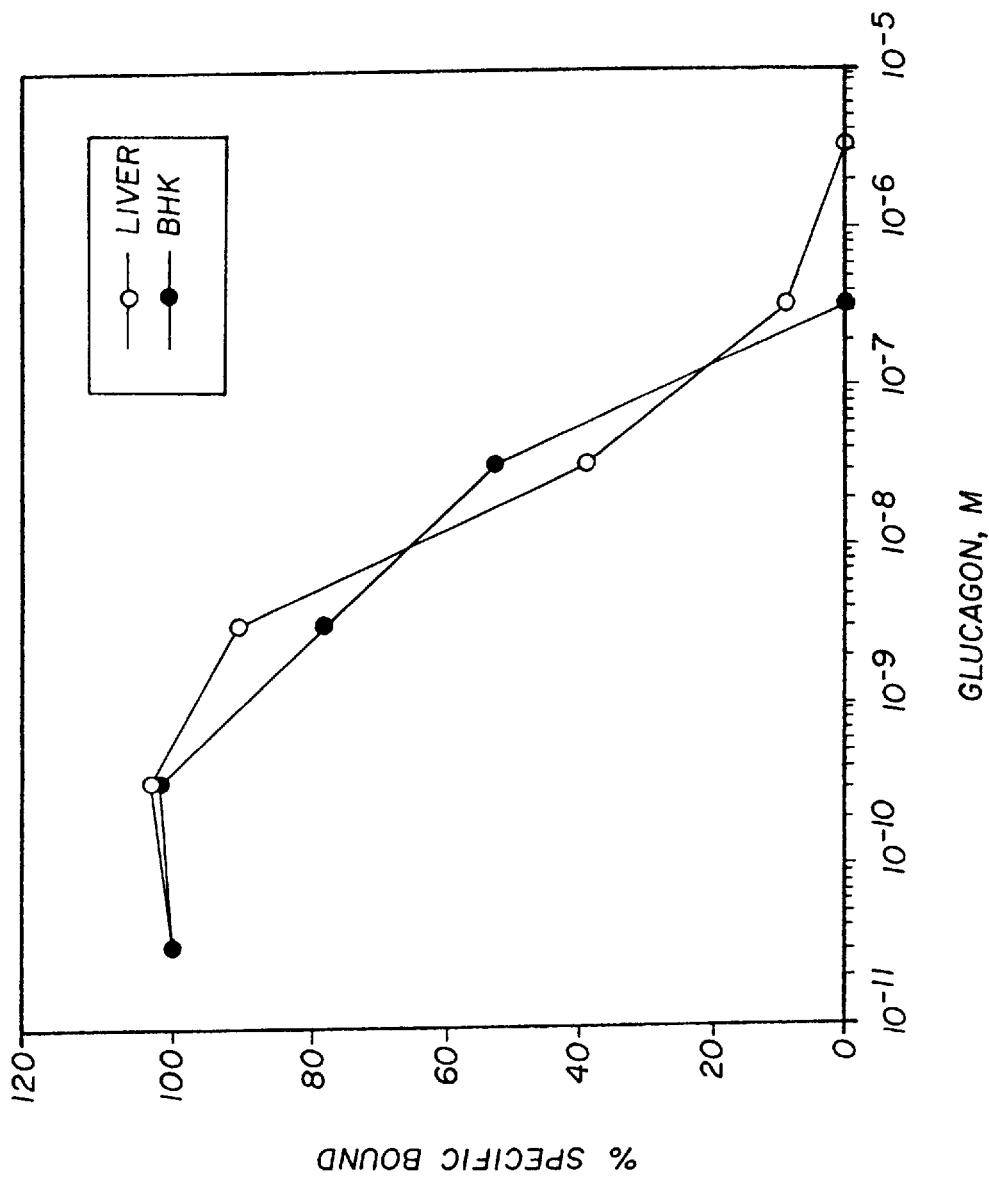
FIG. 3 graphically depicts the binding of $^{125}$I-glucagon to glucagon receptors.
Figure 4:
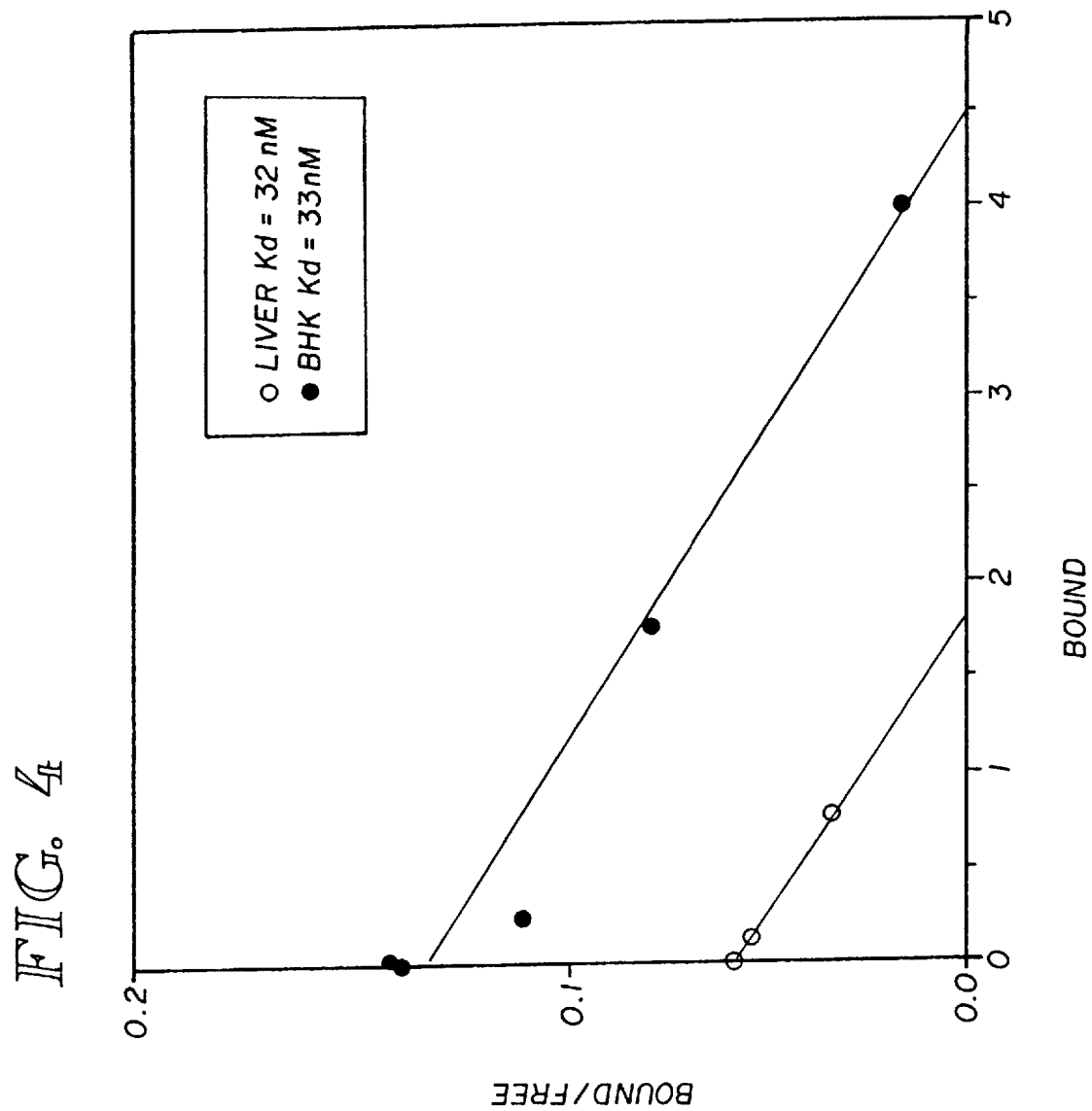
FIG. 4 is a Scatchard analysis of the apparent Kd for glucagon receptors.

Competition analysis using glucagon binding assays was conducted on the rat liver and BHK transformant membrane preparations. Briefly, reaction tubes containing 20 µl of glucagon from 10$^{-11}$M to 10$^{-6}$M diluted in 10 mM HOAc or 20 µl of BSA were set up. To each tube 100 µl of 2× binding buffer; 20 µl of $^{125}$I-glucagon (Amersham); 20 µl of 1 mM NaHCO$_3$; 20 µl 10 mM HOAc, 0.5% BSA (Novo Nordisk N/A, Bagsvaerd, Denmark); and 40 µl of distilled water were added. The binding reaction was initiated by the addition of 20 µl of a membrane preparation to the reaction tubes. The reactions were incubated for 30 minutes at 30° C. The membranes were pelleted by centrifugation in a microfuge at high speed for 10 minutes at 4° C. The supernatants from each sample were aspirated, and the pellets were counted. Competition with unlabeled glucagon yielded nearly identical sigmoidal curves for glucagon binding (FIG. 3). By Scatchard analysis (Scatchard, *Ann N.Y. Acad. Sci.* 51:660–672, 1949, which is incorporated by reference herein in its entirety), the apparent Kd is 50 nM for the cloned receptor and 49 nM for rat liver membranes (FIG. 4).

The specificity of the receptor encoded by pLJ4 was tested for the ability of related peptide hormones to compete for $^{125}$I-glucagon binding. Micromolar amounts of glucagon and related peptides (Table 7) were each added with $^{125}$I-glucagon to membrane preparations of the pLJ4 transfectants in the binding assay described above. Only native glucagon and the antagonist des-His$^1$[Glu$^9$]glucagon amide were able to compete with the $^{125}$I-glucagon for binding to the membranes.

TABLE 7

| | |
|---|---|
| 1 μM | human glucagon (Sigma) |
| 1 μM | des-His$^1$[Glu$^9$]glucagon amide (synthesized on an Applied Biosystems 431A peptide synthesizer using RINK AMIDE MBHA resin (Bachem Bioscience Inc., Philadelphia, Penn.)) |
| 200 μM | human glucagon-like peptide (GLP) (Sigma) |
| 20 μM | porcine vasoactive intestinal peptide (VIP) (Sigma) |
| 1 μM | salmon calcitonin (Sigma) |
| 1 μM | porcine secretin (Sigma) |
| 1 μM | bovine parathyroid hormone (PTH) (Sigma) |

C. Expression of a Rat Glucagon Receptor in COS-7 cells

The ability of COS-7 cells transfected with pLJ4 to be stimulated by glucagon to increase cAMP levels was assessed using an Amersham SPA kit (Amersham) as described below (Example 8D). The assay showed that the glucagon-stimulated pLJ4 transfectants accumulated approximately five-fold more cAMP than control vector only-transfected COS-7 cells. The related peptides secretin, VIP, PTH, GLP and calcitonin were each added to transfectants at concentrations of 100 nM to 1000 nM and assayed for their ability to induce cAMP levels. The results of the assays showed that none of the related peptides were capable of inducing significant increases in cAMP levels.

D. Luciferase and Adenylate Cyclase Activity Assays on Whole Cells

The rat glucagon receptor cDNA was expressed in a BHK570 cell line stably transfected with ZK6, an expression unit comprising a promoter containing at least one cyclic AMP response element, the luciferase cDNA and the hGH terminator. This cell line permits the measurement of luciferase activity, adenylate cyclase activity and intracellular calcium concentrations in response to glucagon binding to its receptor.

The proenkephalin cyclic AMP response element (CRE) in plasmid ZK6 was obtained from Zem233. Zem233 was derived from plasmids Zem67 and Zem106. Plasmid Zem106 was constructed from the precursor Zem93. To construct Zem93, a Kpn I-Bam HI fragment comprising the MT-1 promoter was isolated from MThGH111 (Palmiter et al., *Science* 222:809–814, 1983) and inserted into pUC18. Plasmid Zem93 was then digested with Sst I and re-ligated to generate plasmid Zem106, in which approximately 600 bp of sequence 5' to the MT-1 promoter were eliminated.

A proenkephalin CRE was inserted into the 5' end of the SV40 promoter in Zem 106 by first digesting Zem106 with Eco RI and Sst I to isolate the vector-containing fragment. Oligonucleotides ZC982 and ZC983 (SEQ ID NOS: 3 and 4, respectively) were designed to encode, when annealed, an proenkephalin CRE from nucleotides −71 to −133 (Comb et al., *Nature* 323:353–356, 1986) flanked by a 5' Eco RI site and a 3' Sst I site. Oligonucleotides ZC982 and ZC983 (SEQ ID NOS: 3 and 4, respectively) were kinased, annealed and ligated with the linearized Zem106 to obtain plas mid Zem224.

Plasmid Zem67 was obtained by first digesting pIC19R (Marsh et al., *Gene* 32:481–486, 1984) with Sma I and Hind II 1. The ori region of SV40 from map position 270 (Pvu II) to position 5171 (Hind III) was then ligated to the linearized pICl9R to produce plasmid Zem67. The Hind III-Bam HI neomycin resistance gene-SV40 terminator fragment from plasmid pSV2-neo (American Type Culture Collection Accession No. 37149) was inserted into Hind III-Bgl II digested Zem67 to obtain Zem220.

The SV40 promoter-neomycin resistance gene-SV40 terminator expression unit from plasmid Zem220 was isolated as an Eco RI fragment. Plasmid Zem224 was digested with Eco RI and treated with calf alkaline phosphatase to prevent recircularization. The neomycin expression unit and the linearized Zem224 were ligated. A plasmid containing the SV40 promoter proximal to the CRE was designated Zem233.

Plasmid Zem233 was modified to insert an additional CRE sequence, a TATA box, and a portion of the lacZ coding and poly(A) sequences immediately 3' to the proenkephalin CRE sequence such that the resulting expression unit was in the opposite orientation relative to the neomycin resistance expression unit present in Zem233. Plasrnid Zem233 was linearized by digestion with Sst I and Bam HI. Oligonucleotides ZC3509 and ZC3510 (SEQ ID NOS: 5 and 6, respectively) were designed such that, when annealed, the resulting duplex encodes the a glycoprotein CRE (Delegeane et al., *Mol. Cell. Biol.* 7:3994–4002, 1987) with a 5' Sst I adhesive end and a 3' Eco RI adhesive end. The oligonucleotides were annealed according to standard procedures. The thymidine kinase TATA box was obtained as an Eco RI-Pst I fragment spanning nucleotides −79 to +18 of the thymidine kinase gene (McKnight, *Cell* 31:355–366, 1982). The 3' sequence of the lacZ gene and its associated poly(A) sequence were obtained as a Pst I-Bam HI fragment from plasmid pLacF (obtained from Jaques Peschon, Immunex Corp., Seattle, Wash.), which contains the lacZ coding region and mouse protamin terminator sequence cloned into the pUC18 vector. The Sst I-Bam HI linearized Zem233, the Sst I-Eco RI ZC3509/ZC3510 adapter, the Eco RI-Pst I TATA box fragment and the Pst I-Bam HI lacZ sequence were ligated. A plasmid containing the expression unit in the correct orientation relative to the neomycin resistance gene expression unit of Zem233 was designated KZ5.

The luciferase gene and human growth hormone (hGH) terminator sequences were used to replace the lacZ coding and poly(A) sequences present in KZ5. The luciferase gene was initially obtained from plasmid α-1681uc (Delegeane et al., *Mol. Cell. Biol.* 7:3994–4002, 1987;and deWet et al., *Mol. Cell. Biol.* 7:725–737, 1987) as a 1.7 kb Xho I-Xba I fragment.

The hGH terminator was obtained as an Xba I-Sal I fragment from Zem219b (deposited as an *E. coli* transformant with the American Type Culture Collection (Rockville, Md.) under Accession No. ATCC 68979). The luciferase gene and hGH terminator sequences were subcloned into Xho I-Sal I linearized pIC19H (Marsh et al., ibid.) for convenience. The resulting plasmid, KZ8, was digested with Xho I and Sal I to isolate the luciferase-hGH terminator sequences. Plasmid KZ5 was digested with Sal I to isolate the vector containing fragment and was treated with calf alkaline phosphatase to prevent recircularization. The Xho I-Sal I luciferase-hGH terminator fragment was ligated with the Sal I-digested KZ5. A plasmid containing the luciferase-hGH terminator in the proper orientation relative to the promoter was designated KZ6.

Plasmid KZ6 was transfected into BHK570 cells (deposited with the American Type Culture Collection under Accession No. 10314) using the calcium phosphate precipitation method essentially as described by Graham and Van der Eb (*Virology* 52:456, 1973, which is incorporated by reference herein in its entirety). The transfected cells were grown in growth medium (Dulbecco's modified Eagle's medium (DMEM) containing 10% fetal calf serum, 1× PSN antibiotic mix (GIBCO-BRL), and 2.0 mM L-glutamine). After a few days in non-selective growth medium, the growth medium was replaced with G418 selection medium (growth medium containing 500 μg/ml of G418). The cells were then allowed to grow to confluency after which they are trypsinized and plated at limiting dilution into the wells of 96-well plates. The cells were grown for one to two weeks in G418 selection media. Clones from wells containing single colonies were assayed for the ability to respond to forskolin in the luciferase assay described below. Forskolin elevates the cellular cAMP level and thus the associated cAMP-dependent biological response pathways in a receptor-independent manner. A clone capable of responding to forskolin was designated BHK/KZ6-19-46.

BHK/KZ6-19-46 cells were co-transfected with pLJ4 and pLJ1 or with pZCEP and pLJ1 (pZCEP transfectants were used as negative controls) as described above using calcium phosphate-mediated transfection. Transfectants were selected in 250 nM methotrexate as described previously.

Transfectants were assayed in triplicate for the induction of the CRE-luciferase response by selected agonists. Six random pLJ4 transfectants were assayed, and random pZCEP transfectants were assayed (negative controls). Microtiter assay plates were set up such that each well contained $2\times10^4$ cells in 100 μl of selection medium, and the cells were grown overnight. The agonists were prepared in selection medium, at the 2× final assay concentration listed:

1 μM glucagon
200 nM glucagon-like peptide (GLP)
20 nM vasoactive intestinal peptide (VIP)
100 nM calcitonin (CT)
20 μM forskolin (CalBiochem, San Diego, Calif.)

Induction was initiated by the addition of 100 μl for each 2× solution in triplicate sample wells. Uninduced levels were determined in triplicate wells to which 100 μl of DMEM containing 10% fetal calf serum was added. The plates were incubated for four hours at 37° C., 5% $CO_2$ to allow induction of luciferase production.

Following induction, the medium was removed, and the wells were washed once with 200 μl/well PBS. After the wash 25 μl of 1× Cell Culture Lysis Reagent (Luciferase Assay System, Promega Corp., Madison, Wis.) was added to each well, and the plates were incubated for 15 minutes at room temperature. The plates were transferred to a Labsystems Luminoskan microtiter lumininometer (Labsystems Inc., Morton Grove, Ill.) which added 40 μl of Luciferase Assay Substrate (Luciferase Assay System, Promega), mixed the reaction for three seconds and integrated the luciferase signal for two seconds per well. The fold induction of luciferase for each agonist was calculated as follows:

$$\text{Fold induction} = \frac{\text{Induced signal} - \text{Uninduced signal}}{\text{Uninduced Signal}}$$

One pLJ4 transfectant clone, KZ6/rGR-DHFR-2, showed a 6–10 fold induction of luciferase by glucagon but was not induced by GLP, VIP or CT.

The cAMP response of the transfectant clone KZ6/rGR-DHFR-2 to glucagon and forskolin was also assayed by radioimrnmunoassay using the cAMP [$^{125}$I] scintillation proximity assay system (Amersham) using the manufacturer's directions. Briefly, 100 μl of $2\times10^5$ cells per ml KZ6/rGR-DHFR-2 cells were plated into the wells of a multi-well culture dish and grown overnight in selection media. Glucagon and forskolin were prepared in DMEM, 10% fetal calf serum, 10 μM IBMX at 0.0001–1000 nM and 25 μM, respectively.

The growth media were replaced with 50 μl/well of agonist (either glucagon or forskolin). The cells were incubated with the agonists for 10 minutes at 37° C., 5% $CO_2$. Following incubation, the cells were lysed by the addition of 200 μl of boiling water to each well. After 15 minutes the supernatants were collected and diluted 1:5 or 1:40 in acetate buffer (cAMP [$^{125}$I] Scintillation Proximity Assay System (Amersham)). Samples were acetylated using triethylamine and acetic anhydride according to the protocol provided by the manufacturer.

A 100 μl aliquot of each acetylated sample was combined with 75 μl of $^{125}$I-cAMP, 75 μl anti-succinyl cAMP antisera and 75 μl of donkey anti-rabbit IgG coupled SPA beads (all assay solutions provided in the cAMP [$^{125}$I] Scintillation Proximity Assay System (Amersham)) in a well of an LKB T-tray. The trays were sealed and incubated overnight with continuous shaking on a rotary platform shaker at 200 rpm. The samples were counted in a 1205 BETAPLATE liquid scintillation counter (Pharmacia LKB Instruments Inc., Gaithersburg, Md.). A standard curve of 2–128 fmol acetylated cAMP was also run. Total $^{125}$I-cAMP bound and non-specific binding were also determined. KZ6/rGR-DHFR-2 showed a 140-fold induction of cAMP levels at saturating glucagon (10–100 nM), and an $ED_{50}$ of 0.25 nM.

E. Intracellular Calcium Concentration Determination

Intracellular calcium responses of pLJ4 transfectants to glucagon were assayed using the method essentially as described by Grynkiewicz et al. (*J. Biol. Chem.* 260:3440–3450, 1985, which is incorporated by reference herein in its entirety). Plasmid pLJ4 BHK transfectants seeded into 2 well coverglass chambers (NUNC) at $5\times10^4$ cells per chamber. The cells were grown for between one and three days under normal culture conditions in methotrexate selection medium. The medium was removed by aspiration, and the chambers were rinsed twice with 1 ml Imaging Buffer (Table 3). The cells were incubated for 30 minutes in the dark at room temperature with 0.5 ml of Fura-2 AM Solution (Table 3). After incubation, the Fura-2 AM Solution was removed, and the cells were rinsed with 1 ml Imaging Buffer three times. After the final rinse, 0.5 ml of buffer was left in each chamber. The cells were held in the dark at room temperature from 30 to 120 minutes.

Imaging was performed on a Nikon Diaphot inverted fluorescence microscope equipped with a mercury arc lamp and 10× and 40× Nikon Fluor dry objective lenses. Experiments were controlled and analysed using a Sun SPARC II workstation and Inovision (Research Triangle Park, N.C.) RATIOTOOL software. Alternate excitation wavelengths were controlled by this software through an automated filter wheel containing 340 nm and 380 nm band pass filters. Emission images were directed by a dichroic mirror (380 nm cutoff) to a Dage-MTI 72 CCD camera equipped with a Genesis II image intensifier and digitally recorded by the software.

Intracellular calcium concentration was monitored by calculating a ratio of emission intensities at each of the two excitation wavelenths (340/380) for each pixel of the digital microscopic image field (512×480 pixels). Grynkiewicz et al. (ibid.) have shown that this ratio is related to the calcium concentration seen by the fura-2 dye inside cells which have taken up and de-esterified the acetoxymethyl derivative (fura-2 AM) used to load the cells. The RATIOTOOL software displays this information as a false color image which can be calibrated to calcium concentration. Images were acquired, and this calculation was performed at five-second intervals during each experiment.

Cells were monitored for at least 60 seconds (12 images) to establish baseline conditions before stimulation. Stimulation was performed by adding 0.5 ml of Imaging Buffer containing 200 nM glucagon to the 0.5 ml of Imaging Buffer in the coverglass chamber, thus achieving a 100 nM final concentration. Cells were monitored, and images were recorded for at least three minutes after stimulation.

The ratio images corresponding to a number of cells in each field were observed to change dramatically shortly after the addition of glucagon.

This was quantified by using the RATIOTOOL software to calculate a mean value for specific regions of the ratio image corresponding to each of the responding cells. Cells with an average resting ratio of approximately 1.4 rose rapidly to a value of 3 to 4. They remained at the high value for 40 to 50 seconds and then gradually decayed back to baseline. Independent calibration experiments indicate that this reflects changes in intracellular calcium concentration from a resting value of approximately 150 nM to a peak of approximately 400 nM.

F. Inositol Phosphate Determination

BHK 570 cells expressing the glucagon receptor from pLJ4 or mock-transfected BHK 570 cells were plated into 24-well tissue culture dishes at about 200,000 cells per well. After 24 hours, the cells in each well were labeled by incubation in 0.5 ml of MTX selection media containing 2.0 $\mu$Ci of myo-(2-$^3$H) inositol (specific activity—20 Ci/mmol; A-mersham). At the end of a 24 hour incubation, the cells were washed with 1 ml prewarmed DMEM (Dulbecco's Modified Eagles Medium; JRH Biosciences, Lenexa, Kan.) that had been buffered with 20 mM Hepes, pH 7.0 buffer (Sigma Chemical Co.) containing 10 mM LiCl. The wash media was removed by aspiration and replaced with 900 $\mu$l of fresh buffered media. The cells were incubated for five minutes at 37° C. After incubation, each agonist or antagonist was added to 30 triplicate wells and incubated according to the volumes and conditions set forth in Table 8.

TABLE 8

| VOLUME OF LIGAND | INCUBATION PERIOD |
|---|---|
| pLJ4 transfectants | |
| 100 $\mu$l 1000 nM glucagon | 10 minutes |
| 100 $\mu$l 10 nM glucagon | 10 minutes |
| 100 $\mu$l 100 lM forskolin | 10 minutes |
| mock-transfectants | |
| 100 $\mu$l 1000 nM glucagon | 10 minutes |
| 100 $\mu$l 1000 nM isoproterenol | 10 minutes |
| pLJ4 transfectants | |
| 100 $\mu$l 50 nM glucagon | 30 minutes |
| 100 $\mu$l 50 nM des His$^1$[Glu$^9$]glucagon | 30 minutes |

The reaction was terminated by placing the cells on ice. Following aspiration of the media, the cells were lysed by the addition of 1 ml of cold DMEM and 1 ml of ice-cold 10% perchloric acid. After ten minutes the cell lysates were transferred to tubes on ice, each of which contained 500 $\mu$l 10 mM EDTA, pH 7.0. The samples were neutralized by the addition 900 $\mu$l of 1.5M KOH in 60 mM Hepes Buffer and dropwise addition of the KOH-HEPES solution until a pH between 7 and 7.5 was reached. The neutralized samples were frozen at -20° C. overnight. The frozen samples were thawed, and the precipitate was allowed to settle out of the samples. The supernatants wvere applied to AMPREP mini-columns (Amicon) that had been sequentially washed with five milliliters each of methanol and 1M KHCO$_3$ followed by a wash with 15 ml of water. After the samples were applied, the flow-through was collected. The columns were washed with 1 ml of water four times, and 1 m nl samples were collected after each wash. The inositol phosphates were eluted from the column by four successive 1 ml applications of 0.25M KHCO$_3$ with 1 ml samples collected after each application. Ten milliliters of OPTIFLUOR (Packard Instrument Co., Menden, Conn.) was added to each sample, and the samples were counted. Stimulation of the inositol phosphate pathway was indicated by an increase in labeled inositol phosphate levels. No stimulation in inositol phosphate production was observed in any sample.

G. Expression of a Human Glucagon Receptor in COS 7 Cells

Plasmid pLJ6' was transfected into COS 7 cells using a DEAE-dextran procedure described above. The cells were grown on glass chamber slides (as described in Example 3) for 72 hours after transfection. An in situ glucagon binding assay using $^{125}$I-glucagon followed by emulsion autoradiography was performed as described in Example 3. Greater than 50% of the cells transfected with p LJ6' bound glucagon in a specific fashion.

H. Expression of a Human Glucagon Receptor in BHK570 Cells

BHK570 (deposited with the American Type Culture Collection under Accession number 10314) were transfected with plasmid pLJ6' using the calcium phosphate transfection method (Example 8). Transfected cells were selected in the presence of G418 until single colonies were visible. Single colonies were cloned using cloning cylinders. The clones were shown to bind glucagon using the in situ binding to iodinated glucagon was carried out as described above.

The PLJ6' -transfected cells were assayed for cAMP accumulation essentially as described in Example 8.C. The transfectants were assayed after stimulation with glucagon, secretin, VIP or GLP-I. The assays showed that the pLJ6'-transfected cells accumulated increased concentrations of cAMP following glucagon stimulation than control cells. Stimulation of the transfectants with secretin, VIP or GLP-I showed no increased cAMP accumulation. Intracellular calcium response was determined essentially as described in Example 8.E. Glucagon-stimulated pLJ6'-transfected cells demonstrated an increase in intracellular calcium levels as shown by a rapid rise in the fluorescence of the calcium indicator Fura-2. These results show that pLJ6' encodes a functional human glucagon receptor capable of binding glucagon and facilitating signal transduction.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated and purified polypeptide comprising the amino acid sequence of a glucagon receptor having seven transmembrane domains, an N-terminal extracellular domain, a C-terminal intracellular domain, three extracellular loop domains, and three intracellular loop domains, wherein the receptor is capable of binding glucagon with a $K_D$ no greater than 100 nM and is capable of transducing signal in a suitable host cell in response to such binding, and wherein the receptor is encoded by DNA which hybridizes under conditions of high stringency to a probe having the nucleotide sequence of the complement of nucleotides 145–1599 of SEQ ID NO: 14 or nucleotides 53–1483 of SEQ ID NO: 24.

2. A polypeptide according to claim 1 comprising the amino acid sequence shown as residues 28–485 of SEQ ID NO: 15, residues 1–485 of SEQ ID NO: 15, r residues 1–477 of SEQ ID NO: 25.

3. An isolated and purified polypeptide comprising the amino acid sequence of a glucagon receptor native to a mammal, the receptor having seven transmembrane domains, an N-terminal extracellular domain, a C-terminal intracellular domain, three extracellular loop domains, and three intracellular loop domains, wherein the receptor is encoded by DNA which hybridizes under conditions of high stringency to a probe having the nucleotide sequence of the complement of nucleotides 145–1599 of SEQ ID NO: 14 or nucleotides 53–1483 of SEQ ID NO: 24.

4. A polypeptide according to claim 3, wherein the polypeptide is an allelic variant of the sequence shown in SEQ ID NO: 15 or SEQ ID NO: 25.

5. A peptide comprising the amino acid sequence of a fragment of a polypeptide according to claim 1, or 3, the fragment comprising at least (a) the complete sequence of one of the extracellular or intracellular domains of the receptor, or (b) ten contiguous amino acids from the sequence of the mature receptor.

6. A peptide according to claim 5, wherein the fragment binds glucagon.

7. A peptide according to claim 5, wherein the fragment comprises a receptor domain which is 1ID, 1ELD, 2ID, 2ELD, 3ID, or 3ELD.

8. A peptide according to claim 5, wherein said extracellular or intracellular domain comprises:

(a) residues 169–178 of SEQ ID NO: 15;

(b) residues 303–231 of SEQ ID NO: 15;

(c) residues 259–266 of SEQ ID NO: 15;

(d) residues 293–307 of SEQ ID NO: 15;

(e) residues 334–345 of SEQ ID NO: 15; or (f) residues 371–380 of SEQ ID NO: 15.

9. A peptide comprising the amino acid sequence of a fragment of a glucagon receptor polypeptide having the sequence shown as residues 28–485 of SEQ ID NO: 15, residues 1–485 of SEQ ID NO: 15, or residues 1–477 of SEQ ID NO: 25, the fragment comprising at least (a) the complete sequence of one of the extracellular or intracellular domains of the receptor, or (b) ten contiguous amino acids from the sequence of the receptor.

10. A peptide according to claim 9, wherein the fragment binds glucagon.

11. A peptide according to claim 9, wherein the fragment comprises a receptor domain which is 1ID, 1ELD, 2ID, 2ELD, 3ID, or 3ELD.

12. A monospecific antibody which specifically binds to the amino acid sequence of a glucagon receptor according to claim 1, or 3.

13. An antibody according to claim 12, which is a monoclonal antibody.

14. A hybridoma which produces an antibody according to claim 13.

15. A process for making an antibody specific for a glucagon receptor, comprising the steps of:

administering a peptide according to claim 5 to a host animal; and recovering the antibody from the animal.

16. A process for making an antibody specific for a glucagon receptor, comprising the steps of:

administering a peptide according to claim 9 to a host animal; and recovering the antibody from the animal.

17. A process for making a cell which produces an antibody specific for a glucagon receptor, comprising the steps of:

administering a peptide according to claim 5 to a host animal; and recovering the cell from the animal.

18. A process for making a cell which produces an antibody specific for a glucagon receptor, comprising the steps of:

administering a peptide according to claim 9 to a host animal; and recovering the cell from the animal.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( v i i ) IMMEDIATE SOURCE:
( B ) CLONE: ZC447

( x i ) SEQUENCE DESCRIPTION: SEQ ID NO:1:

TAACAATTTC ACACAGG 17

( 2 ) INFORMATION FOR SEQ ID NO:2:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( v i i ) IMMEDIATE SOURCE:
( B ) CLONE: ZC976

( x i ) SEQUENCE DESCRIPTION: SEQ ID NO:2:

CGTTGTAAAA CGACGGCC 18

( 2 ) INFORMATION FOR SEQ ID NO:3:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( v i i ) IMMEDIATE SOURCE:
( B ) CLONE: ZC982

( x i ) SEQUENCE DESCRIPTION: SEQ ID NO:3:

AATTCCCCTC CCGCGAAGGC GTCGGCGCGG GGCTGGCGTA GGGCCTGCGT CAGCTGCAGC 60

CCGCCGGAGC T 71

( 2 ) INFORMATION FOR SEQ ID NO:4:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( v i i ) IMMEDIATE SOURCE:
( B ) CLONE: ZC983

( x i ) SEQUENCE DESCRIPTION: SEQ ID NO:4:

CCGGCGGGCT GCAGCTGACG CAGGCCCTAC GCCAGCCCCG CGCCGACGCC TTCGCGGGAG 60

GGG 63

( 2 ) INFORMATION FOR SEQ ID NO:5:

( i ) SEQUENCE CHARACTERISTICS:
( A ) LENGTH: 38 base pairs ( B ) TYPE: nucleic acid
            ( C ) STRANDEDNESS: single
            ( D ) TOPOLOGY: linear ( v i i ) IMMEDIATE SOURCE:
            ( B ) CLONE: ZC3509

( x i ) SEQUENCE DESCRIPTION: SEQ ID NO:5:

CAAATTGACG TCATGGTAAA AATTGACGTC ATGGTAAG                                    3 8

( 2 ) INFORMATION FOR SEQ ID NO:6:

( i ) SEQUENCE CHARACTERISTICS:
            ( A ) LENGTH: 46 base pairs
            ( B ) TYPE: nucleic acid
            ( C ) STRANDEDNESS: single
            ( D ) TOPOLOGY: linear ( v i i ) IMMEDIATE SOURCE:
            ( B ) CLONE: ZC3510

( x i ) SEQUENCE DESCRIPTION: SEQ ID NO:6:

AATTCTTACC ATGACGTCAA TTTTACCAT GACGTCAATT TGAGCT                            4 6

( 2 ) INFORMATION FOR SEQ ID NO:7:

( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( v i i ) IMMEDIATE SOURCE:
            ( B ) CLONE: ZC3747

( x i ) SEQUENCE DESCRIPTION: SEQ ID NO:7:

GACAGAGCAC AGAATTCACT ACTCGAGTTT TTTTTTTTTT TT                               4 2

( 2 ) INFORMATION FOR SEQ ID NO:8:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( v i i ) IMMEDIATE SOURCE:
            ( B ) CLONE: ZC4701

( x i ) SEQUENCE DESCRIPTION: SEQ ID NO:8:

ACTCTCCGGT TNARRAARCA RTANA                                                  2 5

( 2 ) INFORMATION FOR SEQ ID NO:9:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear ( v i i ) IMMEDIATE SOURCE:
            ( B ) CLONE: ZC4715

( x i ) SEQUENCE DESCRIPTION: SEQ ID NO:9:

CATCCACGGT AYACNGTNGG NTAYWS                                                 2 6

( 2 ) INFORMATION FOR SEQ ID NO:10:

( i ) SEQUENCE CHARACTERISTICS:
            ( A ) LENGTH: 26 base pairs (B) TYPE: nucleic acid
(C) STRANDEDNESS: single
(D) TOPOLOGY: linear (vii) IMMEDIATE SOURCE:
(B) CLONE: ZC4758

(xi) SEQUENCE DESCRIPTION: SEQ ID NO:10:

GCGGAATTCK MNAYNGTNGG NYAYWS 26

(2) INFORMATION FOR SEQ ID NO:11:

(i) SEQUENCE CHARACTERISTICS:
(A) LENGTH: 26 base pairs
(B) TYPE: nucleic acid
(C) STRANDEDNESS: single
(D) TOPOLOGY: linear (vii) IMMEDIATE SOURCE:
(B) CLONE: ZC4778

(xi) SEQUENCE DESCRIPTION: SEQ ID NO:11:

CGCGGATCCY SRTTNMRRAA RCARTA 26

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (vii) IMMEDIATE SOURCE:
(B) CLONE: ZC5432

(xi) SEQUENCE DESCRIPTION: SEQ ID NO:12:

CAGGACCCGC TACAGCCAGA A 21

(2) INFORMATION FOR SEQ ID NO:13:

(i) SEQUENCE CHARACTERISTICS:
(A) LENGTH: 21 base pairs
(B) TYPE: nucleic acid
(C) STRANDEDNESS: single
(D) TOPOLOGY: linear (vii) IMMEDIATE SOURCE:
(B) CLONE: ZC5433

(xi) SEQUENCE DESCRIPTION: SEQ ID NO:13:

CACCAGAAGC CCATGTTGTC A 21

(2) INFORMATION FOR SEQ ID NO:14:

(i) SEQUENCE CHARACTERISTICS:
(A) LENGTH: 1875 base pairs
(B) TYPE: nucleic acid
(C) STRANDEDNESS: single
(D) TOPOLOGY: linear (ii) MOLECULE TYPE: cDNA (vi) ORIGINAL SOURCE:
(F) TISSUE TYPE: Liver (vii) IMMEDIATE SOURCE:
(B) CLONE: pLJ4

(ix) FEATURE:
(A) NAME/KEY: CDS
(B) LOCATION: 145..1599

( x i ) SEQUENCE DESCRIPTION: SEQ ID NO:14:

| | | | | | | | | | | |
|---|---|---|---|---|---|---|---|---|---|---|
| GAATTCGCGG | CCGCCGCCGG | GCCCCAGATC | CCAGTGCGCG | AGGAGCCCAG | TCCTAGACCC | | | | | 60 |
| AGCAACCTGA | GGAGAGGTGC | ACACACCCCC | AAGGACCCAG | GCACCCAACC | TCTGCCAGAT | | | | | 120 |
| GTGGGGGGGT | GGCTACCCAG | AGGC ATG CTC CTC ACC CAG CTC CAC TGT CCC | | | | | | | | 171 |

```
                        Met Leu Leu Thr Gln Leu His Cys Pro
                         1                   5

TAC CTG CTG CTG CTG CTG GTG GTG CTG TCA TGT CTG CCA AAG GCA CCC    219
Tyr Leu Leu Leu Leu Leu Val Val Leu Ser Cys Leu Pro Lys Ala Pro
 10              15                  20                  25

TCT GCC CAG GTA ATG GAC TTT TTG TTT GAG AAG TGG AAG CTC TAT AGT    267
Ser Ala Gln Val Met Asp Phe Leu Phe Glu Lys Trp Lys Leu Tyr Ser
                 30                  35                  40

GAC CAG TGC CAC CAC AAC CTA AGC CTG CTG CCC CCA CCT ACT GAG CTG    315
Asp Gln Cys His His Asn Leu Ser Leu Leu Pro Pro Pro Thr Glu Leu
             45                  50                  55

GTC TGC AAC AGA ACT TTC GAC AAG TAC TCC TGC TGG CCT GAC ACC CCT    363
Val Cys Asn Arg Thr Phe Asp Lys Tyr Ser Cys Trp Pro Asp Thr Pro
         60                  65                  70

CCC AAC ACC ACT GCC AAC ATT TCC TGC CCC TGG TAC CTA CCT TGG TAC    411
Pro Asn Thr Thr Ala Asn Ile Ser Cys Pro Trp Tyr Leu Pro Trp Tyr
     75                  80                  85

CAC AAA GTG CAG CAC CGC CTA GTG TTC AAG AGG TGT GGG CCT GAT GGG    459
His Lys Val Gln His Arg Leu Val Phe Lys Arg Cys Gly Pro Asp Gly
 90                  95                 100                 105

CAG TGG GTT CGA GGG CCA CGG GGG CAG TCA TGG CGC GAC GCC TCC CAA    507
Gln Trp Val Arg Gly Pro Arg Gly Gln Ser Trp Arg Asp Ala Ser Gln
                110                 115                 120

TGT CAG ATG GAT GAT GAC GAG ATC GAG GTC CAG AAG GGG GTA GCC AAG    555
Cys Gln Met Asp Asp Asp Glu Ile Glu Val Gln Lys Gly Val Ala Lys
             125                 130                 135

ATG TAT AGC AGC TAC CAG GTG ATG TAC ACT GTG GGC TAC AGT CTG TCC    603
Met Tyr Ser Ser Tyr Gln Val Met Tyr Thr Val Gly Tyr Ser Leu Ser
         140                 145                 150

CTG GGG GCC TTG CTC CTG GCG CTG GTC ATC CTG CTG GGC CTC AGG AAG    651
Leu Gly Ala Leu Leu Leu Ala Leu Val Ile Leu Leu Gly Leu Arg Lys
     155                 160                 165

CTG CAC TGC ACC CGG AAC TAC ATC CAC GGG AAC CTG TTC GCG TCC TTC    699
Leu His Cys Thr Arg Asn Tyr Ile His Gly Asn Leu Phe Ala Ser Phe
170                 175                 180                 185

GTG CTC AAG GCT GGC TCT GTG CTG GTC ATT GAT TGG CTG CTC AAG ACA    747
Val Leu Lys Ala Gly Ser Val Leu Val Ile Asp Trp Leu Leu Lys Thr
                190                 195                 200

CGC TAT AGC CAG AAG ATT GGA GAT GAC CTC AGT GTG AGC GTC TGG CTC    795
Arg Tyr Ser Gln Lys Ile Gly Asp Asp Leu Ser Val Ser Val Trp Leu
             205                 210                 215

AGT GAT GGG GCG GTG GCT GGC TGC AGA GTG GCC ACA GTG ATC ATG CAG    843
Ser Asp Gly Ala Val Ala Gly Cys Arg Val Ala Thr Val Ile Met Gln
         220                 225                 230

TAC GGC ATC ATA GCC AAC TAC TGC TGG TTG CTG GTG GAG GGT GTG TAC    891
Tyr Gly Ile Ile Ala Asn Tyr Cys Trp Leu Leu Val Glu Gly Val Tyr
     235                 240                 245

CTG TAC AGC CTG CTG AGC ATC ACC ACC TTC TCG GAG AAG AGC TTC TTC    939
Leu Tyr Ser Leu Leu Ser Ile Thr Thr Phe Ser Glu Lys Ser Phe Phe
250                 255                 260                 265

TCC CTC TAT CTG TGC ATC GGC TGG GGA TCT CCC CTG CTG TTT GTC ATC    987
Ser Leu Tyr Leu Cys Ile Gly Trp Gly Ser Pro Leu Leu Phe Val Ile
                270                 275                 280

CCC TGG GTG GTG GTC AAG TGT CTG TTT GAG AAT GTC CAG TGC TGG ACC   1035
Pro Trp Val Val Val Lys Cys Leu Phe Glu Asn Val Gln Cys Trp Thr
```

|  |  |  |  |  |  |  |  |  |  |  |  |  |  |  |  |
|---|---|---|---|---|---|---|---|---|---|---|---|---|---|---|---|
|  |  |  | 285 |  |  |  |  | 290 |  |  |  |  | 295 |  |  |
| AGC | AAT | GAC | AAT | ATG | GGA | TTC | TGG | TGG | ATC | CTG | CGT | ATC | CCT | GTA | CTC | 1083 |
| Ser | Asn | Asp | Asn | Met | Gly | Phe | Trp | Trp | Ile | Leu | Arg | Ile | Pro | Val | Leu |  |
|  |  | 300 |  |  |  |  | 305 |  |  |  |  | 310 |  |  |  |  |
| CTG | GCC | ATA | CTG | ATC | AAT | TTT | TTC | ATC | TTT | GTC | CGC | ATC | ATT | CAT | CTT | 1131 |
| Leu | Ala | Ile | Leu | Ile | Asn | Phe | Phe | Ile | Phe | Val | Arg | Ile | Ile | His | Leu |  |
|  | 315 |  |  |  |  | 320 |  |  |  |  | 325 |  |  |  |  |  |
| CTT | GTG | GCC | AAG | CTG | CGT | GCC | CAT | CAG | ATG | CAC | TAT | GCT | GAT | TAC | AAG | 1179 |
| Leu | Val | Ala | Lys | Leu | Arg | Ala | His | Gln | Met | His | Tyr | Ala | Asp | Tyr | Lys |  |
| 330 |  |  |  |  | 335 |  |  |  |  | 340 |  |  |  |  | 345 |  |
| TTC | CGG | CTA | GCC | AGG | TCC | ACG | CTG | ACC | CTC | ATT | CCT | CTG | CTG | GGA | GTC | 1227 |
| Phe | Arg | Leu | Ala | Arg | Ser | Thr | Leu | Thr | Leu | Ile | Pro | Leu | Leu | Gly | Val |  |
|  |  |  |  | 350 |  |  |  |  | 355 |  |  |  |  | 360 |  |  |
| CAC | GAA | GTG | GTC | TTT | GCC | TTT | GTG | ACT | GAT | GAG | CAT | GCC | CAG | GGC | ACC | 1275 |
| His | Glu | Val | Val | Phe | Ala | Phe | Val | Thr | Asp | Glu | His | Ala | Gln | Gly | Thr |  |
|  |  |  | 365 |  |  |  |  | 370 |  |  |  |  | 375 |  |  |  |
| CTG | CGC | TCC | ACC | AAG | CTC | TTT | TTT | GAC | CTG | TTC | TTC | AGC | TCC | TTT | CAG | 1323 |
| Leu | Arg | Ser | Thr | Lys | Leu | Phe | Phe | Asp | Leu | Phe | Phe | Ser | Ser | Phe | Gln |  |
|  |  | 380 |  |  |  |  | 385 |  |  |  |  | 390 |  |  |  |  |
| GGT | CTG | CTG | GTG | GCT | GTT | CTC | TAC | TGT | TTC | CTC | AAC | AAG | GAG | GTG | CAG | 1371 |
| Gly | Leu | Leu | Val | Ala | Val | Leu | Tyr | Cys | Phe | Leu | Asn | Lys | Glu | Val | Gln |  |
|  | 395 |  |  |  |  | 400 |  |  |  |  | 405 |  |  |  |  |  |
| GCA | GAG | CTA | CTG | CGG | CGT | TGG | AGG | CGA | TGG | CAA | GAA | GGC | AAA | GCT | CTT | 1419 |
| Ala | Glu | Leu | Leu | Arg | Arg | Trp | Arg | Arg | Trp | Gln | Glu | Gly | Lys | Ala | Leu |  |
| 410 |  |  |  |  | 415 |  |  |  |  | 420 |  |  |  |  | 425 |  |
| CAG | GAG | GAA | AGG | ATG | GCC | AGC | AGC | CAT | GGC | AGC | CAC | ATG | GCC | CCA | GCA | 1467 |
| Gln | Glu | Glu | Arg | Met | Ala | Ser | Ser | His | Gly | Ser | His | Met | Ala | Pro | Ala |  |
|  |  |  |  | 430 |  |  |  |  | 435 |  |  |  |  | 440 |  |  |
| GGG | ACT | TGT | CAT | GGT | GAT | CCC | TGT | GAG | AAA | CTT | CAG | CTT | ATG | AGT | GCA | 1515 |
| Gly | Thr | Cys | His | Gly | Asp | Pro | Cys | Glu | Lys | Leu | Gln | Leu | Met | Ser | Ala |  |
|  |  |  | 445 |  |  |  |  | 450 |  |  |  |  | 455 |  |  |  |
| GGC | AGC | AGC | AGT | GGG | ACT | GGC | TGT | GAG | CCC | TCT | GCG | AAG | ACC | TCA | TTG | 1563 |
| Gly | Ser | Ser | Ser | Gly | Thr | Gly | Cys | Glu | Pro | Ser | Ala | Lys | Thr | Ser | Leu |  |
|  |  | 460 |  |  |  |  | 465 |  |  |  |  | 470 |  |  |  |  |
| GCC | AGT | AGT | CTC | CCA | AGG | CTG | GCT | GAC | AGC | CCC | ACC | TGAATCTCCA |  |  |  | 1609 |
| Ala | Ser | Ser | Leu | Pro | Arg | Leu | Ala | Asp | Ser | Pro | Thr |  |  |  |  |  |
|  | 475 |  |  |  |  | 480 |  |  |  |  | 485 |  |  |  |  |  |

| CTGGACTCCA | GCCAAGTTGG | ATTCAGAAAG | GGCCTCACAA | GACAACCCAG | AAACAGATGC | 1669 |
|---|---|---|---|---|---|---|
| CTGGCCAAGG | CTGAAGAGGC | AAAGCAGCAA | GACAGCAGCT | TGTACTATCC | ACACTCCCCT | 1729 |
| AACCTGTCCT | GGCCGGGTAC | AGGCCACATT | GATGGAGTAG | GGGCTGGATA | TGATGGAGTA | 1789 |
| GCCATGCTAT | GAACTATGGG | TGTTCCCATG | AGTGTTGCCA | TGTTCCATGC | ACACAGATAT | 1849 |
| GACCTTCAGT | AAAGAGCTCC | CGTAGG |  |  |  | 1875 |

( 2 ) INFORMATION FOR SEQ ID NO:15:

( i ) SEQUENCE CHARACTERISTICS:
        ( A ) LENGTH: 485 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

| Met | Leu | Leu | Thr | Gln | Leu | His | Cys | Pro | Tyr | Leu | Leu | Leu | Leu | Leu | Val |
|---|---|---|---|---|---|---|---|---|---|---|---|---|---|---|---|
| 1 |  |  |  | 5 |  |  |  |  | 10 |  |  |  |  | 15 |  |
| Val | Leu | Ser | Cys | Leu | Pro | Lys | Ala | Pro | Ser | Ala | Gln | Val | Met | Asp | Phe |
|  |  |  | 20 |  |  |  |  | 25 |  |  |  |  | 30 |  |  |
| Leu | Phe | Glu | Lys | Trp | Lys | Leu | Tyr | Ser | Asp | Gln | Cys | His | His | Asn | Leu |
|  |  | 35 |  |  |  |  | 40 |  |  |  |  | 45 |  |  |  |

```
Ser  Leu  Leu  Pro  Pro  Pro  Thr  Glu  Leu  Val  Cys  Asn  Arg  Thr  Phe  Asp
     50                      55                 60

Lys  Tyr  Ser  Cys  Trp  Pro  Asp  Thr  Pro  Pro  Asn  Thr  Thr  Ala  Asn  Ile
65                       70                      75                           80

Ser  Cys  Pro  Trp  Tyr  Leu  Pro  Trp  Tyr  His  Lys  Val  Gln  His  Arg  Leu
                         85                      90                      95

Val  Phe  Lys  Arg  Cys  Gly  Pro  Asp  Gly  Gln  Trp  Val  Arg  Gly  Pro  Arg
               100                      105                     110

Gly  Gln  Ser  Trp  Arg  Asp  Ala  Ser  Gln  Cys  Gln  Met  Asp  Asp  Asp  Glu
               115                 120                      125

Ile  Glu  Val  Gln  Lys  Gly  Val  Ala  Lys  Met  Tyr  Ser  Ser  Tyr  Gln  Val
     130                      135                 140

Met  Tyr  Thr  Val  Gly  Tyr  Ser  Leu  Ser  Leu  Gly  Ala  Leu  Leu  Leu  Ala
145                      150                 155                          160

Leu  Val  Ile  Leu  Leu  Gly  Leu  Arg  Lys  Leu  His  Cys  Thr  Arg  Asn  Tyr
               165                      170                     175

Ile  His  Gly  Asn  Leu  Phe  Ala  Ser  Phe  Val  Leu  Lys  Ala  Gly  Ser  Val
               180                 185                      190

Leu  Val  Ile  Asp  Trp  Leu  Leu  Lys  Thr  Arg  Tyr  Ser  Gln  Lys  Ile  Gly
               195                 200                      205

Asp  Asp  Leu  Ser  Val  Ser  Val  Trp  Leu  Ser  Asp  Gly  Ala  Val  Ala  Gly
     210                      215                 220

Cys  Arg  Val  Ala  Thr  Val  Ile  Met  Gln  Tyr  Gly  Ile  Ile  Ala  Asn  Tyr
225                      230                 235                          240

Cys  Trp  Leu  Leu  Val  Glu  Gly  Val  Tyr  Leu  Tyr  Ser  Leu  Leu  Ser  Ile
                    245                 250                     255

Thr  Thr  Phe  Ser  Glu  Lys  Ser  Phe  Phe  Ser  Leu  Tyr  Leu  Cys  Ile  Gly
               260                 265                      270

Trp  Gly  Ser  Pro  Leu  Leu  Phe  Val  Ile  Pro  Trp  Val  Val  Lys  Cys
          275                 280                      285

Leu  Phe  Glu  Asn  Val  Gln  Cys  Trp  Thr  Ser  Asn  Asp  Asn  Met  Gly  Phe
     290                      295                 300

Trp  Trp  Ile  Leu  Arg  Ile  Pro  Val  Leu  Leu  Ala  Ile  Leu  Ile  Asn  Phe
305                      310                 315                          320

Phe  Ile  Phe  Val  Arg  Ile  Ile  His  Leu  Leu  Val  Ala  Lys  Leu  Arg  Ala
                    325                 330                     335

His  Gln  Met  His  Tyr  Ala  Asp  Tyr  Lys  Phe  Arg  Leu  Ala  Arg  Ser  Thr
               340                 345                      350

Leu  Thr  Leu  Ile  Pro  Leu  Leu  Gly  Val  His  Glu  Val  Val  Phe  Ala  Phe
          355                 360                      365

Val  Thr  Asp  Glu  His  Ala  Gln  Gly  Thr  Leu  Arg  Ser  Thr  Lys  Leu  Phe
     370                      375                 380

Phe  Asp  Leu  Phe  Phe  Ser  Ser  Phe  Gln  Gly  Leu  Leu  Val  Ala  Val  Leu
385                      390                 395                          400

Tyr  Cys  Phe  Leu  Asn  Lys  Glu  Val  Gln  Ala  Glu  Leu  Leu  Arg  Arg  Trp
                    405                 410                     415

Arg  Arg  Trp  Gln  Glu  Gly  Lys  Ala  Leu  Gln  Glu  Glu  Arg  Met  Ala  Ser
               420                 425                      430

Ser  His  Gly  Ser  His  Met  Ala  Pro  Ala  Gly  Thr  Cys  His  Gly  Asp  Pro
          435                 440                      445

Cys  Glu  Lys  Leu  Gln  Leu  Met  Ser  Ala  Gly  Ser  Ser  Ser  Gly  Thr  Gly
     450                      455                 460

Cys  Glu  Pro  Ser  Ala  Lys  Thr  Ser  Leu  Ala  Ser  Ser  Leu  Pro  Arg  Leu
```

```
                                                      465                470                475                480
Ala Asp Ser Pro Thr
                485

( 2 ) INFORMATION FOR SEQ ID NO:16:

( i ) SEQUENCE CHARACTERISTICS:
                ( A ) LENGTH: 576 base pairs
                ( B ) TYPE: nucleic acid
                ( C ) STRANDEDNESS: single
                ( D ) TOPOLOGY: linear ( v i i ) IMMEDIATE SOURCE:
                ( B ) CLONE: G30

( i x ) FEATURE:
                ( A ) NAME/KEY: intron
                ( B ) LOCATION: 225..314

( i x ) FEATURE:
                ( A ) NAME/KEY: exon
                ( B ) LOCATION: 1..225

( i x ) FEATURE:
                ( A ) NAME/KEY: exon
                ( B ) LOCATION: 315..576

( x i ) SEQUENCE DESCRIPTION: SEQ ID NO:16:

GACATGGTAG   GTCACAGCCT   GTCCCTGGGG   GCCCTGCTCC   TCGCCTTGGC   CATCCTGGGG       60
GGCCTCAGCA   AGCTGCACTG   CACCCGCAAT   GCCATCCACG   CGAATCTGTT   TGCGTCCTTC      120
GTGCTGAAAG   CCAGCTCCGT   GCTGGTCATT   GATGGGCTGC   TCAGGACCCG   CTACAGCAG       180
AAAATTGGCG   ACGACCTCAG   TGTCAGCACC   TGGCTCAGTG   ATGGAGTGAG   CCCCCCTCGG      240
CGGCCCCAGG   CAGGTGGGTG   GGTGGGCAGC   CAGGCAGGTG   GCCACGTAGC   CGCGTCACAC      300
TGCACCTGTA   CCAGGCGGTG   GCTGGCTGCC   GTGTGGCCGC   GGTGTTCATG   CAATATGGCA      360
TCGTGGCCAA   CTACTGCTGG   CTGCTGGTGG   AGGGCCTGTA   CCTGCACAAC   CTGCTGGGCC      420
TGGCCACCTT   CCCCGAGAGG   AGCTTCTTCA   GCCTCTACCT   GGGCATCGGC   TGGGGTGCCC      480
CCATGCTGTT   CGTCGTCCCC   TGGGCAGTGG   TCAAGTGTCT   GTTCGAGAAC   GTCCAGTGCT      540
GGACCAGCAA   TGACAACATG   GGCTTCTGGT   GGATCC                                    576

( 2 ) INFORMATION FOR SEQ ID NO:17:

( i ) SEQUENCE CHARACTERISTICS:
                ( A ) LENGTH: 487 base pairs
                ( B ) TYPE: nucleic acid
                ( C ) STRANDEDNESS: single
                ( D ) TOPOLOGY: linear ( v i i ) IMMEDIATE SOURCE:
                ( B ) CLONE: 40-2-2

( i x ) FEATURE:
                ( A ) NAME/KEY: CDS
                ( B ) LOCATION: 1..486

( x i ) SEQUENCE DESCRIPTION: SEQ ID NO:17:

GAC  ATG  GTA  GGT  CAC  AGC  CTG  TCC  CTG  GGG  GCC  CTG  CTC  CTC  GCC  TTG      48
Asp  Met  Val  Gly  His  Ser  Leu  Ser  Leu  Gly  Ala  Leu  Leu  Leu  Ala  Leu
 1                  5                        10                       15

GCC  ATC  CTG  GGG  GGC  CTC  AGC  AAG  CTG  CAC  TGC  ACC  CGC  AAT  GCC  ATC      96
Ala  Ile  Leu  Gly  Gly  Leu  Ser  Lys  Leu  His  Cys  Thr  Arg  Asn  Ala  Ile
           20                       25                       30

CAC  GCG  AAT  CTG  TTT  GCG  TCC  TTC  GTG  CTG  AAA  GCC  AGC  TCC  GTG  CTG     144
His  Ala  Asn  Leu  Phe  Ala  Ser  Phe  Val  Leu  Lys  Ala  Ser  Ser  Val  Leu
                35                       40                       45
```

```
GTC  ATT  GAT  GGG  CTG  CTC  AGG  ACC  CGC  TAC  AGC  CAG  AAA  ATT  GGC  GAC      192
Val  Ile  Asp  Gly  Leu  Leu  Arg  Thr  Arg  Tyr  Ser  Gln  Lys  Ile  Gly  Asp
     50                      55                      60

GAC  CTC  AGT  GTC  AGC  ACC  TGG  CTC  AGT  GAT  GGA  GCG  GTG  GCT  GGC  TGC      240
Asp  Leu  Ser  Val  Ser  Thr  Trp  Leu  Ser  Asp  Gly  Ala  Val  Ala  Gly  Cys
65                      70                      75                           80

CGT  GTG  GCC  GCG  GTG  TTC  ATG  CAA  TAT  GGC  ATC  GTG  GCC  AAC  TAC  TGC      288
Arg  Val  Ala  Ala  Val  Phe  Met  Gln  Tyr  Gly  Ile  Val  Ala  Asn  Tyr  Cys
               85                      90                           95

TGG  CTG  CTG  GTG  GAG  GGC  CTG  TAC  CTG  CAC  AAC  CTG  CTG  GGC  CTG  GCC      336
Trp  Leu  Leu  Val  Glu  Gly  Leu  Tyr  Leu  His  Asn  Leu  Leu  Gly  Leu  Ala
               100                      105                     110

ACC  TTC  CCC  GAG  AGG  AGC  TTC  TTC  AGC  CTC  TAC  CTG  GGC  ATC  GGC  TGG      384
Thr  Phe  Pro  Glu  Arg  Ser  Phe  Phe  Ser  Leu  Tyr  Leu  Gly  Ile  Gly  Trp
          115                           120                     125

GGT  GCC  CCC  ATG  CTG  TTC  GTC  GTC  CCC  TGG  GCA  GTG  GTC  AAG  TGT  CTG      432
Gly  Ala  Pro  Met  Leu  Phe  Val  Val  Pro  Trp  Ala  Val  Val  Lys  Cys  Leu
     130                      135                     140

TTC  GAG  AAC  GTC  CAG  TGC  TGG  ACC  AGC  AAT  GAC  AAC  ATG  GGC  TTC  TGG      480
Phe  Glu  Asn  Val  Gln  Cys  Trp  Thr  Ser  Asn  Asp  Asn  Met  Gly  Phe  Trp
145                      150                     155                          160

TGG  ATC  C                                                                          487
Trp  Ile
```

( 2 ) INFORMATION FOR SEQ ID NO:18:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Asp  Met  Val  Gly  His  Ser  Leu  Ser  Leu  Gly  Ala  Leu  Leu  Leu  Ala  Leu
1                        5                        10                     15

Ala  Ile  Leu  Gly  Gly  Leu  Ser  Lys  Leu  His  Cys  Thr  Arg  Asn  Ala  Ile
               20                       25                      30

His  Ala  Asn  Leu  Phe  Ala  Ser  Phe  Val  Leu  Lys  Ala  Ser  Ser  Val  Leu
               35                       40                      45

Val  Ile  Asp  Gly  Leu  Leu  Arg  Thr  Arg  Tyr  Ser  Gln  Lys  Ile  Gly  Asp
     50                      55                      60

Asp  Leu  Ser  Val  Ser  Thr  Trp  Leu  Ser  Asp  Gly  Ala  Val  Ala  Gly  Cys
65                      70                      75                           80

Arg  Val  Ala  Ala  Val  Phe  Met  Gln  Tyr  Gly  Ile  Val  Ala  Asn  Tyr  Cys
               85                      90                           95

Trp  Leu  Leu  Val  Glu  Gly  Leu  Tyr  Leu  His  Asn  Leu  Leu  Gly  Leu  Ala
               100                     105                     110

Thr  Phe  Pro  Glu  Arg  Ser  Phe  Phe  Ser  Leu  Tyr  Leu  Gly  Ile  Gly  Trp
          115                           120                     125

Gly  Ala  Pro  Met  Leu  Phe  Val  Val  Pro  Trp  Ala  Val  Val  Lys  Cys  Leu
     130                      135                     140

Phe  Glu  Asn  Val  Gln  Cys  Trp  Thr  Ser  Asn  Asp  Asn  Met  Gly  Phe  Trp
145                      150                     155                          160

Trp  Ile
```

( 2 ) INFORMATION FOR SEQ ID NO:19:

( i ) SEQUENCE CHARACTERISTICS:

( A ) LENGTH: 21 base pairs
( B ) TYPE: nucleic acid
( C ) STRANDEDNESS: single
( D ) TOPOLOGY: linear ( v i i ) IMMEDIATE SOURCE:
( B ) CLONE: ZC4812

( x i ) SEQUENCE DESCRIPTION: SEQ ID NO:19:

GTGAGTTCAC GAATTCCATG G  21

( 2 ) INFORMATION FOR SEQ ID NO:20:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( v i i ) IMMEDIATE SOURCE:
( B ) CLONE: ZC4814

( x i ) SEQUENCE DESCRIPTION: SEQ ID NO:20:

AGTTCACGAA TTCCATGGCC CCCCCCCCC CCCC  34

( 2 ) INFORMATION FOR SEQ ID NO:21:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( v i i ) IMMEDIATE SOURCE:
( B ) CLONE: ZC5624

( x i ) SEQUENCE DESCRIPTION: SEQ ID NO:21:

CGCATCTCTT GAACACGAAG  20

( 2 ) INFORMATION FOR SEQ ID NO:22:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( v i i ) IMMEDIATE SOURCE:
( B ) CLONE: ZC5763

( x i ) SEQUENCE DESCRIPTION: SEQ ID NO:22:

GAGAGAGAGA GAGAATTCGG AGGAGCGTAC ACACACACCA G  41

( 2 ) INFORMATION FOR SEQ ID NO:23:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( v i i ) IMMEDIATE SOURCE:
( B ) CLONE: ZC5849

( x i ) SEQUENCE DESCRIPTION: SEQ ID NO:23:

AGAGAGAGAG AGAGCTCGAG TTTATTGTTG GAGGACATTT CCAT  44

( 2 ) INFORMATION FOR SEQ ID NO:24:

( i ) SEQUENCE CHARACTERISTICS:

(A) LENGTH: 1809 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Homo sapiens (vii) IMMEDIATE SOURCE:
(B) CLONE: pLJ6'

(ix) FEATURE:
(A) NAME/KEY: CDS
(B) LOCATION: 53..1486

(xi) SEQUENCE DESCRIPTION: SEQ ID NO:24:

```
GAATTCTGTG CAGCCCCTGC CAGATGTGGG AGGCAGCTAG CTGCCCAGAG GC ATG                55
                                                            Met
                                                            1

CCC CCC TGC CAG CCA CAG CGA CCC CTG CTG CTG TTG CTG CTG CTG CTG             103
Pro Pro Cys Gln Pro Gln Arg Pro Leu Leu Leu Leu Leu Leu Leu Leu
            5                   10                  15

GCC TGC CAG CCA CAG GTC CCC TCC GCT CAG GTG ATG GAC TTC CTG TTT             151
Ala Cys Gln Pro Gln Val Pro Ser Ala Gln Val Met Asp Phe Leu Phe
        20                  25                  30

GAG AAG TGG AAG CTC TAC GGT GAC CAG TGT CAC CAC AAC CTG AGC CTG             199
Glu Lys Trp Lys Leu Tyr Gly Asp Gln Cys His His Asn Leu Ser Leu
    35                  40                  45

CTG CCC CCT CCC ACG GAG CTG GTG TGC AAC AGA ACC TTC GAC AAG TAT             247
Leu Pro Pro Pro Thr Glu Leu Val Cys Asn Arg Thr Phe Asp Lys Tyr
50                  55                  60                  65

TCC TGC TGG CCG GAC ACC CCC GCC AAT ACC ACG GCC AAC ATC TCC TGC             295
Ser Cys Trp Pro Asp Thr Pro Ala Asn Thr Thr Ala Asn Ile Ser Cys
                70                  75                  80

CCC TGG TAC CTG CCT TGG CAC CAC AAA GTG CAA CAC CGC TTC GTG TTC             343
Pro Trp Tyr Leu Pro Trp His His Lys Val Gln His Arg Phe Val Phe
            85                  90                  95

AAG AGA TGC GGG CCC GAC GGT CAG TGG GTG CGT GGA CCC CGG GGG CAG             391
Lys Arg Cys Gly Pro Asp Gly Gln Trp Val Arg Gly Pro Arg Gly Gln
        100                 105                 110

CCT TGG CGT GAT GCC TCC CAG TGC CAG ATG GAT GGC GAG GAG ATT GAG             439
Pro Trp Arg Asp Ala Ser Gln Cys Gln Met Asp Gly Glu Glu Ile Glu
    115                 120                 125

GTC CAG AAG GAG GTG GCC AAG ATG TAC AGC AGC TTC CAG GTG ATG TAC             487
Val Gln Lys Glu Val Ala Lys Met Tyr Ser Ser Phe Gln Val Met Tyr
130                 135                 140                 145

ACA GTG GGC TAC AGC CTG TCC CTG GGG GCC CTG CTC CTC GCC TTG GCC             535
Thr Val Gly Tyr Ser Leu Ser Leu Gly Ala Leu Leu Leu Ala Leu Ala
                150                 155                 160

ATC CTG GGG GGC CTC AGC AAG CTG CAC TGC ACC CGC AAT GCC ATC CAC             583
Ile Leu Gly Gly Leu Ser Lys Leu His Cys Thr Arg Asn Ala Ile His
            165                 170                 175

GCG AAT CTG TTT GCG TCC TTC GTG CTG AAA GCC AGC TCC GTG CTG GTC             631
Ala Asn Leu Phe Ala Ser Phe Val Leu Lys Ala Ser Ser Val Leu Val
        180                 185                 190

ATT GAT GGG CTG CTC AGG ACC CGC TAC AGC CAG AAA ATT GGC GAC GAC             679
Ile Asp Gly Leu Leu Arg Thr Arg Tyr Ser Gln Lys Ile Gly Asp Asp
    195                 200                 205

CTC AGT GTC AGC ACC TGG CTC AGT GAT GGA GCG GTG GCT GGC TGC CGT             727
Leu Ser Val Ser Thr Trp Leu Ser Asp Gly Ala Val Ala Gly Cys Arg
210                 215                 220                 225

GTG GCC GCG GTG TTC ATG CAA TAT GGC ATC GTG GCC AAC TAC TGC TGG             775
```

|  |  |  |  |  |  |  |  |  |  |  |  |  |  |  |  |
|---|---|---|---|---|---|---|---|---|---|---|---|---|---|---|---|
| Val | Ala | Ala | Val | Phe 230 | Met | Gln | Tyr | Gly | Ile 235 | Val | Ala | Asn | Tyr | Cys | Trp 240 |

```
CTG  CTG  GTG  GAG  GGC  CTG  TAC  CTG  CAC  AAC  CTG  CTG  GGC  CTG  GCC  ACC    823
Leu  Leu  Val  Glu  Gly  Leu  Tyr  Leu  His  Asn  Leu  Leu  Gly  Leu  Ala  Thr
               245                      250                     255

CTC  CCC  GAG  AGG  AGC  TTC  TTC  AGC  CTC  TAC  CTG  GGC  ATC  GGC  TGG  GGT    871
Leu  Pro  Glu  Arg  Ser  Phe  Phe  Ser  Leu  Tyr  Leu  Gly  Ile  Gly  Trp  Gly
               260                      265                     270

GCC  CCC  ATG  CTG  TTC  GTC  GTC  CCC  TGG  GCA  GTG  GTC  AAG  TGT  CTG  TTC    919
Ala  Pro  Met  Leu  Phe  Val  Val  Pro  Trp  Ala  Val  Val  Lys  Cys  Leu  Phe
          275                      280                     285

GAG  AAC  GTC  CAG  TGC  TGG  ACC  AGC  AAT  GAC  AAC  ATG  GGC  TTC  TGG  TGG    967
Glu  Asn  Val  Gln  Cys  Trp  Thr  Ser  Asn  Asp  Asn  Met  Gly  Phe  Trp  Trp
290                      295                     300                          305

ATC  CTG  CGG  TTC  CCC  GTC  TTC  CTG  GCC  ATC  CTG  ATC  AAC  TTC  TTC  ATC   1015
Ile  Leu  Arg  Phe  Pro  Val  Phe  Leu  Ala  Ile  Leu  Ile  Asn  Phe  Phe  Ile
               310                      315                     320

TTC  GTC  CGC  ATC  GTT  CAG  CTG  CTC  GTG  GCC  AAG  CTG  CGG  GCA  CGG  CAG   1063
Phe  Val  Arg  Ile  Val  Gln  Leu  Leu  Val  Ala  Lys  Leu  Arg  Ala  Arg  Gln
               325                      330                     335

ATG  CAC  CAC  ACA  GAC  TAC  AAG  TTC  CGG  CTG  GCC  AAG  TCC  ACG  CTG  ACC   1111
Met  His  His  Thr  Asp  Tyr  Lys  Phe  Arg  Leu  Ala  Lys  Ser  Thr  Leu  Thr
               340                      345                     350

CTC  ATC  CCT  CTG  CTG  GGC  GTC  CAC  GAA  GTG  GTC  TTT  GCC  TTC  GTG  ACG   1159
Leu  Ile  Pro  Leu  Leu  Gly  Val  His  Glu  Val  Val  Phe  Ala  Phe  Val  Thr
          355                      360                     365

GAC  GAG  CAC  GCC  CAG  GGC  ACC  CTG  CGC  TCC  GCC  AAG  CTC  TTC  TTC  GAC   1207
Asp  Glu  His  Ala  Gln  Gly  Thr  Leu  Arg  Ser  Ala  Lys  Leu  Phe  Phe  Asp
370                      375                     380                          385

CTC  TTC  CTC  AGC  TCC  TTC  CAG  GGC  CTG  CTG  GTG  GCT  GTC  CTC  TAC  TGC   1255
Leu  Phe  Leu  Ser  Ser  Phe  Gln  Gly  Leu  Leu  Val  Ala  Val  Leu  Tyr  Cys
               390                      395                     400

TTC  CTC  AAC  AAG  GAG  GTG  CAG  TCG  GAG  CTG  CGG  CGG  CGT  TGG  CAC  CGC   1303
Phe  Leu  Asn  Lys  Glu  Val  Gln  Ser  Glu  Leu  Arg  Arg  Arg  Trp  His  Arg
               405                      410                     415

TGG  CGC  CTG  GGC  AAA  GTG  CTA  TGG  GAG  GAG  CGG  AAC  ACC  AGC  AAC  CAC   1351
Trp  Arg  Leu  Gly  Lys  Val  Leu  Trp  Glu  Glu  Arg  Asn  Thr  Ser  Asn  His
               420                      425                     430

AGG  GCC  TCA  TCT  TCG  CCC  GGC  CAC  GGC  CCT  CCC  AGC  AAG  GAG  CTG  CAG   1399
Arg  Ala  Ser  Ser  Ser  Pro  Gly  His  Gly  Pro  Pro  Ser  Lys  Glu  Leu  Gln
               435                      440                     445

TTT  GGG  AGG  GGT  GGT  GGC  AGC  CAG  GAT  TCA  TCT  GCG  GAG  ACC  CCC  TTG   1447
Phe  Gly  Arg  Gly  Gly  Gly  Ser  Gln  Asp  Ser  Ser  Ala  Glu  Thr  Pro  Leu
450                      455                     460                          465

GCT  GGT  GGC  CTC  CCT  AGA  TTG  GCT  GAG  AGC  CCC  TTC  TGAACCCTGC            1493
Ala  Gly  Gly  Leu  Pro  Arg  Leu  Ala  Glu  Ser  Pro  Phe
               470                      475

TGGGACCCCA  GCTAGGGCTG  GACTCTGGCA  CCCAGAGGCG  TCGCTGGACA  ACCCAGAACT          1553

GGACGCCCAG  CTGAGGCTGG  GGGCGGGGGA  GCCAACAGCA  GCCCCCACCT  ACCCCCCACC          1613

CCCAGTGTGG  CTGTCTGCGA  GATTGGGCCT  CCTCTCCCTG  CACCTGCCTT  GTCCCTGGTG          1673

CAGAGGTGAG  CAGAGGAGTC  CAGGGCGGGA  GTGGGGGCTG  TGCCGTGAAC  TGCGTGCCAG          1733

TGTCCCCACG  TATGTCGGCA  CGTCCCATGT  GCATGGAAAT  GTCCTCCAAC  AATAAAGAGC          1793

TCAAGTGGTC  ACCGAG                                                              1809
```

( 2 ) INFORMATION FOR SEQ ID NO:25:

( i ) SEQUENCE CHARACTERISTICS:
        ( A ) LENGTH: 477 amino acids ( B ) TYPE: amino acid
( D ) TOPOLOGY: linear ( i i ) MOLECULE TYPE: protein ( x i ) SEQUENCE DESCRIPTION: SEQ ID NO:25:

| Met | Pro | Pro | Cys | Gln | Pro | Gln | Arg | Pro | Leu | Leu | Leu | Leu | Leu | Leu | Leu |
|---|---|---|---|---|---|---|---|---|---|---|---|---|---|---|---|
| 1 | | | | 5 | | | | | 10 | | | | | 15 | |

| Leu | Ala | Cys | Gln | Pro | Gln | Val | Pro | Ser | Ala | Gln | Val | Met | Asp | Phe | Leu |
|---|---|---|---|---|---|---|---|---|---|---|---|---|---|---|---|
| | | | 20 | | | | 25 | | | | | 30 | | | |

| Phe | Glu | Lys | Trp | Lys | Leu | Tyr | Gly | Asp | Gln | Cys | His | His | Asn | Leu | Ser |
|---|---|---|---|---|---|---|---|---|---|---|---|---|---|---|---|
| | | | 35 | | | | 40 | | | | | 45 | | | |

| Leu | Leu | Pro | Pro | Pro | Thr | Glu | Leu | Val | Cys | Asn | Arg | Thr | Phe | Asp | Lys |
|---|---|---|---|---|---|---|---|---|---|---|---|---|---|---|---|
| | 50 | | | | | 55 | | | | | 60 | | | | |

| Tyr | Ser | Cys | Trp | Pro | Asp | Thr | Pro | Ala | Asn | Thr | Thr | Ala | Asn | Ile | Ser |
|---|---|---|---|---|---|---|---|---|---|---|---|---|---|---|---|
| 65 | | | | | 70 | | | | | 75 | | | | | 80 |

| Cys | Pro | Trp | Tyr | Leu | Pro | Trp | His | His | Lys | Val | Gln | His | Arg | Phe | Val |
|---|---|---|---|---|---|---|---|---|---|---|---|---|---|---|---|
| | | | | 85 | | | | | 90 | | | | | 95 | |

| Phe | Lys | Arg | Cys | Gly | Pro | Asp | Gly | Gln | Trp | Val | Arg | Gly | Pro | Arg | Gly |
|---|---|---|---|---|---|---|---|---|---|---|---|---|---|---|---|
| | | | 100 | | | | 105 | | | | | 110 | | | |

| Gln | Pro | Trp | Arg | Asp | Ala | Ser | Gln | Cys | Gln | Met | Asp | Gly | Glu | Glu | Ile |
|---|---|---|---|---|---|---|---|---|---|---|---|---|---|---|---|
| | | | 115 | | | | 120 | | | | | 125 | | | |

| Glu | Val | Gln | Lys | Glu | Val | Ala | Lys | Met | Tyr | Ser | Ser | Phe | Gln | Val | Met |
|---|---|---|---|---|---|---|---|---|---|---|---|---|---|---|---|
| | 130 | | | | | 135 | | | | | 140 | | | | |

| Tyr | Thr | Val | Gly | Tyr | Ser | Leu | Ser | Leu | Gly | Ala | Leu | Leu | Leu | Ala | Leu |
|---|---|---|---|---|---|---|---|---|---|---|---|---|---|---|---|
| 145 | | | | | 150 | | | | | 155 | | | | | 160 |

| Ala | Ile | Leu | Gly | Gly | Leu | Ser | Lys | Leu | His | Cys | Thr | Arg | Asn | Ala | Ile |
|---|---|---|---|---|---|---|---|---|---|---|---|---|---|---|---|
| | | | | 165 | | | | | 170 | | | | | 175 | |

| His | Ala | Asn | Leu | Phe | Ala | Ser | Phe | Val | Leu | Lys | Ala | Ser | Ser | Val | Leu |
|---|---|---|---|---|---|---|---|---|---|---|---|---|---|---|---|
| | | | 180 | | | | 185 | | | | | 190 | | | |

| Val | Ile | Asp | Gly | Leu | Leu | Arg | Thr | Arg | Tyr | Ser | Gln | Lys | Ile | Gly | Asp |
|---|---|---|---|---|---|---|---|---|---|---|---|---|---|---|---|
| | | 195 | | | | | 200 | | | | | 205 | | | |

| Asp | Leu | Ser | Val | Ser | Thr | Trp | Leu | Ser | Asp | Gly | Ala | Val | Ala | Gly | Cys |
|---|---|---|---|---|---|---|---|---|---|---|---|---|---|---|---|
| | 210 | | | | | 215 | | | | | 220 | | | | |

| Arg | Val | Ala | Ala | Val | Phe | Met | Gln | Tyr | Gly | Ile | Val | Ala | Asn | Tyr | Cys |
|---|---|---|---|---|---|---|---|---|---|---|---|---|---|---|---|
| 225 | | | | | 230 | | | | | 235 | | | | | 240 |

| Trp | Leu | Leu | Val | Glu | Gly | Leu | Tyr | Leu | His | Asn | Leu | Leu | Gly | Leu | Ala |
|---|---|---|---|---|---|---|---|---|---|---|---|---|---|---|---|
| | | | | 245 | | | | | 250 | | | | | 255 | |

| Thr | Leu | Pro | Glu | Arg | Ser | Phe | Phe | Ser | Leu | Tyr | Leu | Gly | Ile | Gly | Trp |
|---|---|---|---|---|---|---|---|---|---|---|---|---|---|---|---|
| | | | 260 | | | | | 265 | | | | | 270 | | |

| Gly | Ala | Pro | Met | Leu | Phe | Val | Val | Pro | Trp | Ala | Val | Val | Lys | Cys | Leu |
|---|---|---|---|---|---|---|---|---|---|---|---|---|---|---|---|
| | | | 275 | | | | 280 | | | | | 285 | | | |

| Phe | Glu | Asn | Val | Gln | Cys | Trp | Thr | Ser | Asn | Asp | Asn | Met | Gly | Phe | Trp |
|---|---|---|---|---|---|---|---|---|---|---|---|---|---|---|---|
| | 290 | | | | | 295 | | | | | 300 | | | | |

| Trp | Ile | Leu | Arg | Phe | Pro | Val | Phe | Leu | Ala | Ile | Leu | Ile | Asn | Phe | Phe |
|---|---|---|---|---|---|---|---|---|---|---|---|---|---|---|---|
| 305 | | | | | 310 | | | | | 315 | | | | | 320 |

| Ile | Phe | Val | Arg | Ile | Val | Gln | Leu | Leu | Val | Ala | Lys | Leu | Arg | Ala | Arg |
|---|---|---|---|---|---|---|---|---|---|---|---|---|---|---|---|
| | | | | 325 | | | | | 330 | | | | | 335 | |

| Gln | Met | His | His | Thr | Asp | Tyr | Lys | Phe | Arg | Leu | Ala | Lys | Ser | Thr | Leu |
|---|---|---|---|---|---|---|---|---|---|---|---|---|---|---|---|
| | | | 340 | | | | | 345 | | | | | 350 | | |

| Thr | Leu | Ile | Pro | Leu | Leu | Gly | Val | His | Glu | Val | Val | Phe | Ala | Phe | Val |
|---|---|---|---|---|---|---|---|---|---|---|---|---|---|---|---|
| | | 355 | | | | | 360 | | | | | 365 | | | |

| Thr | Asp | Glu | His | Ala | Gln | Gly | Thr | Leu | Arg | Ser | Ala | Lys | Leu | Phe | Phe |
|---|---|---|---|---|---|---|---|---|---|---|---|---|---|---|---|
| | 370 | | | | | 375 | | | | | 380 | | | | |

| Asp | Leu | Phe | Leu | Ser | Ser | Phe | Gln | Gly | Leu | Leu | Val | Ala | Val | Leu | Tyr |
|---|---|---|---|---|---|---|---|---|---|---|---|---|---|---|---|

| 385 | | | | 390 | | | | 395 | | | | 400 | |
|---|---|---|---|---|---|---|---|---|---|---|---|---|---|
| Cys | Phe | Leu | Asn | Lys 405 | Glu | Val | Gln | Ser | Glu 410 | Leu | Arg | Arg | Arg | Trp | His 415 |
| Arg | Trp | Arg | Leu 420 | Gly | Lys | Val | Leu | Trp 425 | Glu | Glu | Arg | Asn | Thr 430 | Ser | Asn |
| His | Arg | Ala 435 | Ser | Ser | Ser | Pro | Gly 440 | His | Gly | Pro | Pro | Ser 445 | Lys | Glu | Leu |
| Gln | Phe 450 | Gly | Arg | Gly | Gly | Gly 455 | Ser | Gln | Asp | Ser | Ser 460 | Ala | Glu | Thr | Pro |
| Leu 465 | Ala | Gly | Gly | Leu | Pro 470 | Arg | Leu | Ala | Glu | Ser 475 | Pro | Phe | | | |